US010138234B2

(12) United States Patent
Borroni et al.

(10) Patent No.: US 10,138,234 B2
(45) Date of Patent: *Nov. 27, 2018

(54) 2-PHENYL OR 2-HETARYL IMIDAZOL[1,2-A]PYRIDINE DERIVATIVES

(71) Applicant: Hoffmann-La Roche Inc., Little Falls, NJ (US)

(72) Inventors: Edilio Borroni, Basel (CH); Luca Gobbi, Muttenz (CH); Michael Honer, Zurich (CH); Henner Knust, Rheinfelden (DE); Matthias Koerner, Grenzach-Wyhlen (DE); Dieter Muri, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 54 days.

This patent is subject to a terminal disclaimer.

(21) Appl. No.: 14/925,574

(22) Filed: Oct. 28, 2015

(65) Prior Publication Data

US 2016/0244441 A1  Aug. 25, 2016

Related U.S. Application Data

(63) Continuation of application No. PCT/EP2014/058415, filed on Apr. 25, 2014.

(30) Foreign Application Priority Data

Apr. 29, 2013 (EP) ..................................... 13165676

(51) Int. Cl.
| | | |
|---|---|---|
| A61K 51/00 | (2006.01) |
| A61M 36/14 | (2006.01) |
| C07D 471/04 | (2006.01) |
| A61K 49/00 | (2006.01) |

(52) U.S. Cl.
CPC ........ *C07D 471/04* (2013.01); *A61K 49/0002* (2013.01)

(58) Field of Classification Search
CPC .. C07D 471/04; C07D 213/02; C07D 309/32; C07D 233/02; A61K 49/00; A61K 49/0002
USPC ........... 424/1.11, 1.65, 1.81; 548/300, 347.1, 548/335.1
See application file for complete search history.

(56) References Cited

U.S. PATENT DOCUMENTS

5,654,436 A * 8/1997 Elokdah ............... C07D 235/08
                                                          546/273.4
9,957,266 B2 * 5/2018 Gobbi ................... C07D 471/04
2011/0171739 A1   7/2011 Kemp et al.

FOREIGN PATENT DOCUMENTS

| EP | 1956013 A1 | 8/2008 |
| JP | 2005-512945 A | 5/2005 |
| JP | 2010-516672 A | 5/2010 |
| JP | 2012-502966 A | 2/2012 |
| WO | 2008/118122 A1 | 2/2008 |
| WO | 2011/036127 A1 | 3/2011 |

OTHER PUBLICATIONS

Donohoe et al, Organic & Biomolecular Chemistry, 2012, vol. 10, pp. 1093-1101.*
ISR for PCT/EP2014/058415, (2014).
Written Opinion for PCT/EP2014/058415, (2014).
Clifford et al., "A systematic study of carboxylic acids in negative ion mode electrospray ionisation mass spectrometry providing a structural model for ion suppression" Rapid Communications in Mass Spectrometry 21(13):2014-2018 ( 2007).

* cited by examiner

*Primary Examiner* — D. L. Jones
(74) *Attorney, Agent, or Firm* — Tamara A. Kale

(57) ABSTRACT

The invention relates to compounds of formula I:

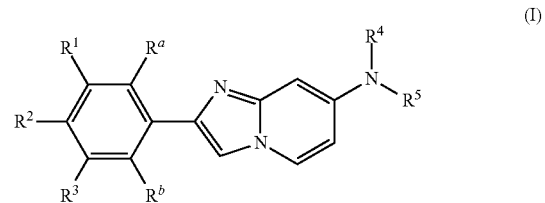

and to pharmaceutically acceptable acid addition salts thereof, wherein $R^1$-$R^6$, $R^a$, and $R^b$ have any of the values defined in the specification. The compounds are suitable as imaging tools.

7 Claims, 2 Drawing Sheets

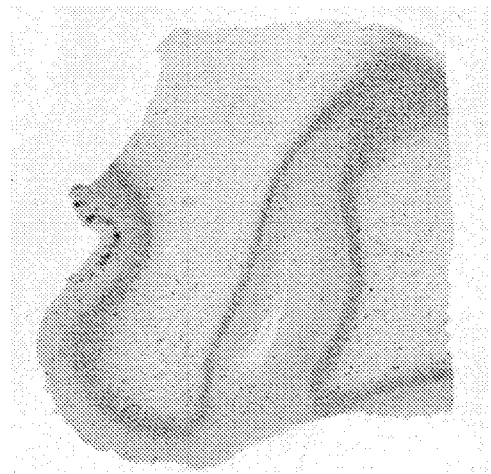
Figure 1A
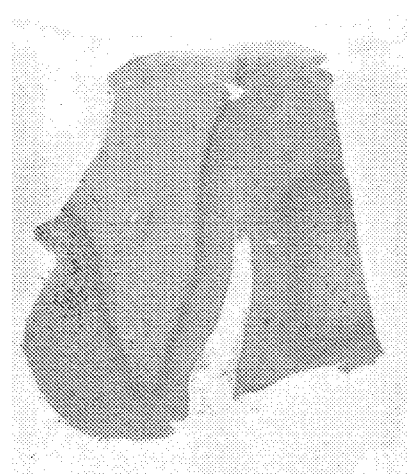
Figure 1B
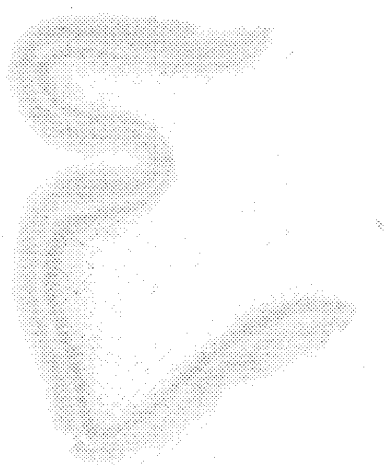
Figure 1C
Figure 1D
Figure 1A-1D

2-PHENYL OR 2-HETARYL IMIDAZOL[1,2-A]PYRIDINE DERIVATIVES

CROSS REFERENCE TO RELATED APPLICATIONS

This application is a continuation of International Application No. PCT/EP2014/058415 having an international filing date of Apr. 25, 2014, the entire contents of which are incorporated herein by reference, and which claims benefit under 35 U.S.C. § 119 to European Patent Application No. 13165676.1 filed Apr. 29, 2013.

SUMMARY OF THE INVENTION

The invention relates to novel 2-phenyl or 2-hetaryl imidazol[1,2-a]pyridine derivatives of formula (I) or (II)

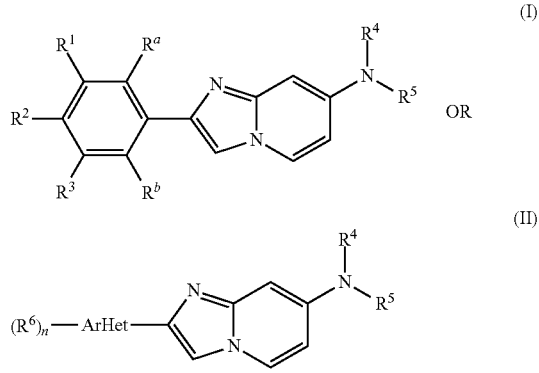

wherein
$R^1$ is hydrogen, lower alkyl, lower alkoxy, halogen, S-lower alkyl, lower alkoxy substituted by halogen, di-lower alkyl amino, C(O)O-lower alkyl, lower alkyl substituted by hydroxy or hydroxy;
$R^2$ is hydrogen, lower alkyl, halogen, lower alkoxy, S-lower alkyl, lower alkoxy substituted by halogen, $O(CH_2)_2$-lower alkoxy substituted by halogen, di-lower alkyl amino, alkyl amino, NH-lower alkyl substituted by halogen, N(lower alkyl)-benzyl, lower alkyl substituted by hydroxy, heterocycloalkyl optionally substituted by halogen, $CH_2$-lower alkoxy, $CH_2$-lower alkoxy substituted by halogen or hydroxy; or
$R^1$ and $R^2$ form together with the carbon atoms to which they are attached a ring containing —$OCH_2CH_2O$—, $OCH_2O$—, $OCH_2CH_2CH_2O$— or —$NHC(O)CH_2O$—;
$R^3$ is hydrogen or lower alkoxy;
$R^4$ is hydrogen or lower alkyl;
$R^5$ is lower alkyl, cycloalkyl, lower alkyl substituted by hydroxy or lower alkyl substituted by halogen; or
$R^4$ and $R^5$ form together with the nitrogen atom to which they are attached a ring containing —$CH_2CH_2CHRCH_2CH_2$—, —$CH_2CHRCH_2CH_2$—, —$CH_2CH_2OCH_2CH_2$—$CH_2CH_2NR'CH_2CH_2$—, $CH_2CHR$— or —$CH_2CH_2CH_2$—; wherein
R is hydrogen, halogen, lower alkyl, lower alkoxy or lower alkyl substituted by halogen;
R' is lower alkyl substituted by halogen;
$R^a$ is hydrogen or $^3H$;
$R^b$ is hydrogen, hydroxy or $^3H$;
$R^6$ is hydrogen, halogen or lower alkyl;
HetAr is selected from the group consisting of thiophenyl, furanyl, thiozolyl, benzofuranyl, pyrazolyl, benzoimidazolyl or pyridinyl;
n is 1 or 2;
or to a pharmaceutically acceptable acid addition salt, to a racemic mixture or to its corresponding enantiomer and/or optical isomers thereof.

Similar compounds are described for example in US 2011/0071128 as intermediates for the preparation of PDE10A inhibitors for use in the treatment of central nervous system diseases and in European Journal of Medicinal Chemistry, 2012, 52, 137-150 as antitumor agents.

It has been shown that the present compounds may be used for binding and imaging tau aggregates and related beta-sheet aggregates including besides others beta-amyloid aggregates or alpha-synuclein aggregates, especially for use in binding and imaging tau aggregates in Alzheimer patients.

Alzheimer's disease (AD) is a progressive neurodegenerative disorder characterized by cognitive decline, irreversible memory loss, disorientation and language impairment (Arch. Neurol. 1985, 42(11), 1097-1105). Postmortem examination of AD brain sections reveals abundant senile plaques (SPs), composed of beta amyloid (Aβ) peptides, and numerous neurofibrillary tangles (NFTs) formed by filaments of hyperphosphorylated tau protein.

Tau belongs to the family of microtubule-associated proteins and is mainly expressed in neurons where it plays an important role in the assembly of tubulin monomers into microtubules to constitute the neuronal microtubule network as tracks for axonal transport (Brain Res. Rev. 2000, 33(1), 95-130). Tau is translated from a single gene located on chromosome 17 and the expression is developmentally regulated by an alternative splicing mechanism generating six different isoforms in the human adult brain that can be distinguished by their number of binding domains. The underlying mechanisms leading to tau hyperphosphorylation, misfolding and aggregation are not well understood, but the deposition of tau aggregates follows a stereotyped spatiotemporal pathway both at the intracellular levels as well as on the level of brain topography.

The recent discovery of tau gene mutations leading to frontotemporal dementia (FTD) with parkinsonism linked to chromosome 17 has reinforced the predominant role attributed to tau in the pathogenesis of neurodegenerative disorders and underlined the fact that distinct sets of tau isoforms expressed in different neuronal populations could lead to different pathologies (Biochim. Biophys. Acta 2005, 1739 (2) 240-250). Neurodegenerative diseases characterized by pathological tau accumulation are termed 'tauopathies' (Ann. Rev. Neurosci. 2001, 24, 1121-1159). Besides AD and FTD, other tauopathies include progressive supranuclear palsy (PSP), tangle-predominant dementia, Pick's disease, frontotemporal lobar degeneration (FTLD), Down's syndrome and others.

A direct correlation has been established between the progressive involvement of neocortical areas and the increasing severity of dementia, suggesting that pathological tau aggregates such as NFTs are a reliable marker of the neurodegenerative process. The degree of NFT involvement in AD is defined by Braak stages (Acta Neuropathol. 1991, 82, 239-259). Braak stages I and II are defined when NFT involvement is confined mainly to the transentorhinal region of the brain, stages III and IV are diagnosed when limbic regions such as the hippocampus are involved, and stages V and VI when extensive neocortical involvement is found.

Presently, detection of tau aggregates is only possible by histological analysis of biopsy or autopsy materials. In vivo imaging of tau pathology would provide novel insights into deposition of tau aggregates in the human brain and allow to non-invasively examine the degree of tau pathology, quantify changes in tau deposition over time, assess its correlation with cognition and analyze the efficacy of an anti-tau therapy. Potential ligands for detecting tau aggregates in the living brain must cross the blood-brain barrier and possess high affinity and specificity for tau aggregates. To this end, successful neuroimaging radiotracers must have appropriate lipophilicity (log D 1-3) and low molecular weight (<450), show rapid clearance from blood and low non-specific binding.

The object of the present application is to find an imaging tool which will improve diagnosis by identifying potential patients with excess of tau aggregates in the brain, which may be likely to develop Alzheimer's disease. It will also be useful to monitor the progression of the disease. When an anti-tau aggregate drug become available, imaging tau tangles in the brain may provide an essential tool for monitoring treatment.

A further object of the present invention is a method of imaging tau-aggregate deposits, comprising
  introducing into a mammal a detectable quantity of a composition
  allowing sufficient time for the compound of formula I or II to be associated with tau-aggregate deposits, and
  detecting the compound associated with one or more tau-aggregate deposits.

A further object of the present invention is a pharmaceutical composition, containing compounds of formula I or II and pharmaceutical acceptable carriers, which may be used for identifying potential patients.

BRIEF DESCRIPTION OF DRAWINGS

FIG. 1A-1D—shows the autoradiograms of example 62 (1A), example 64 (1B), example 61 (1C) and example 63 (1D) incubated with human cortical brain sections obtained from a Braak V staged AD patient. The radioligand concentrations were 1.8, 2.8, 3.7 and 2.7 nM, respectively. All radioligands show punctate staining of tau aggregates in a layered distribution pattern and a varying degree of non-specific binding in white matter.

DETAILED DESCRIPTION OF THE INVENTION

Figure 2:
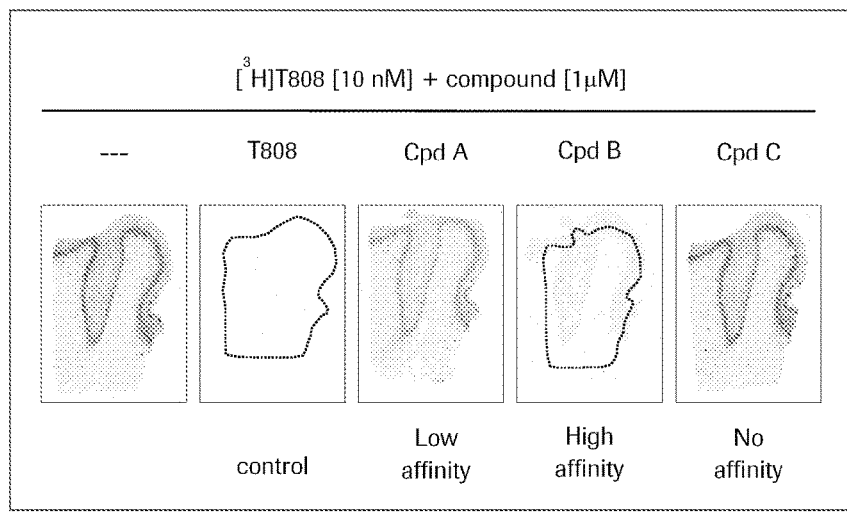
FIG. 2—shows the autoradiogram from TAU radioligand in vitro displacement assay to assess the affinity of compounds for native tau aggregates. The compounds are co-incubated with the well-established tau specific radioligand [$^3$H]T808 and the compound's displacement potency of [$^3$H]T808 binding is determined by in vitro autoradiography using human Alzheimer's disease (AD) brain sections (see illustration below).

The following definitions of the general terms used in the present description apply irrespective of whether the terms in question appear alone or in combination.

As used herein, the term "lower alkyl" denotes a saturated, i.e. aliphatic hydrocarbon group including a straight or branched carbon chain with 1-7 carbon atoms. Examples for "alkyl" are methyl, ethyl, n-propyl, and isopropyl.

The term "cycloalkyl" denotes a non aromatic hydrocarbon ring, containing from 3 to 6 carbon atoms.

The term "alkoxy" denotes a group —O—R' wherein R' is lower alkyl as defined above.

The term "halogen" denotes chlorine, bromine, fluorine or iodine.

The term "lower alkyl substituted by halogen" denotes an alkyl group as defined above, wherein at least one hydrogen atom is replaced by a halogen atom.

The term "lower alkyl substituted by hydroxy" denotes an alkyl group as defined above, wherein at least one hydrogen atom is replaced by a hydroxy group.

The term "lower alkoxy substituted by halogen" denotes an alkoxy group as defined above, wherein at least one hydrogen atom is replaced by a halogen atom.

The term heterocycloalkyl denotes a saturated ring, containing one or more heteroatoms selected from N, O or S, which rings are selected from pyrrolidinyl, piperidinyl, piperazinyl or morpholinyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The phrase "a racemic mixture or its corresponding enantiomer and/or optical isomers thereof" includes pure enantiomers or diastereomers or a mixture containing enantiomers or diastereomers in any proportions.

It has been found that the compounds of formula I or II may be used for binding and imaging tau aggregates and related b-sheet aggregates including besides others beta-amyloid aggregates or alpha-synuclein aggregates.

One object of the present invention is compounds of formula

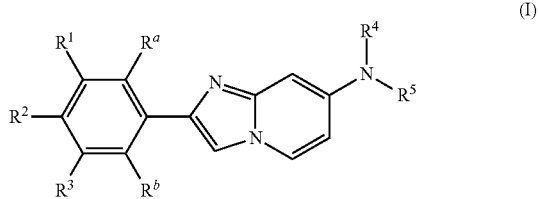

(I)

wherein
$R^1$ is hydrogen, lower alkyl, lower alkoxy, halogen, S-lower alkyl, lower alkoxy substituted by halogen, di-lower alkyl amino, C(O)O-lower alkyl, lower alkyl substituted by hydroxy or hydroxy;
$R^2$ is hydrogen, lower alkyl, halogen, lower alkoxy, S-lower alkyl, lower alkoxy substituted by halogen, O(CH$_2$)$_2$-lower alkoxy substituted by halogen, di-lower alkyl amino, alkyl amino, NH-lower alkyl substituted by halogen, N(lower alkyl)-benzyl, lower alkyl substituted by hydroxy, heterocycloalkyl optionally substituted by halogen, CH$_2$-lower alkoxy, CH-lower alkoxy substituted by halogen or hydroxy; or
$R^1$ and $R^2$ form together with the carbon atoms to which they are attached a ring containing —OCH$_2$CH$_2$O—, OCH$_2$O—, OCH$_2$CH$_2$CH$_2$O— or —NHC(O)CH$_2$O—;
$R^3$ is hydrogen or lower alkoxy;
$R^4$ is hydrogen or lower alkyl;
$R^5$ is lower alkyl, cycloalkyl, lower alkyl substituted by hydroxy or lower alkyl substituted by halogen; or
$R^4$ and $R^5$ form together with the nitrogen atom to which they are attached a ring containing —CH$_2$CH$_2$CHRCH$_2$CH$_2$—, —CH$_2$CHRCH$_2$CH$_2$—, —CH₂CH₂OCH₂CH₂—CH₂CH₂NR'CH₂CH₂—,
CH₂CHR— or —CH₂CH₂CH₂—; wherein
R is hydrogen, halogen, lower alkyl, lower alkoxy or lower alkyl substituted by halogen;
R' is lower alkyl substituted by halogen;
$R^a$ is hydrogen or $^3H$;
$R^b$ is hydrogen, hydroxy or $^3H$;
or a pharmaceutically acceptable acid addition salt, a racemic mixture or its corresponding enantiomer and/or optical isomers thereof.

One further object of the present invention are compounds of formula

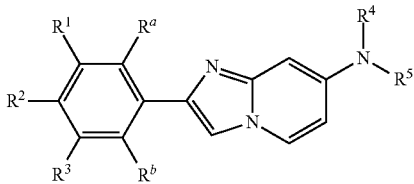

(IA)

wherein
$R^1$ is hydrogen, lower alkyl, lower alkoxy, halogen, S-lower alkyl, lower alkoxy substituted by halogen, di-lower alkyl amino, C(O)O-lower alkyl, lower alkyl substituted by hydroxy or hydroxy;
$R^2$ is hydrogen, lower alkyl, halogen, lower alkoxy, S-lower alkyl, lower alkoxy substituted by halogen, O(CH₂)₂-lower alkoxy substituted by halogen, di-lower alkyl amino, alkyl amino, NH-lower alkyl substituted by halogen, N(lower alkyl)-benzyl, lower alkyl substituted by hydroxy, heterocycloalkyl optionally substituted by halogen, CH₂-lower alkoxy, CH-lower alkoxy substituted by halogen or hydroxy; or
$R^3$ is hydrogen or lower alkoxy;
$R^4$ is hydrogen or lower alkyl;
$R^5$ is lower alkyl, cycloalkyl, lower alkyl substituted by hydroxy or lower alkyl substituted by halogen; or
$R^a$ is hydrogen or $^3H$;
$R^b$ is hydrogen, hydroxy or $^3H$;
or a pharmaceutically acceptable acid addition salt, a racemic mixture or its corresponding enantiomer and/or optical isomers thereof, for example the following compounds:
N-(2-fluoroethyl)-2-phenylimidazo[1,2-a]pyridin-7-amine
N-(2-fluoroethyl)-N-methyl-2-phenylimidazo[1,2-a]pyridin-7-amine
N,N-dimethyl-2-phenylimidazo[1,2-a]pyridin-7-amine
N-methyl-2-phenylimidazo[1,2-a]pyridin-7-amine
[2-(4-dimethylamino-phenyl)-imidazo[1,2-a]pyridin-7-yl]-dimethyl-amine
(2-[4-(2-fluoro-ethoxy)-phenyl]-imidazo[1,2-a]pyridin-7-yl}-dimethyl-amine
[2-(4-fluoromethoxy-phenyl)-imidazo[1,2-a]pyridin-7-yl]-dimethyl-amine
[2-(4-methoxy-phenyl)-imidazo[1,2-a]pyridin-7-yl]-dimethyl-amine
N-methyl-2-m-tolylimidazo[1,2-a]pyridin-7-amine
N,N-dimethyl-(2-m-tolyl-imidazo[1,2-a]pyridin-7-yl)-amine
N,N-dimethyl-(2-p-tolyl-imidazo[1,2-a]pyridin-7-yl)-amine
N-methyl-(2-p-tolyl-imidazo[1,2-a]pyridin-7-yl)-amine
N-(2-fluoroethyl)-N-methyl-(2-p-tolyl-imidazo[1,2-a]pyridin-7-yl)-amine
2-(4-(dimethylamino)phenyl)-N-(2-fluoroethyl)-N-methyl-imidazo[1,2-a]pyridin-7-amine
[2-(3-methoxy-phenyl)-imidazo[1,2-a]pyridin-7-yl]-dimethyl-amine
(2-fluoro-ethyl)-methyl-(2-m-tolyl-imidazo[1,2-a]pyridin-7-yl)-amine
[2-(3-methoxy-phenyl)-imidazo[1,2-a]pyridin-7-yl]-methyl-amine
[2-(4-fluoromethoxy-phenyl)-imidazo[1,2-a]pyridin-7-yl]-methyl-amine
(2-fluoro-ethyl)-(2-p-tolyl-imidazo[1,2-a]pyridin-7-yl)-amine
(2-fluoro-ethyl)-(2-m-tolyl-imidazo[1,2-a]pyridin-7-yl)-amine
(2-fluoro-ethyl)-[2-(4-fluoromethoxy-phenyl)-imidazo[1,2-a]pyridin-7-yl]-amine
[2-(3,4-dimethyl-phenyl)-imidazo[1,2-a]pyridin-7-yl]-dimethyl-amine
[2-(3,4-dimethyl-phenyl)-imidazo[1,2-a]pyridin-7-yl]-methyl-amine
[$^3H$]-[2-(4-fluoromethoxy-phenyl)-imidazo[1,2-a]pyridin-7-yl]-methyl-amine
[$^3H$]—N-methyl-2-phenyl-imidazo[1,2-a]pyridin-7-amine
[$^3H$]—N-(2-fluoroethyl)-2-phenyl-imidazo[1,2-a]pyridin-7-amine
[$^3H$]—N-methyl-(2-p-tolyl-imidazo[1,2-a]pyridin-7-yl)-amine
(2-fluoro-ethyl)-[2-(4-methoxy-phenyl)-imidazo[1,2-a]pyridin-7-yl]-methyl-amine
[2-(3,4-dimethoxy-phenyl)-imidazo[1,2-a]pyridin-7-yl]-methyl-amine
cyclopropyl-[2-(4-methoxy-phenyl)-imidazo[1,2-a]pyridin-7-yl]-amine
methyl-[2-(4-methylsulfanyl-phenyl)-imidazo[1,2-a]pyridin-7-yl]-amine
[2-(3,4-dimethyl-phenyl)-imidazo[1,2-a]pyridin-7-yl]-(2-fluoro-ethyl)-amine
[2-(3,4-dimethoxy-phenyl)-imidazo[1,2-a]pyridin-7-yl]-(2-fluoro-ethyl)-amine
[2-(4-methoxy-phenyl)-imidazo[1,2-a]pyridin-7-yl]-methyl-amine
(2-fluoro-ethyl)-[2-(4-methoxy-phenyl)-imidazo[1,2-a]pyridin-7-yl]-amine
(2-fluoro-ethyl)-[2-(3-methoxy-phenyl)-imidazo[1,2-a]pyridin-7-yl]-amine
[2-(3-fluoromethoxy-phenyl)-imidazo[1,2-a]pyridin-7-yl]-dimethyl-amine
(2-fluoro-ethyl)-[2-(4-methylsulfanyl-phenyl)-imidazo[1,2-a]pyridin-7-yl]-amine
cyclopropyl-[2-(4-fluoromethoxy-phenyl)-imidazo[1,2-a]pyridin-7-yl]-amine
2-methoxy-4-(7-methylamino-imidazo[1,2-a]pyridin-2-yl)-phenol
3-(7-dimethylamino-imidazo[1,2-a]pyridin-2-yl)-phenol
[4-[7-(methylamino)imidazo[1,2-a]pyridin-2-yl]phenyl]methanol
[4-[7-(dimethylamino)imidazo[1,2-a]pyridin-2-yl]phenyl]methanol
2-(3,5-dimethoxyphenyl)-N-methylimidazo[1,2-a]pyridin-7-amine
N-[2-(4-ethoxy-phenyl)-imidazo[1,2-a]pyridin-7-yl]-methyl-amine
methyl-[2-(4-pyrrolidin-1-yl-phenyl)-imidazo[1,2-a]pyridin-7-yl]-amine
N-[2-(3-fluoro-4-methoxy-phenyl)-imidazo[1,2-a]pyridin-7-yl]-methyl-amine N-[2-(4-diethylamino-phenyl)-imidazo[1,2-a]pyridin-7-yl]-methyl-amine
N-[2-(4-ethyl-phenyl)-imidazo[1,2-a]pyridin-7-yl]-methyl-amine
2-[4-(methoxymethyl)phenyl]-N,N-dimethyl-imidazo[1,2-a]pyridin-7-amine
methyl-[2-(4-morpholin-4-yl-phenyl)-imidazo[1,2-a]pyridin-7-yl]-amine
2-[4-(2-fluoroethoxymethyl)phenyl]-N,N-dimethyl-imidazo[1,2-a]pyridin-7-amine
2-(3-methoxy-4-methylphenyl)-N-methylimidazo[1,2-a]pyridin-7-amine
2-[4-(2-fluoroethoxy)phenyl]-N-methylimidazo[1,2-a]pyridin-7-amine
2-(4-(benzyl(methyl)amino)phenyl)-N-methylimidazo[1,2-a]pyridin-7-amine
N-[2-(4-difluoromethoxy-phenyl)-imidazo[1,2-a]pyridin-7-yl]-methyl-amine
N-[2-(4-bromo-phenyl)-imidazo[1,2-a]pyridin-7-yl]-methyl-amine
methyl-[2-(4-piperidin-1-yl-phenyl)-imidazo[1,2-a]pyridin-7-yl]-amine
2-(7-methylamino-imidazo[1,2-a]pyridin-2-yl)-phenol
methyl 3-[7-(methylamino)imidazo[1,2-a]pyridin-2-yl]benzoate
[3-[7-(methylamino)imidazo[1,2-a]pyridin-2-yl]phenyl]methanol
N-cyclopropyl-2-[4-(2-fluoroethoxy)phenyl]imidazo[1,2-a]pyridin-7-amine
7-(azetidin-1-yl)-2-[4-(3-fluoropropoxy)phenyl]imidazo[1,2-a]pyridine
4-methyl-2-(7-methylamino-imidazo[1,2-a]pyridin-2-yl)-phenol
2-[3-(methoxymethyl)phenyl]-N-methyl-imidazo[1,2-a]_yridine-7-amine
2-(4-(2-fluoroethylamino)phenyl)-N-methylimidazo[1,2-a]pyridin-7-amine
N-(3-fluoropropyl)-2-(4-methoxyphenyl)imidazo[1,2-a]pyridin-7-amine
2-(3-(fluoromethoxy)phenyl)-N-methylimidazo[1,2-a]pyridin-7-amine
2-(2-(4-methoxyphenyl)imidazo[1,2-a]pyridin-7-ylamino)propan-1-ol
N-(2-fluoroethyl)-2-(3-methoxy-4-methylphenyl)imidazo[1,2-a]pyridin-7-amine
N-methyl-2-(3-(methylthio)phenyl)imidazo[1,2-a]pyridin-7-amine
2-(3-(2-fluoroethoxy)phenyl)-N-methylimidazo[1,2-a]pyridin-7-amine
2-(3-(3-fluoropropoxy)phenyl)-N-methylimidazo[1,2-a]pyridin-7-amine
2-(4-(4-fluoropiperidin-1-yl)phenyl)-N-methylimidazo[1,2-a]pyridin-7-amine
4-(7-(2-fluoroethylamino)imidazo[1,2-a]pyridin-2-yl)-2-methoxyphenol
4-(7-(2-fluoroethylamino)imidazo[1,2-a]pyridin-2-yl)phenol
3-(7-(2-fluoroethylamino)imidazo[1,2-a]pyridin-2-yl)phenol
N-(2-fluoroethyl)-2-(4-morpholin-4-ylphenyl)imidazo[1,2-a]pyridin-7-amine or
N-cyclopropyl-2-[4-(3-fluoropropoxy)phenyl]imidazo[1,2-a]pyridin-7-amine.

One object of the present invention is further compounds of formula

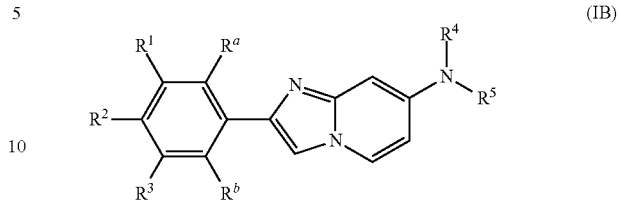

(IB)

wherein
R¹ and R² form together with the carbon atoms to which they are attached a ring containing —OCH₂CH₂O—, OCH₂O—, OCH₂CH₂CH₂O— or —NHC(O)CH₂O—;
R³ is hydrogen or lower alkoxy;
R⁴ is hydrogen or lower alkyl;
R⁵ is lower alkyl, cycloalkyl, lower alkyl substituted by hydroxy or lower alkyl substituted by halogen, or Rᵃ is hydrogen or ³H;
Rᵇ is hydrogen, hydroxy or ³H;
or a pharmaceutically acceptable acid addition salt, a racemic mixture or its corresponding enantiomer and/or optical isomers thereof, for example the following compounds:
[2-(2,3-dihydro-benzo[1,4]dioxin-6-yl)-imidazo[1,2-a]pyridin-7-yl]-methyl-amine
[2-(2,3-dihydro-benzo[1,4]dioxin-6-yl)-imidazo[1,2-a]pyridin-7-yl]-dimethyl-amine
[2-(2,3-dihydro-benzo[1,4]dioxin-6-yl)-imidazo[1,2-a]pyridin-7-yl]-(2-fluoro-ethyl)-methyl-amine
(2-benzo[1,3]dioxol-5-yl-imidazo[1,2-a]pyridin-7-yl)-methyl-amine
(2-benzo[1,3]dioxol-5-yl-imidazo[1,2-a]pyridin-7-yl)-dimethyl-amine
(2-benzo[1,3]dioxol-5-yl-imidazo[1,2-a]pyridin-7-yl)-(2-fluoro-ethyl)-methyl-amine
(2-benzo[1,3]dioxol-5-yl-imidazo[1,2-a]pyridin-7-yl)-(2-fluoro-ethyl)-amine
N-[2-(3,4-dihydro-2H-benzo[b][1,4]dioxepin-7-yl)-imidazo[1,2-a]pyridin-7-yl]-methyl-amine
6-(7-methylamino-imidazo[1,2-a]pyridin-2-yl)-4H-benzo[1,4]oxazin-3-one or
2-(2,3-dihydrobenzo[b][1,4]dioxin-6-yl)-N-(2-fluoroethyl)imidazo[1,2-a]pyridin-7-amine.

One object of the present invention are compounds of formula

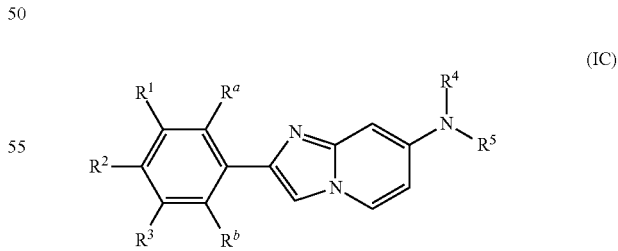

(IC)

wherein
R¹ and R² form together with the carbon atoms to which they are attached a ring containing —OCH₂CH₂O—, OCH₂O—, OCH₂CH₂CH₂O— or —NHC(O)CH₂O—;
R³ is hydrogen or lower alkoxy;
R⁴ and R⁵ form together with the nitrogen atom to which they are attached a ring containing —CH₂CH₂CHRCH₂CH₂—, —CH₂CHRCH₂CH₂—, —CH₂CH₂OCH₂CH₂—CH₂CH₂NR'CH₂CH₂—, CH₂CHR— or —CH₂CH₂CH₂—; wherein
- R is hydrogen, halogen, lower alkyl, lower alkoxy or lower alkyl substituted by halogen;
- R' is lower alkyl substituted by halogen;
- $R^a$ is hydrogen or $^3H$;
- $R^b$ is hydrogen, hydroxy or $^3H$;

or a pharmaceutically acceptable acid addition salt, a racemic mixture or its corresponding enantiomer and/or optical isomers thereof for example the following compounds:

2-benzo[1,3]dioxol-5-yl-7-[4-(2-fluoro-ethyl)-piperazin-1-yl]-imidazo[1,2-a]pyridine
2-(2,3-dihydro-benzo[1,4]dioxin-6-yl)-7-[4-(2-fluoro-ethyl)-piperidin-1-yl]-imidazo[1,2-a]pyridine
2-benzo[1,3]dioxol-5-yl-7-(4-fluoro-piperidin-1-yl)-imidazo[1,2-a]pyridine or
2-(2,3-dihydro-benzo[1,4]dioxin-6-yl)-7-(4-fluoro-piperidin-1-yl)-imidazo[1,2-a]pyridine.

One object of the present invention are further compounds of formula

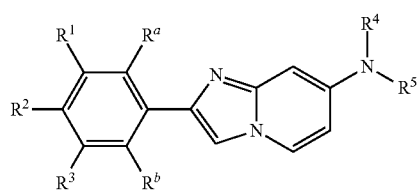

(ID)

wherein
- $R^1$ is hydrogen, lower alkyl, lower alkoxy, halogen, S-lower alkyl, lower alkoxy substituted by halogen, di-lower alkyl amino, C(O)O-lower alkyl, lower alkyl substituted by hydroxy or hydroxy;
- $R^2$ is hydrogen, lower alkyl, halogen, lower alkoxy, S-lower alkyl, lower alkoxy substituted by halogen, O(CH₂)₂-lower alkoxy substituted by halogen, di-lower alkyl amino, alkyl amino, NH-lower alkyl substituted by halogen, N(lower alkyl)-benzyl, lower alkyl substituted by hydroxy, heterocycloalkyl optionally substituted by halogen, CH₂-lower alkoxy, CH-lower alkoxy substituted by halogen or hydroxy; or
- $R^3$ is hydrogen or lower alkoxy;
- $R^4$ is hydrogen or lower alkyl;
- $R^5$ is lower alkyl, cycloalkyl, lower alkyl substituted by hydroxy or lower alkyl substituted by halogen, or
- $R^4$ and $R^5$ form together with the nitrogen atom to which they are attached a ring containing —CH₂CH₂CHRCH₂CH₂—, —CH₂CHRCH₂CH₂—, —CH₂CH₂OCH₂CH₂—CH₂CH₂NR'CH₂CH₂—, CH₂CHR— or —CH₂CH₂CH₂—; wherein
  - R is hydrogen, halogen, lower alkyl, lower alkoxy or lower alkyl substituted by halogen;
  - R' is lower alkyl substituted by halogen;
- $R^a$ is hydrogen or $^3H$;
- $R^b$ is hydrogen, hydroxy or $^3H$;

or a pharmaceutically acceptable acid addition salt, a racemic mixture or its corresponding enantiomer and/or optical isomers thereof for example the following compounds:

7-(4-fluoropiperidin-1-yl)-2-phenylimidazo[1,2-a]pyridine
(S)-7-(3-fluoropyrrolidin-1-yl)-2-(4-methoxyphenyl)imidazo[1,2-a]pyridine
(R)-7-(3-fluoropyrrolidin-1-yl)-2-(4-methoxyphenyl)imidazo[1,2-a]pyridine
2-(3-methoxy-phenyl)-7-piperidin-1-yl-imidazo[1,2-a]pyridine
2-(3-methoxy-phenyl)-7-pyrrolidin-1-yl-imidazo[1,2-a]pyridine
2-(3-methoxy-phenyl)-7-morphonlin-1-yl-imidazo[1,2-a]pyridine
2-(4-methoxy-phenyl)-7-pyrrolidin-1-yl-imidazo[1,2-a]pyridine
2-(4-methoxy-phenyl)-7-piperidin-1-yl-imidazo[1,2-a]pyridine
2-(4-methoxy-phenyl)-7-morphonlin-1-yl-imidazo[1,2-a]pyridine
7-(4-fluoro-piperidin-1-yl)-2-(4-methoxy-phenyl)-imidazo[1,2-a]pyridine
7-[4-(2-fluoro-ethyl)-piperazin-1-yl]-2-(4-methoxy-phenyl)-imidazo[1,2-a]pyridine
7-azetidin-1-yl-2-(4-methoxy-phenyl)-imidazo[1,2-a]pyridine
(S)-7-(3-fluoropyrrolidin-1-yl)-2-phenyl-imidazo[1,2-a]pyridine
7-morpholin-4-yl-2-m-tolyl-imidazo[1,2-a]pyridine
7-morpholin-4-yl-2-p-tolyl-imidazo[1,2-a]pyridine
4-(7-azetidin-1-yl-imidazo[1,2-a]pyridin-2-yl)-phenol
{4-[7-(4-fluoro-piperidin-1-yl)-imidazo[1,2-a]pyridin-2-yl]-phenyl}-dimethyl-amine
7-((R)-3-fluoro-pyrrolidin-1-yl)-2-phenyl-imidazo[1,2-a]pyridine
7-((R)-3-methoxy-pyrrolidin-1-yl)-2-phenyl-imidazo[1,2-a]pyridine
7-((S)-3-methoxy-pyrrolidin-1-yl)-2-m-tolyl-imidazo[1,2-a]pyridine
2-(4-fluoromethoxy-phenyl)-7-morpholin-4-yl-imidazo[1,2-a]pyridine
7-azetidin-1-yl-2-p-tolyl-imidazo[1,2-a]pyridine
7-azetidin-1-yl-2-m-tolyl-imidazo[1,2-a]pyridine
7-((R)-3-methoxy-pyrrolidin-1-yl)-2-p-tolyl-imidazo[1,2-a]pyridine
7-(4-fluoro-piperidin-1-yl)-2-p-tolyl-imidazo[1,2-a]pyridine
7-[4-(2-fluoro-ethyl)-piperidin-1-yl]-2-phenyl-imidazo[1,2-a]pyridine
7-((S)-3-methoxy-pyrrolidin-1-yl)-2-phenyl-imidazo[1,2-a]pyridine
7-(4-fluoro-piperidin-1-yl)-2-(3-methoxy-phenyl)-imidazo[1,2-a]pyridine
7-(4-fluoro-piperidin-1-yl)-2-m-tolyl-imidazo[1,2-a]pyridine
7-azetidin-1-yl-2-(4-fluoromethoxy-phenyl)-imidazo[1,2-a]pyridine
7-[4-(2-fluoro-ethyl)-piperidin-1-yl]-2-(4-methoxy-phenyl)-imidazo[1,2-a]pyridine
7-[4-(2-fluoro-ethyl)-piperidin-1-yl]-2-m-tolyl-imidazo[1,2-a]pyridine
7-((R)-3-methoxy-pyrrolidin-1-yl)-2-m-tolyl-imidazo[1,2-a]pyridine
7-[4-(2-fluoro-ethyl)-piperidin-1-yl]-2-p-tolyl-imidazo[1,2-a]pyridine
7-((S)-3-methoxy-pyrrolidin-1-yl)-2-p-tolyl-imidazo[1,2-a]pyridine
7-(azetidin-1-yl)-2-(3-methoxyphenyl)imidazo[1,2-a]pyridine
7-(azetidin-1-yl)-2-[4-(2-fluoroethoxy)phenyl]imidazo[1,2-a]pyridine
7-(azetidin-1-yl)-2-[3-(fluoromethoxy)phenyl]imidazo[1,2-a]pyridine 2-(4-methoxyphenyl)-7-(2-methylaziridin-1-yl)imidazo[1,2-a]pyridine
7-(azetidin-1-yl)-2-(3-(2-fluoroethoxy)phenyl)imidazo[1,2-a]pyridine or
7-(azetidin-1-yl)-2-(4-(2-(2-fluoroethoxy)ethoxy)phenyl)imidazo[1,2-a]pyridine.

One further object of the present invention is a compound of formula II

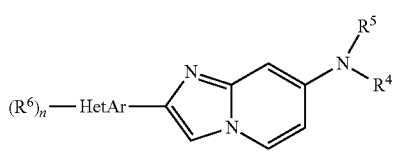
(II)

wherein
R⁴ is hydrogen or lower alkyl;
R⁵ is lower alkyl, cycloalkyl, lower alkyl substituted by hydroxy or lower alkyl substituted by halogen, or
R⁴ and R⁵ form together with the nitrogen atom to which they are attached a ring containing —CH₂CH₂CHRCH₂CH₂—, —CH₂CHRCH₂CH₂—, —CH₂CH₂OCH₂CH₂—CH₂CH₂NR'CH₂CH₂—, CH₂CHR— or —CH₂CH₂CH₂—; wherein
R is hydrogen, halogen, lower alkyl, lower alkoxy or lower alkyl substituted by halogen;
R' is lower alkyl substituted by halogen;
R⁶ is hydrogen, halogen or lower alkyl;
HetAr is selected from the group consisting of thiophenyl, furanyl, thiozolyl, benzofuranyl, pyrazolyl, benzoimidazolyl or pyridinyl;
n is 1 or 2;
or a pharmaceutically acceptable acid addition salt, a racemic mixture or its corresponding enantiomer and/or optical isomers thereof, for example the following compounds
methyl-(2-thiophen-3-yl-imidazo[1,2-a]pyridin-7-yl)-amine
N-(2-furan-2-yl-imidazo[1,2-a]pyridin-7-yl)-methyl-amine
N-(2-thiophen-2-yl-imidazo[1,2-a]pyridin-7-yl)-methyl-amine
methyl-(2-thiazol-2-yl-imidazo[1,2-a]pyridin-7-yl)-amine
N-[2-(3-bromo-thiophen-2-yl)-imidazo[1,2-a]pyridin-7-yl]-methyl-amine
N-[2-(3-chloro-thiophen-2-yl)-imidazo[1,2-a]pyridin-7-yl]-methyl-amine
methyl-[2-(5-methyl-furan-2-yl)-imidazo[1,2-a]pyridin-7-yl]-amine
N-[2-(benzofuran-2-yl)-imidazo[1,2-a]pyridin-7-yl]-methyl-amine
N-[2-(2,5-dimethyl-2H-pyrazol-3-yl)-imidazo[1,2-a]pyridin-7-yl]-methyl-amine
methyl-[2-(1-methyl-1H-benzoimidazol-2-yl)-imidazo[1,2-a]pyridin-7-yl]-amine
methyl-(2-pyridin-3-yl-imidazo[1,2-a]pyridin-7-yl)-amine
N-[2-(5-chloro-thiophen-2-yl)-imidazo[1,2-a]pyridin-7-yl]-methyl-amine
methyl-[2-(1-methyl-1H-pyrazol-4-yl)-imidazo[1,2-a]pyridin-7-yl]-amine or
N-(2-fluoroethyl)-2-(furan-2-yl)imidazo[1,2-a]pyridin-7-amine.

The compounds of formula I-P are also an embodiment of the invention.

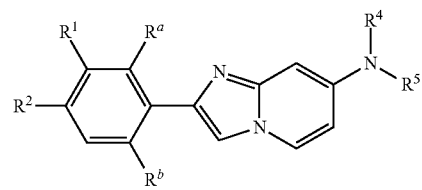
(IP)

wherein
R¹ is hydrogen, lower alkyl, lower alkoxy, S-lower alkyl, lower alkoxy substituted by halogen, di-lower alkyl amino or hydroxy;
R² is hydrogen, lower alkyl, lower alkoxy, S-lower alkyl, lower alkoxy substituted by halogen, di-lower alkyl amino or hydroxy; or
R¹ and R² form together with the carbon atoms to which they are attached a ring containing —OCH₂CH₂O— or OCH₂O—;
R³ is hydrogen or lower alkyl;
R⁴ is lower alkyl, cycloalkyl or lower alkyl substituted by halogen; or
R³ and R⁴ form together with the nitrogen atom to which they are attached a ring containing —CH₂CH₂CHRCH₂CH₂—, —CH₂CHRCH₂CH₂—, —CH₂CH₂OCH₂CH₂—CH₂CH₂NR'CH₂CH₂— or —CH₂CH₂CH₂—; wherein
R is hydrogen, halogen, lower alkoxy or lower alkyl substituted by halogen;
R' is lower alkyl substituted by halogen;
Rᵃ is hydrogen or ³H;
Rᵇ is hydrogen or ³H;
or a pharmaceutically acceptable acid addition salt, a racemic mixture or its corresponding enantiomer and/or optical isomers thereof.

The compounds of formula I and II may be used in binding and imaging tau aggregates, beta-amyloid aggregates, alpha-synuclein aggregates or huntingtin aggregates.

The preferred use of compounds of formula I or II is the use in binding and imaging tau aggregates in Alzheimer patients.

Furthermore, the compounds of formula I or II may be used in a tau-binding study.

The compounds of formula I or II are suitable for diagnostic imaging of tau-aggregates in the brain of a mammal.

The invention is also used for diagnostic imaging of tau-aggregate deposits in the brain of a mammal. The present compounds of formula I or II

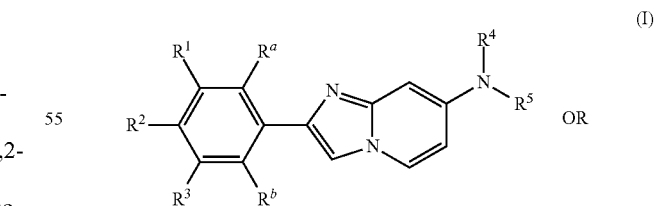
(I)

OR

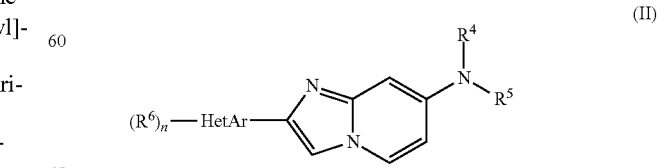
(II)

and their pharmaceutically acceptable salts can be prepared by processes described below, which process comprises a) coupling a compound of formulas 1 or 2 (X=Cl, Br)

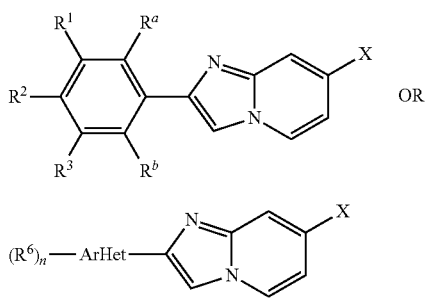
(1)

OR

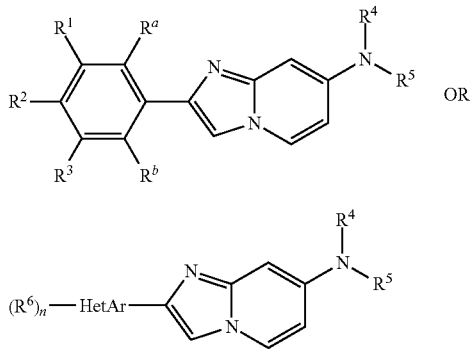
(2)

with an suitable amine HNR⁴R⁵ to afford a compound of formulas I or II (I)

(II)

wherein the substituents HetAr, R¹, R², R³, R⁴, R⁵ and R⁶ are as defined above and $R^a$ is hydrogen and $R^b$ is hydrogen or hydroxy,
and if desired, converting the compounds obtained into pharmaceutically acceptable acid addition salts; or
b) coupling a compound with formula 3

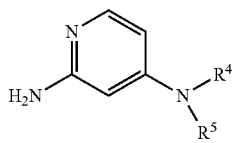
3 with a corresponding α-activated ketone of formula 4

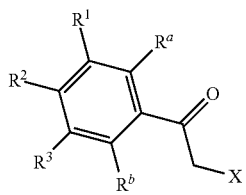
4

X = leaving group, e.g. Br to afford a compound of formula I

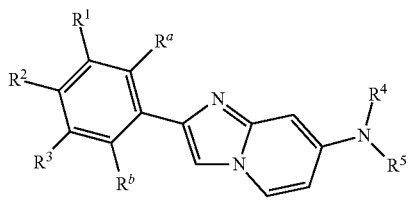
I wherein the substituents R¹, R², R³, R⁴, R⁵ and R⁶ are as defined above and $R^a$ is hydrogen and $R^b$ is hydrogen or hydroxy, and if desired, converting the compounds obtained into pharmaceutically acceptable acid addition salts, or
c) reacting a compound with formulas 5 or 6

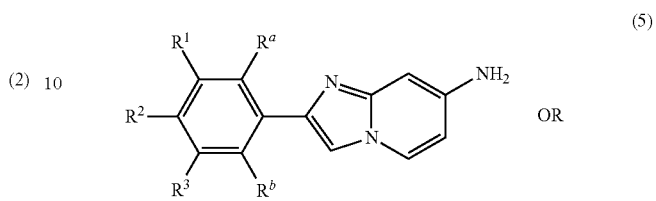
(5)

OR

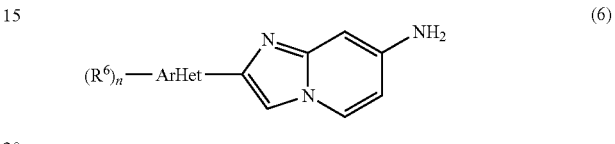
(6)

with a suitable alkylation agent to afford a compound of formula I

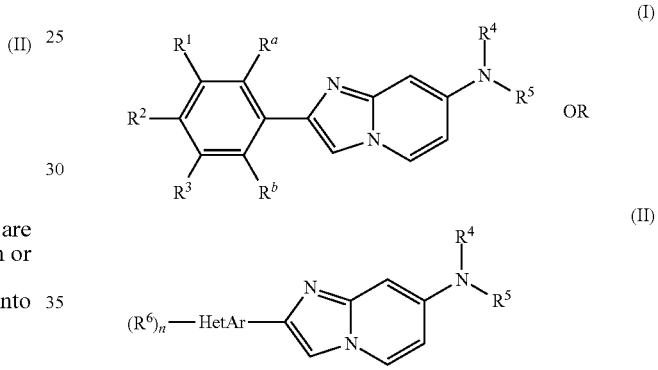
(I)

OR (II)

wherein the substituents HetAr, R¹, R², R³, R⁴, R⁵ and R⁶ are as defined above and $R^a$ is hydrogen and $R^b$ is hydrogen or hydroxy, and, if desired, converting the compounds obtained into pharmaceutically acceptable acid addition salts, or
d) reacting a compound of formula I for $R^a$ and $R^b$ being hydrogen to a compound of formula IA.

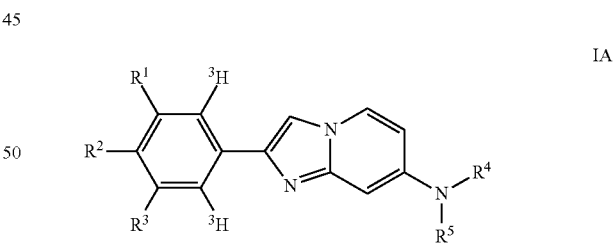
IA with tritium gas in the presence of a catalyst, e.g. iridium, ruthenium, rhodium or palladium containing complexes in a suitable solvent, e.g. dichloromethane, chlorobenzene, DMF, DMSO or mixtures thereof.

The following schemes 1-3 describe the processes for the preparation of compounds of formula I or II in more detail. The starting materials are known compounds or may be prepared according to methods known in the art.

The preparation of compounds of formula I or II of the present invention may be carried out in sequential or convergent synthetic routes. The skills required for carrying out the reaction and purification of the resulting products are known to those skilled in the art. The substituents and indices used in the following description of the processes have the significance given herein before unless indicated to the contrary.

In more detail, the compounds of formula I or II can be manufactured by the methods given below, by the methods given in the examples or by analogous methods. Appropriate reaction conditions for the individual reaction steps are known to a person skilled in the art. The reaction sequence is not limited to the one displayed in schemes 1 to 3, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

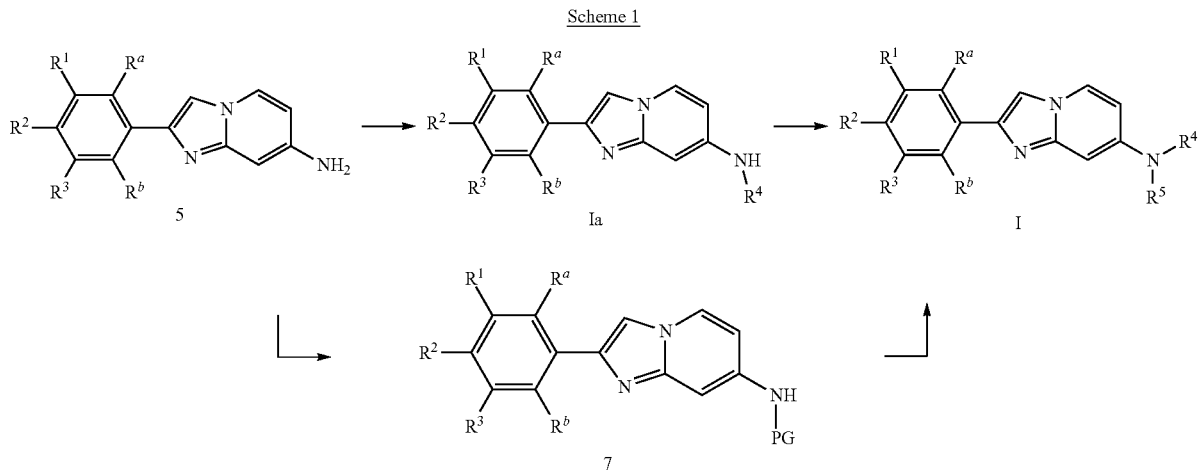

According to scheme 1, derivatives of imidazopyridine I, wherein $R^1$, $R^2$, $R^3$, $R^4$, $R^5$ and $R^6$ are as defined above and $R^a$ is hydrogen and $R^b$ is hydrogen or hydroxy, and PG is an N-protecting group, are prepared via an alkylation reaction of amine 5 with a suitable alkylation agent, e.g. methyl iodide or an alkyl halide in presence of a base, e.g. sodium hydride in a suitable solvent, e.g. DCM, at elevated or ambient temperature. Alternatively, amine 5 is first converted into a protected amine 7 via reaction with a suitable reagent, e.g. di-tert-butyldicarbonate, in a suitable solvent, followed by an alkylation reaction with a suitable alkylation agent, e.g. methyl iodide or an alkyl halide in presence of a base, e.g. sodium hydride in a suitable solvent, e.g. DCM, at elevated or ambient temperature. Deprotection of 7 is then leading to imidazopyridine I.

The same procedure may be used to obtain compounds of formula II, starting from compounds of formula 6 as described in process variant c).

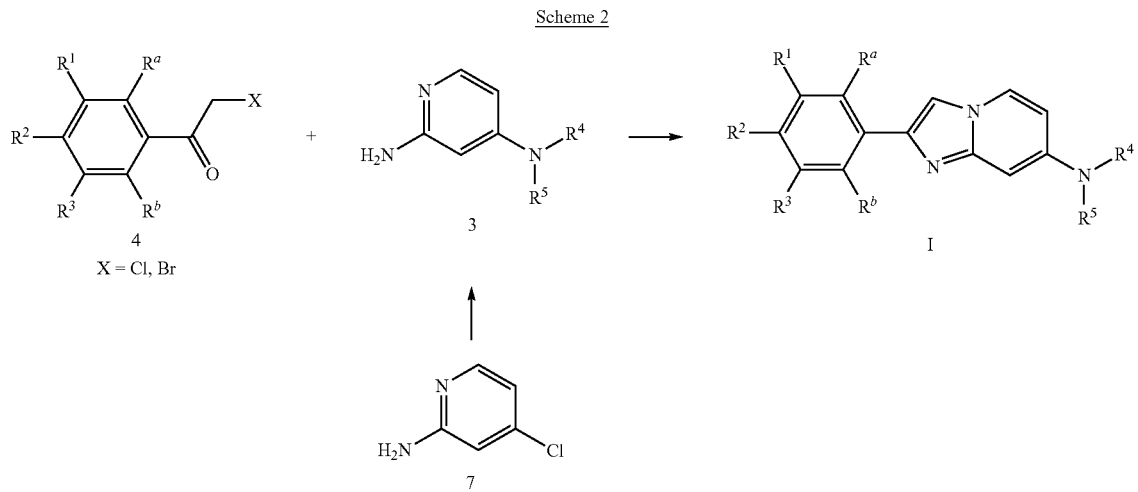

wherein $R^1$, $R^2$, $R^3$, $R^4$, $R^5$ and $R^6$ are as defined above and $R^a$ is hydrogen and $R^b$ is hydrogen or hydroxy and X=Br.

According to scheme 2, an activated ketone 4 is reacted with amino-pyridine 3 in a suitable solvent, e.g. acetone or ethanol, at elevated temperature in an oil-bath or in a microwave to afford derivatives of compound I. Amino-pyridine 3 can be synthesized starting from chloro-pyridine 7 by heating with an amine $HNR^4R^5$ and a suitable base, e.g. potassium carbonate or cesium carbonate, in a suitable solvent, e.g. sulfolane or NMP, at elevated temperature or by heating with an amine $HNR^4R^5$ in water at elevated temperature.

Scheme 3

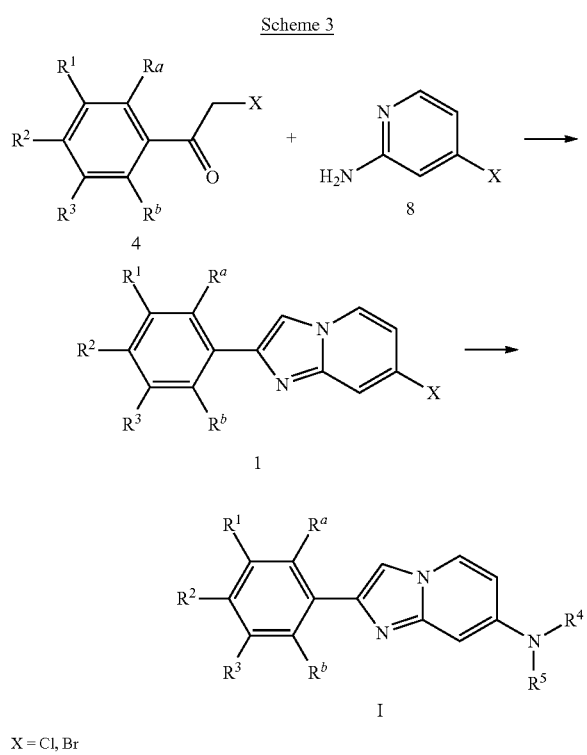

X = Cl, Br wherein $R^1$, $R^2$, $R^3$, $R^4$, $R^5$ and $R^6$ are as defined above and $R^a$ is hydrogen and $R^b$ is hydrogen or hydroxy and X=Br.

According to scheme 3, further derivatives of imidazopyridines I are synthesized by coupling an activated ketone 4 with e.g. X=Br, with amino-pyridine 8 with e.g. X=Br in a suitable solvent, e.g. acetone or ethanol, at elevated temperature in an oil-bath or in a microwave to afford derivatives of compound 1. Palladium(O) mediated coupling of 1 with an amine $HNR^4R^5$ in presence of a suitable palladium source, e.g. $[Pd_2(dba)_3]$, a suitable ligand or additive, e.g. xantphos, in a suitable solvent, e.g. dioxane, and in presence of a suitable base, e.g. cesium carbonate, at elevated temperature is affording imidazopyridine I.

Further derivatives of imidazopyridines I are synthesized by alkylation of phenols (if $R^1$ and $R^2$ are hydroxy) using a suitable alkylation reagent, e.g. alkyl halide like 1-fluoroethyl bromide or alkyl tosylate like fluoromethyl tosylate, in presence of a suitable base, e.g. cesium carbonate or sodium hydride, in a suitable solvent, e.g. DMF, at ambient or elevated temperature.

Compounds of Formula IA

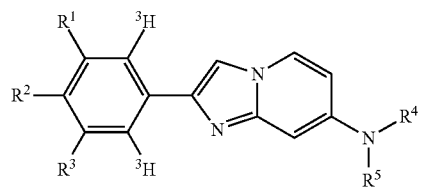

may be prepared in conventional manner with tritium gas in the presence of a catalyst, e.g. iridium, ruthenium, rhodium or palladium containing complexes in a suitable solvent, e.g. dichloromethane, chlorobenzene, DMF, DMSO or mixtures thereof, as described in example 61.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I or I can be separated using chiral HPLC.

Salts of Compounds of Formula I or II

The compounds of formula I or II are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I or II may be converted to the corresponding free bases by treatment with at least a stoichiometric equivalent of a suitable base such as sodium or potassium hydroxide, potassium carbonate, sodium bicarbonate, ammonia, and the like.

The compounds were investigated in accordance with the test given hereinafter.

TAU Radioligand-In-Vitro Displacement Assay

This in vitro binding assay assesses the affinity of compounds for native tau aggregates. The compounds are co-incubated with the well-established tau specific radioligand $[^3H]T808$ and the compound's displacement potency of $[^3H]T808$ binding is determined by in vitro autoradiography using human Alzheimer's disease (AD) brain sections (see illustration below).

Materials

AD human brains are purchased from Banner Sun Health Research Institute (Sun City, Ariz., USA). Pathological diagnosis of AD is made according to standard NIA-Reagan Institute criteria based on neuropathological data. The radioligand [$^3$H]T808 was synthesized in-house ([$^3$H]-2-[4-(2-Fluoro-ethyl)-piperidin-1-yl]-benzo[4,5]imidazo[1,2-a]pyrimidine, radiochemical purity 99.0%). As a reference cold T808 is used (2-[4-(2-Fluoro-ethyl)-piperidin-1-yl]-benzo[4,5]imidazo[1,2-a]pyrimidine). For the autoradiography FujiFilm Imaging Plates (BAS-IP TR 2025) are exposed to the sections and read with a FujiFilm IP reader (BAS-5000).

Method

Ten μm thick human AD brain sections are generated with a cryostat (Leica CM3050) at −17° C. chamber temperature and −15° C. object temperature. Sections are transferred to Histobond+ microscope slides (Marienfeld Laboratory Glasware). After drying for 3 hours at room temperature the sections are stored at −20° C. The sections are incubated with the radioligand (10 nM) and the respective cold compound (at various concentrations) in 50 mM Tris buffer, pH 7.4 at room temperature for 30 min. After washing 3×10 min at 4° C. in 50 mM Tris buffer, pH 7.4 and 3 quick dips in H$_2$O dist. at 4° C. the sections are dried at 4° C. for 3 h. The sections are placed in a FujiFilm Cassette (BAS 2025), exposed with an Imaging Plate for five days and afterwards scanned with a resolution of 25 μM per pixel.

Data Analysis

The signal intensity (Dens—PSL/mm2) in the region of interest (ROI) of the autoradiogram is quantified with the software MCID analysis (version 7.0, Imaging Research Inc.). The specific binding (SB) of [$^3$H]T808 binding in absence or in presence of a compound is calculated by subtracting the non-specific binding signal in the white matter, thus yielding SB$_{[3H]T808\ only}$ and SB$_{compound}$. The % displacement by the various compounds is calculated as following:

% displacement=100−(SB$_{compound}$/SB$_{[3H]T808\ only}$)*100.

Validation Data

In each experiment cold T808 is used as a positive internal control. Co-incubation of equimolar amounts of hot and cold T808 is expected to reduce specific binding by approximately 50%.

REFERENCES

A. K. Szardenings et al. 'Imaging agents for detecting neurological disorders'. US Patent Application US20110182812

W. Zhang et al., 'A highly selective and specific PET tracer for imaging of tau pathologies'. *Journal of Alzheimer's Disease* 31 (2012) 601-612.

Pharmaceutical Praparations

The compounds of formula I and II as well as their pharmaceutically acceptable salts can be administered in form of pharmaceutical preparations, normally parenterally, e.g. in the form of injection solutions.

Suitable excipients for injection solutions are e.g. water, alcohols, polyols, glycerol, vegetable oils etc.

TABLE

| Structure | Name | % displacement of [$^3$H]T808 (10 nM) at 1 uM | 10 nM | Expl. |
|---|---|---|---|---|
| 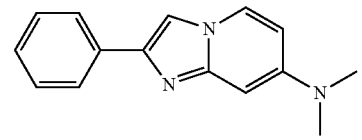 [SMILES: CN(C)c1ccn2cc(-c3ccccc3)nc2c1] | N-(2-fluoroethyl)-2-phenylimidazo[1,2-a]pyridin-7-amine | 93 | 40 | 1 |
| Formula I | | | | |
| 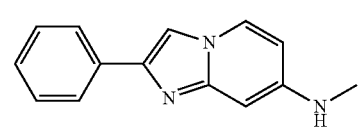 | N-(2-fluoroethyl)-N-methyl-2-phenylimidazo[1,2-a]pyridin-7-amine | 90 | 50 | 2 |
| Formula I | | | | |
| 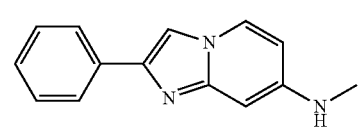 | N,N-dimethyl-2-phenylimidazo[1,2-a]pyridin-7-amine | 92 | 59 | 3 |
| Formula I | | | | |
| 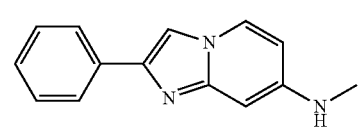 | N-methyl-2-phenylimidazo[1,2-a]pyridin-7-amine | 93 | 61 | 4 |
| Formula I | | | | |

TABLE-continued

| Structure | Name | % displacement of [³H]T808 (10 nM) at | | Expl. |
|---|---|---|---|---|
| | | 1 uM | 10 nM | |
| Formula I | 7-(4-fluoropiperidin-1-yl)-2-phenylimidazo[1,2-a]pyridine | 82 | 21 | 5 |
| Formula I | (S)-7-(3-fluoropyrrolidin-1-yl)-2-(4-methoxyphenyl)imidazo[1,2-a]pyridine | | 8 | 6 (S) |
| Formula I | (R)-7-(3-fluoropyrrolidin-1-yl)-2-(4-methoxyphenyl)imidazo[1,2-a]pyridine | | 11 | 7 (R) |
| Formula I | 2-(3-Methoxy-phenyl)-7-piperidin-1-yl-imidazo[1,2-a]pyridine | | 25 | 8 |
| Formula I | 2-(3-Methoxy-phenyl)-7-pyrrolidin-1-yl-imidazo[1,2-a]pyridine | | 33 | 9 |
| Formula I | 2-(3-Methoxy-phenyl)-7-morphonlin-1-yl-imidazo[1,2-a]pyridine | | 27 | 10 |

TABLE-continued

| Structure | Name | % displacement of [³H]T808 (10 nM) at | | Expl. |
|---|---|---|---|---|
| | | 1 uM | 10 nM | |
| Formula I | 2-(4-Methoxy-phenyl)-7-pyrrolidin-1-yl-imidazo[1,2-a]pyridine | 27 | | 11 |
| Formula I | 2-(4-Methoxy-phenyl)-7-piperidin-1-yl-imidazo[1,2-a]pyridine | 30 | | 12 |
| Formula I | 2-(4-Methoxy-phenyl)-7-morphonlin-1-yl-imidazo[1,2-a]pyridine | 40 | | 13 |
| Formula I | 7-(4-Fluoro-piperidin-1-yl)-2-(4-methoxy-phenyl)-imidazo[1,2-a]pyridine | 26 | | 14 |
| Formula I | 7-[4-(2-Fluoro-ethyl)-piperazin-1-yl]-2-(4-methoxy-phenyl)-imidazo[1,2-a]pyridine | 33 | | 15 |
| Formula I | [2-(4-Dimethylamino-phenyl)-imidazo[1,2-a]pyridin-7-yl]-dimethyl-amine | 29 | | 16 |
| Formula I | {2-[4-(2-Fluoro-ethoxy)-phenyl]-imidazo[1,2-a]pyridin-7-yl}-dimethyl-amine | 37 | | 17 |

TABLE-continued

| Structure | Name | % displacement of [³H]T808 (10 nM) at | | Expl. |
|---|---|---|---|---|
| | | 1 uM | 10 nM | |
| Formula I | [2-(4-Fluoromethoxy-phenyl)-imidazo[1,2-a]pyridin-7-yl]-dimethyl-amine | 46 | | 18 |
| Formula I | [2-(2,3-Dihydro-benzo[1,4]dioxin-6-yl)-imidazo[1,2-a]pyridin-7-yl]-methyl-amine | 37 | | 19 |
| Formula I | [2-(4-Methoxy-phenyl)-imidazo[1,2-a]pyridin-7-yl]-dimethyl-amine | 35 | | 20 |
| Formula I | 2-Benzo[1,3]dioxol-5-yl-7-[4-(2-fluoro-ethyl)-piperazin-1-yl]-imidazo[1,2-a]pyridine | 7 | | 21 |
| Formula I | [2-(2,3-Dihydro-benzo[1,4]dioxin-6-yl)-imidazo[1,2-a]pyridin-7-yl]-dimethyl-amine | 39 | | 22 |
| Formula I | [2-(2,3-Dihydro-benzo[1,4]dioxin-6-yl)-imidazo[1,2-a]pyridin-7-yl]-(2-fluoro-ethyl)-methyl-amine | 27 | | 23 |
| Formula I | 7-Azetidin-1-yl-2-(4-methoxy-phenyl)-imidazo[1,2-a]pyridine | 54 | | 24 |

TABLE-continued

| Structure | Name | % displacement of [³H]T808 (10 nM) at | | Expl. |
|---|---|---|---|---|
| | | 1 uM | 10 nM | |
| Formula I | N-methyl-2-m-tolylimidazo[1,2-a]pyridin-7-amine | 54 | | 25 |
| Formula I | N,N-Dimethyl-(2-m-tolyl-imidazo[1,2-a]pyridin-7-yl)-amine | 53 | | 26 |
| Formula I | N,N-Dimethyl-(2-p-tolyl-imidazo[1,2-a]pyridin-7-yl)-amine | 52 | | 27 |
| Formula I | N-Methyl-(2-p-tolyl-imidazo[1,2-a]pyridin-7-yl)-amine | 57 | | 28 |
| Formula I | N-(2-Fluoroethyl)-N-methyl-(2-p-tolyl-imidazo[1,2-a]pyridin-7-yl)-amine | 38 | | 29 |
| Formula I | 2-(4-(dimethylamino)phenyl)-N-(2-fluoroethyl)-N-methylimidazo[1,2-a]pyridin-7-amine | 23 | | 30 |
| Formula I | (S)-7-(3-fluoropyrrolidin-1-yl)-2-phenyl-imidazo[1,2-a]pyridine | 31 | | 31 |

TABLE-continued

| Structure | Name | % displacement of [³H]T808 (10 nM) at | | Expl. |
|---|---|---|---|---|
| | | 1 uM | 10 nM | |
| Formula I | [2-(3-Methoxy-phenyl)-imidazo[1,2-a]pyridin-7-yl]-dimethyl-amine | 36 | | 32 |
| Formula I | 2-(2,3-Dihydro-benzo[1,4]dioxin-6-yl)-7-[4-(2-fluoro-ethyl)-piperidin-1-yl]-imidazo[1,2-a]pyridine | 5 | | 33 |
| Formula I | (2-Fluoro-ethyl)-methyl-(2-m-tolyl-imidazo[1,2-a]pyridin-7-yl)-amine | 41 | | 34 |
| Formula I | 7-Morpholin-4-yl-2-m-tolyl-imidazo[1,2-a]pyridine | 27 | | 35 |
| Formula I | 7-Morpholin-4-yl-2-p-tolyl-imidazo[1,2-a]pyridine | 23 | | 36 |
| Formula I | (2-Benzo[1,3]dioxol-5-yl-imidazo[1,2-a]pyridin-7-yl)-methyl-amine | 60 | | 37 |

TABLE-continued

| Structure | Name | % displacement of [³H]T808 (10 nM) at | | Expl. |
|---|---|---|---|---|
| | | 1 uM | 10 nM | |
| Formula I | (2-Benzo[1,3]dioxol-5-yl-imidazo[1,2-a]pyridin-7-yl)-dimethyl-amine | 52 | | 38 |
| Formula I | (2-Benzo[1,3]dioxol-5-yl-imidazo[1,2-a]pyridin-7-yl)-(2-fluoro-ethyl)-methyl-amine | 42 | | 39 |
| Formula I | 4-(7-Azetidin-1-yl-imidazo[1,2-a]pyridin-2-yl)-phenol | 37 | | 40 |
| Formula I | {4-[7-(4-Fluoro-piperidin-1-yl)-imidazo[1,2-a]pyridin-2-yl]-phenyl}-dimethyl-amine | 18 | | 41 |
| Formula I | 7-((R)-3-Fluoro-pyrrolidin-1-yl)-2-phenyl-imidazo[1,2-a]pyridine | 23 | | 42 |
| Formula I | 7-((R)-3-Methoxy-pyrrolidin-1-yl)-2-phenyl-imidazo[1,2-a]pyridine | 15 | | 43 |
| Formula I | [2-(3-Methoxy-phenyl)-imidazo[1,2-a]pyridin-7-yl]-methyl-amine | 29 | | 44 |

TABLE-continued

| Structure | Name | % displacement of [³H]T808 (10 nM) at 1 uM | 10 nM | Expl. |
|---|---|---|---|---|
| Formula I | [2-(4-Fluoromethoxy-phenyl)-imidazo[1,2-a]pyridin-7-yl]-methyl-amine | | 45 | 45 |
| Formula I | (2-Fluoro-ethyl)-(2-p-tolyl-imidazo[1,2-a]pyridin-7-yl)-amine | | 27 | 46 |
| Formula I | (2-Fluoro-ethyl)-(2-m-tolyl-imidazo[1,2-a]pyridin-7-yl)-amine | | 36 | 47 |
| Formula I | 7-((S)-3-Methoxy-pyrrolidin-1-yl)-2-m-tolyl-imidazo[1,2-a]pyridine | | 8 | 48 |
| Formula I | 2-(4-Fluoromethoxy-phenyl)-7-morpholin-4-yl-imidazo[1,2-a]pyridine | | 10 | 49 |
| Formula I | (2-Fluoro-ethyl)-[2-(4-fluoromethoxy-phenyl)-imidazo[1,2-a]pyridin-7-yl]-amine | | 20 | 50 |
| Formula I | (2-Benzo[1,3]dioxol-5-yl-imidazo[1,2-a]pyridin-7-yl)-(2-fluoro-ethyl)-amine | | 35 | 51 |

TABLE-continued

| Structure | Name | % displacement of [³H]T808 (10 nM) at | | Expl. |
|---|---|---|---|---|
| | | 1 uM | 10 nM | |
| Formula I | [2-(3,4-Dimethyl-phenyl)-imidazo[1,2-a]pyridin-7-yl]-dimethyl-amine | 27 | | 52 |
| Formula I | [2-(3,4-Dimethyl-phenyl)-imidazo[1,2-a]pyridin-7-yl]-methyl-amine | 25 | | 53 |
| Formula I | 7-Azetidin-1-yl-2-p-tolyl-imidazo[1,2-a]pyridine | 30 | | 54 |
| Formula I | 7-Azetidin-1-yl-2-m-tolyl-imidazo[1,2-a]pyridine | 27 | | 55 |
| Formula I | 7-((R)-3-Methoxy-pyrrolidin-1-yl)-2-p-tolyl-imidazo[1,2-a]pyridine | 28 | | 56 |
| Formula I | 7-(4-Fluoro-piperidin-1-yl)-2-p-tolyl-imidazo[1,2-a]pyridine | 20 | | 57 |
| Formula I | 7-[4-(2-Fluoro-ethyl)-piperidin-1-yl]-2-phenyl-imidazo[1,2-a]pyridine | 12 | | 58 |

TABLE-continued

| Structure | Name | % displacement of [³H]T808 (10 nM) at | | Expl. |
|---|---|---|---|---|
| | | 1 uM | 10 nM | |
| Formula I | 7-((S)-3-Methoxy-pyrrolidin-1-yl)-2-phenyl-imidazo[1,2-a]pyridine | | 36 | 59 |
| Formula I | 7-(4-Fluoro-piperidin-1-yl)-2-(3-methoxy-phenyl)-imidazo[1,2-a]pyridine | | 14 | 60 |
| Formula I | [³H]-[2-(4-Fluoromethoxy-phenyl)-imidazo[1,2-a]pyridin-7-yl]-methyl-amine | | | 61 |
| Formula I | [³H]-N-methyl-2-phenyl-imidazo[1,2-a]pyridin-7-amine | | | 62 |
| Formula I | [³H]-N-(2-fluoroethyl)-2-phenyl-imidazo[1,2-a]pyridin-7-amine | | | 63 |
| Formula I | [³H]-N-Methyl-(2-p-tolyl-imidazo[1,2-a]pyridin-7-yl)-amine | | | 64 |

TABLE-continued

| Structure | Name | % displacement of [³H]T808 (10 nM) at | | Expl. |
|---|---|---|---|---|
| | | 1 uM | 10 nM | |
| Formula I | (2-Fluoro-ethyl)-[2-(4-methoxy-phenyl)-imidazo[1,2-a]pyridin-7-yl]-methyl-amine | 28 | | 65 |
| Formula I | [2-(3,4-Dimethoxy-phenyl)-imidazo[1,2-a]pyridin-7-yl]-methyl-amine | 40 | | 66 |
| Formula I | Cyclopropyl-[2-(4-methoxy-phenyl)-imidazo[1,2-a]pyridin-7-yl]-amine | 34 | | 67 |
| Formula I | 2-Benzo[1,3]dioxol-5-yl-7-(4-fluoro-piperidin-1-yl)-imidazo[1,2-a]pyridine | 25 | | 68 |
| Formula I | 7-(4-Fluoro-piperidin-1-yl)-2-m-tolyl-imidazo[1,2-a]pyridine | 22 | | 69 |
| Formula I | 7-Azetidin-1-yl-2-(4-fluoromethoxy-phenyl)-imidazo[1,2-a]pyridine | 32 | | 70 |
| Formula I | Methyl-[2-(4-methylsulfanyl-phenyl)-imidazo[1,2-a]pyridin-7-yl]-amine | 34 | | 71 |

TABLE-continued

| Structure | Name | % displacement of [³H]T808 (10 nM) at 1 uM | % displacement of [³H]T808 (10 nM) at 10 nM | Expl. |
|---|---|---|---|---|
| Formula I | [2-(3,4-Dimethyl-phenyl)-imidazo[1,2-a]pyridin-7-yl]-(2-fluoro-ethyl)-amine | | 25 | 72 |
| Formula I | [2-(3,4-Dimethoxy-phenyl)-imidazo[1,2-a]pyridin-7-yl]-(2-fluoro-ethyl)-amine | | 21 | 73 |
| Formula I | [2-(4-Methoxy-phenyl)-imidazo[1,2-a]pyridin-7-yl]-methyl-amine | | 44 | 74 |
| Formula I | (2-Fluoro-ethyl)-[2-(4-methoxy-phenyl)-imidazo[1,2-a]pyridin-7-yl]-amine | | 42 | 75 |
| Formula I | (2-Fluoro-ethyl)-[2-(3-methoxy-phenyl)-imidazo[1,2-a]pyridin-7-yl]-amine | | 31 | 76 |
| Formula I | 7-[4-(2-Fluoro-ethyl)-piperidin-1-yl]-2-(4-methoxy-phenyl)-imidazo[1,2-a]pyridine | | 27 | 77 |
| Formula I | [2-(3-Fluoromethoxy-phenyl)-imidazo[1,2-a]pyridin-7-yl]-dimethyl-amine | | 53 | 78 |

| Structure | Name | % displacement of [³H]T808 (10 nM) at | | Expl. |
|---|---|---|---|---|
| | | 1 uM | 10 nM | |
| 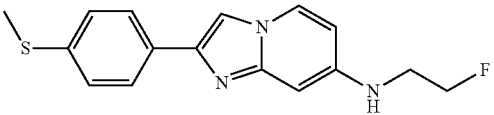 [SMILES: CSc1ccc(-c2cn3ccc(NCCF)cc3n2)cc1] Formula I | (2-Fluoro-ethyl)-[2-(4-methylsulfanyl-phenyl)-imidazo[1,2-a]pyridin-7-yl]-amine | | 20 | 79 |
| 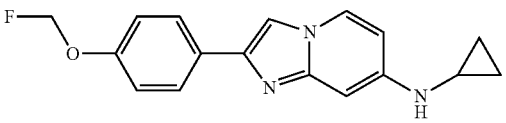 Formula I | Cyclopropyl-[2-(4-fluoromethoxy-phenyl)-imidazo[1,2-a]pyridin-7-yl]-amine | | 34 | 80 |
| 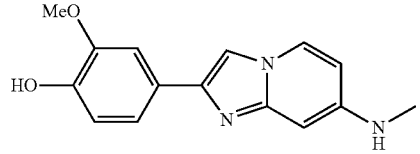 Formula I | 2-Methoxy-4-(7-methylamino-imidazo[1,2-a]pyridin-2-yl)-phenol | | 47 | 81 |
| 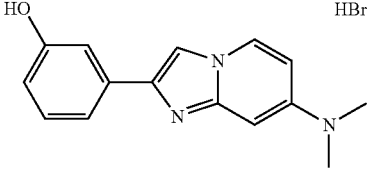 [SMILES: CN(C)c1ccn2cc(-c3cccc(O)c3)nc2c1 ; Br] Formula I | 3-(7-Dimethylamino-imidazo[1,2-a]pyridin-2-yl)-phenol hydrobromide | | 49 | 82 |
| 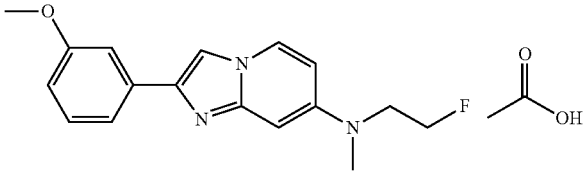 Formula I | N-(2-fluoroethyl)-2-(3-methoxyphenyl)-N-methylimidazo[1,2-a]pyridin-7-amine | | 32 | 83 |
| 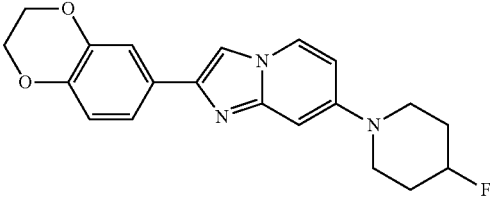 [SMILES: FC1CCN(c2ccn3cc(-c4ccc5c(c4)OCCO5)nc3c2)CC1] Formula I | 2-(2,3-Dihydro-benzo[1,4]dioxin-6-yl)-7-(4-fluoro-piperidin-1-yl)-imidazo[1,2-a]pyridine | | 26 | 84 |
| 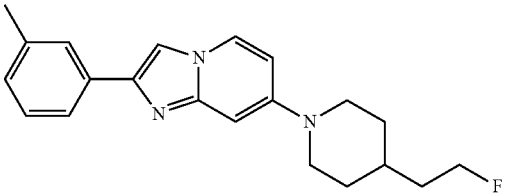 Formula I | 7-[4-(2-Fluoro-ethyl)-piperidin-1-yl]-2-m-tolyl-imidazo[1,2-a]pyridine | | 17 | 85 |

TABLE-continued

| Structure | Name | % displacement of [³H]T808 (10 nM) at 1 uM | % displacement of [³H]T808 (10 nM) at 10 nM | Expl. |
|---|---|---|---|---|
| Formula I | 7-((R)-3-Methoxy-pyrrolidin-1-yl)-2-m-tolyl-imidazo[1,2-a]pyridine | | 33 | 86 |
| Formula I | 7-[4-(2-Fluoro-ethyl)-piperidin-1-yl]-2-p-tolyl-imidazo[1,2-a]pyridine | | 5 | 87 |
| Formula I | 7-((S)-3-Methoxy-pyrrolidin-1-yl)-2-p-tolyl-imidazo[1,2-a]pyridine | | 34 | 88 |
| Formula I | [4-[7-(Methylamino)imidazo[1,2-a]pyridin-2-yl]phenyl]methanol | | 54 | 89 |
| Formula I | [4-[7-(Dimethylamino)imidazo[1,2-a]pyridin-2-yl]phenyl]methanol | | 32 | 90 |
| Formula I | 7-(azetidin-1-yl)-2-(3-methoxyphenyl)imidazo[1,2-a]pyridine | | 39 | 91 |
| Formula I | 2-(3,5-dimethoxyphenyl)-N-methylimidazo[1,2-a]pyridin-7-amine | | 25 | 92 |

TABLE-continued

| Structure | Name | % displacement of [³H]T808 (10 nM) at | | Expl. |
|---|---|---|---|---|
| | | 1 uM | 10 nM | |
| Formula I | N-[2-(4-Ethoxy-phenyl)-imidazo[1,2-a]pyridin-7-yl]-methyl-amine | 39 | | 93 |
| Formula I | Methyl-[2-(4-pyrrolidin-1-yl-phenyl)-imidazo[1,2-a]pyridin-7-yl]-amine | 18 | | 94 |
| Formula I | N-[2-(3-Fluoro-4-methoxy-phenyl)-imidazo[1,2-a]pyridin-7-yl]-methyl-amine | 55 | | 95 |
| Formula I | N-[2-(3,4-Dihydro-2H-benzo[b][1,4]dioxepin-7-yl)-imidazo[1,2-a]pyridin-7-yl]-methyl-amine | 35 | | 96 |
| Formula I | N-[2-(4-Diethylamino-phenyl)-imidazo[1,2-a]pyridin-7-yl]-methyl-amine | 18 | | 97 |
| Formula I | N-[2-(4-Ethyl-phenyl)-imidazo[1,2-a]pyridin-7-yl]-methyl-amine | 38 | | 98 |
| Formula I | 2-[4-(Methoxymethyl)phenyl]-N,N-dimethyl-imidazo[1,2-a]pyridin-7-amine | 37 | | 99 |
| Formula II | Methyl-(2-thiophen-3-yl-imidazo[1,2-a]pyridin-7-yl)-amine | 59 | | 100 |

TABLE-continued

| Structure | Name | % displacement of [³H]T808 (10 nM) at 1 uM | % displacement of [³H]T808 (10 nM) at 10 nM | Expl. |
|---|---|---|---|---|
| Formula II | N-(2-Furan-2-yl-imidazo[1,2-a]pyridin-7-yl)-methyl-amine | | 50 | 101 |
| Formula II | N-(2-Thiophen-2-yl-imidazo[1,2-a]pyridin-7-yl)-methyl-amine | | 50 | 102 |
| Formula I | Methyl-[2-(4-morpholin-4-yl-phenyl)-imidazo[1,2-a]pyridin-7-yl]-amine | | 47 | 103 |
| Formula II | Methyl-(2-thiazol-2-yl-imidazo[1,2-a]pyridin-7-yl)-amine | | 10 | 104 |
| Formula I | 2-[4-(2-Fluoroethoxymethyl)phenyl]-N,N-dimethyl-imidazo[1,2-a]pyridin-7-amine | | 10 | 105 |
| Formula I | 7-(Azetidin-1-yl)-2-[4-(2-fluoroethoxy)phenyl]imidazo[1,2-a]pyridine | | 36 | 106 |
| Formula I | 7-(Azetidin-1-yl)-2-[3-(fluoromethoxy)phenyl]imidazo[1,2-a]pyridine | | 48 | 107 |

TABLE-continued

| Structure | Name | % displacement of [³H]T808 (10 nM) at 1 uM | % displacement of [³H]T808 (10 nM) at 10 nM | Expl. |
|---|---|---|---|---|
| Formula I | 2-(3-methoxy-4-methylphenyl)-N-methylimidazo[1,2-a]pyridin-7-amine | 26 | | 108 |
| Formula I | 2-[4-(2-Fluoroethoxy)phenyl]-N-methylimidazo[1,2-a]pyridin-7-amine | 40 | | 109 |
| Formula I | 2-(4-(benzyl(methyl)amino)phenyl)-N-methylimidazo[1,2-a]pyridin-7-amine | 14 | | 110 |
| Formula II | N-[2-(3-Bromo-thiophen-2-yl)-imidazo[1,2-a]pyridin-7-yl]-methyl-amine | 17 | | 111 |
| Formula II | N-[2-(3-Chloro-thiophen-2-yl)-imidazo[1,2-a]pyridin-7-yl]-methyl-amine | 6 | | 112 |
| Formula I | N-[2-(4-Difluoromethoxy-phenyl)-imidazo[1,2-a]pyridin-7-yl]-methyl-amine | 48 | | 113 |
| Formula I | N-[2-(4-Bromo-phenyl)-imidazo[1,2-a]pyridin-7-yl]-methyl-amine | 33 | | 114 |

TABLE-continued

| Structure | Name | % displacement of [³H]T808 (10 nM) at | | Expl. |
|---|---|---|---|---|
| | | 1 uM | 10 nM | |
| Formula II | Methyl-[2-(5-methyl-furan-2-yl)-imidazo[1,2-a]pyridin-7-yl]-amine | | 58 | 115 |
| Formula II | N-[2-(Benzofuran-2-yl)-imidazo[1,2-a]pyridin-7-yl]-methyl-amine | | 47 | 116 |
| Formula II | N-[2-(2,5-Dimethyl-2H-pyrazol-3-yl)-imidazo[1,2-a]pyridin-7-yl]-methyl-amine | | 18 | 117 |
| Formula I | Methyl-[2-(4-piperidin-1-yl-phenyl)-imidazo[1,2-a]pyridin-7-yl]-amine | | 20 | 118 |
| Formula I | 6-(7-Methylamino-imidazo[1,2-a]pyridin-2-yl)-4H-benzo[1,4]oxazin-3-one | | 46 | 119 |
| Formula I | 2-(7-Methylamino-imidazo[1,2-a]pyridin-2-yl)-phenol | | 20 | 120 |
| Formula II | Methyl-[2-(1-methyl-1H-benzoimidazol-2-yl)-imidazo[1,2-a]pyridin-7-yl]-amine | | 19 | 121 |
| Formula I | Methyl 3-[7-(methylamino)imidazo[1,2-a]pyridin-2-yl]benzoate | | 20 | 122 |

TABLE-continued

| Structure | Name | % displacement of [³H]T808 (10 nM) at | | Expl. |
|---|---|---|---|---|
| | | 1 uM | 10 nM | |
| 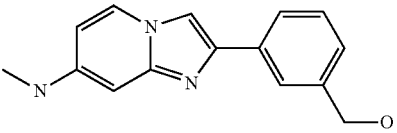 Formula I | [3-[7-(Methylamino)imidazo[1,2-a]pyridin-2-yl]phenyl]methanol | 23 | | 123 |
| 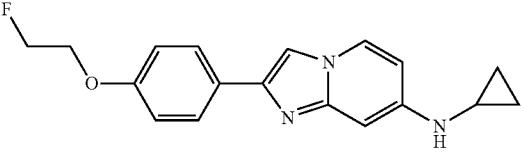 [SMILES: FCCOc1ccc(-c2cn3ccc(NC4CC4)cc3n2)cc1] Formula I | N-Cyclopropyl-2-[4-(2-fluoroethoxy)phenyl]imidazo[1,2-a]pyridin-7-amine | 39 | | 124 |
| 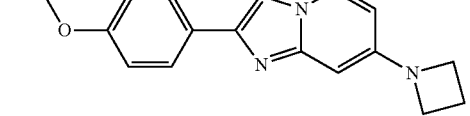 Formula I | 7-(Azetidin-1-yl)-2-[4-(3-fluoropropoxy)phenyl]imidazo[1,2-a]pyridine | 32 | | 125 |
| 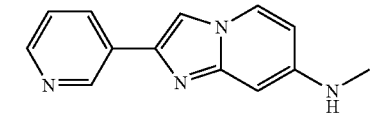 [SMILES: CNc1ccn2cc(-c3cccnc3)nc2c1] Formula II | Methyl-(2-pyridin-3-yl-imidazo[1,2-a]pyridin-7-yl)-amine | 12 | | 126 |
| 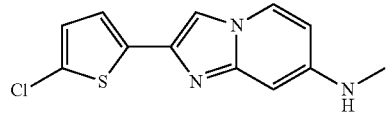 [SMILES: CNc1ccn2cc(-c3ccc(Cl)s3)nc2c1] Formula II | N-[2-(5-Chloro-thiophen-2-yl)-imidazo[1,2-a]pyridin-7-yl]-methyl-amine | 26 | | 127 |
| 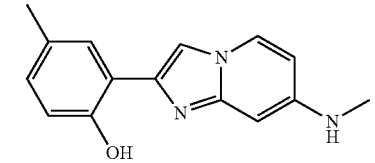 [SMILES: CNc1ccn2cc(-c3cc(C)ccc3O)nc2c1] Formula I | 4-Methyl-2-(7-methylamino-imidazo[1,2-a]pyridin-2-yl)-phenol | 34 | | 128 |
| 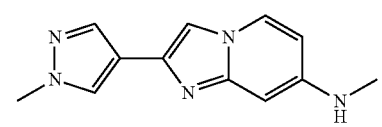 Formula II | Methyl-[2-(1-methyl-1H-pyrazol-4-yl)-imidazo[1,2-a]pyridin-7-yl]-amine | 50 | | 129 |

| Structure | Name | % displacement of [³H]T808 (10 nM) at | | Expl. |
|---|---|---|---|---|
| | | 1 uM | 10 nM | |
| Formula I | 2-[3-(Methoxymethyl)phenyl]-N-methyl-imidazo[1,2-a]pyridine-7-amine | 40 | | 130 |
| Formula I | 2-(4-(2-fluoroethylamino)phenyl)-N-methylimidazo[1,2-a]pyridin-7-amine | 43 | | 131 |
| Formula I | N-(3-fluoropropyl)-2-(4-methoxyphenyl)imidazo[1,2-a]pyridin-7-amine | 38 | | 132 |
| Formula I | 2-(3-(fluoromethoxy)phenyl)-N-methylimidazo[1,2-a]pyridin-7-amine | 40 | | 133 |
| Formula I | 2-(2-(4-methoxyphenyl)imidazo[1,2-a]pyridin-7-ylamino)propan-1-ol | 21 | | 134 |
| Formula I | N-(2-fluoroethyl)-2-(3-methoxy-4-methylphenyl)imidazo[1,2-a]pyridin-7-amine | 14 | | 135 |
| Formula I | N-methyl-2-(3-(methylthio)phenyl)imidazo[1,2-a]pyridin-7-amine | 20 | | 136 |

TABLE-continued

| Structure | Name | % displacement of [³H]T808 (10 nM) at | | Expl. |
|---|---|---|---|---|
| | | 1 uM | 10 nM | |
| Formula I | 2-(3-(2-fluoroethoxy)phenyl)-N-methylimidazo[1,2-a]pyridin-7-amine | 41 | | 137 |
| Formula I | 2-(4-methoxyphenyl)-7-(2-methylaziridin-1-yl)imidazo[1,2-a]pyridine | 44 | | 138 |
| Formula I | 2-(3-(3-fluoropropoxy)phenyl)-N-methylimidazo[1,2-a]pyridin-7-amine | 5 | | 139 |
| Formula I | 7-(azetidin-1-yl)-2-(3-(2-fluoroethoxy)phenyl)imidazo[1,2-a]pyridine | 23 | | 140 |
| Formula I | 2-(4-(4-fluoropiperidin-1-yl)phenyl)-N-methylimidazo[1,2-a]pyridin-7-amine | 35 | | 141 |
| Formula I | 4-(7-(2-fluoroethylamino)imidazo[1,2-a]pyridin-2-yl)-2-methoxyphenol | 11 | | 142 |
| Formula I | 2-(2,3-dihydrobenzo[b][1,4]dioxin-6-yl)-N-(2-fluoroethyl)imidazo[1,2-a]pyridin-7-amine | 23 | | 143 |

TABLE-continued

| Structure | Name | % displacement of [³H]T808 (10 nM) at 1 uM | % displacement of [³H]T808 (10 nM) at 10 nM | Expl. |
|---|---|---|---|---|
| Formula I | 7-(azetidin-1-yl)-2-(4-(2-(2-fluoroethoxy)ethoxy)phenyl)imidazo[1,2-a]pyridine | | 27 | 144 |
| Formula I | 4-(7-(2-fluoroethylamino)imidazo[1,2-a]pyridin-2-yl)phenol | | 29 | 145 |
| Formula I | 3-(7-(2-fluoroethylamino)imidazo[1,2-a]pyridin-2-yl)phenol | | 33 | 146 |
| Formula I | N-(2-Fluoroethyl)-2-(4-morpholin-4-ylphenyl)imidazo[1,2-a]pyridin-7-amine | | 23 | 147 |
| Formula I | N-Cyclopropyl-2-[4-(3-fluoropropoxy)phenyl]imidazo[1,2-a]pyridin-7-amine | | 20 | 148 |
| Formula II | N-(2-Fluoroethyl)-2-(furan-2-yl)imidazo[1,2-a]pyridin-7-amine | | 23 | 149 |

Example 1

N-(2-Fluoroethyl)-2-phenylimidazo[1,2-a]pyridin-7-amine 2,2,2-trifluoroacetate

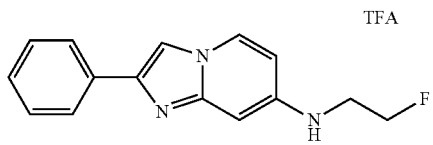 [SMILES: FCCNc1ccn2cc(-c3ccccc3)nc2c1]

a) tert-Butyl 2-fluoroethyl(2-phenylimidazo[1,2-a]pyridin-7-yl)carbamate

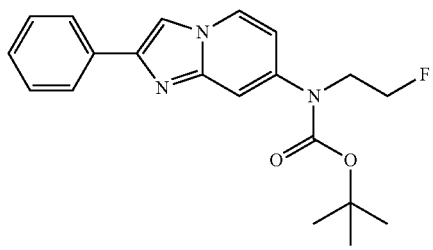 [SMILES: CC(C)(C)OC(=O)N(CCF)c1ccn2cc(-c3ccccc3)nc2c1]

To a solution of tert-butyl 2-phenylimidazo[1,2-a]pyridin-7-ylcarbamate (418 mg, 1.35 mmol) in DMF (4 mL) was added carefully under an atmosphere of nitrogen at 0° C. sodium hydride 60% (64.8 mg, 1.62 mmol). After stirring for 30 min at ambient temperature, 1-bromo-2-fluoroethane (189 mg, 111 µL, 1.49 mmol) was added drop-wise. Then the reaction mixture was stirred at ambient temperature for 3 h. After further addition of sodium hydride 60% (27.0 mg, 676 µmol) it was stirred for 30 min at ambient temperature before further 1-bromo-2-fluoroethane (85.8 mg, 50.5 µL, 676 µmol) was added and the solution was stirred for 18 h. It was diluted with dichloromethane (15 mL) and was washed twice with water (15 mL). The aqueous layers were extracted with dichloromethane (15 mL). The combined organic layers were dried over magnesium sulfate, filtered and concentrated. Purification by chromatography (dichloromethane:methanol=100:0 to 97:3) afforded the title compound (305 mg, 64%) as a white solid. MS m/z: 356.6 [M+H]⁺ b) N-(2-Fluoroethyl)-2-phenylimidazo[1,2-a]pyridin-7-amine 2,2,2-trifluoroacetate

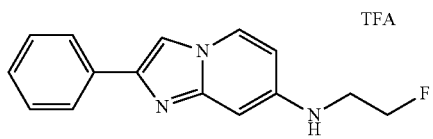 [SMILES: FCCNc1ccn2cc(-c3ccccc3)nc2c1]

To a solution of tert-butyl 2-fluoroethyl(2-phenylimidazo[1,2-a]pyridin-7-yl)carbamate (301 mg, 847 µmol) in dichloromethane (1.2 ml) was added under an atmosphere of nitrogen trifluoroacetic acid (1.78 g, 1.2 mL, 15.6 mmol). The reaction mixture was stirred at ambient temperature for 2 h. It was concentrated and the residue was diluted with ethanol and was concentrated again. This procedure was repeated and the residue was dried in vacuao affording the title compound as its trifluoroacetic acid salt (369 mg, 85%) as a light brown solid. MS m/z: 256.5 [M+H]⁺

Example 2

N-(2-Fluoroethyl)-N-methyl-2-phenylimidazo[1,2-a]pyridin-7-amine

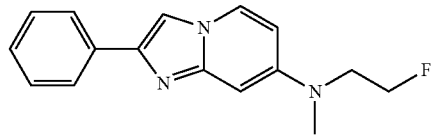 [SMILES: CN(CCF)c1ccn2cc(-c3ccccc3)nc2c1]

To a solution of N-(2-fluoroethyl)-2-phenylimidazo[1,2-a]pyridin-7-amine 2,2,2-trifluoroacetate (280 mg, 758 µmol) in DMF (3 mL) was added under an atmosphere of nitrogen sodium hydride 60% (75.8 mg, 1.9 mmol). After stirring at ambient temperature for 30 min, iodo-methane (237 mg, 104 µL, 1.67 mmol) was added and stirring was continued in a closed flask at ambient temperature for 18 h. The reaction mixture was diluted with ethyl acetate (15 mL) and was washed with an aqueous solution of citric acid (5%), water (15 mL) and brine (10 mL). The aqueous layers were extracted with ethyl acetate (15 mL). The combined organic layers were dried over magnesium sulfate, filtered and concentrated. Purification by chromatography (heptane:dichloromethane=80:20 to 0:100) afforded the title compound (19 mg, 9%) as a brown solid. MS m/z: 270.5 [M+H]⁺

Example 3

N,N-Dimethyl-2-phenylimidazo[1,2-a]pyridin-7-amine

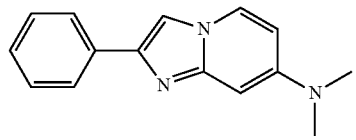 [SMILES: CN(C)c1ccn2cc(-c3ccccc3)nc2c1]

To a solution of 2-phenylimidazo[1,2-a]pyridin-7-amine (500 mg, 2.39 mmol) in DMF (2 mL) was added under an atmosphere of nitrogen sodium hydride 60% (172 mg, 4.3 mmol). After stirring at ambient temperature for 30 min, iodomethane (611 mg, 269 µL, 4.3 mmol) was added and the reaction mixture was stirred in a closed flask for 18 h. The concentrated mixture was adsorbed on Isolute® and purification by chromatography (heptane:dichloromethane=80:20 to 0:100) afforded the title compound (35 mg, 6%) as a light brown solid. MS m/z: 238.6 [M+H]⁺

Example 4

N-Methyl-2-phenylimidazo[1,2-a]pyridin-7-amine

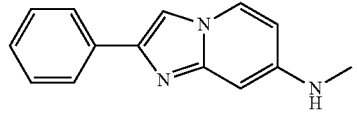 [SMILES: CNc1ccn2cc(-c3ccccc3)nc2c1]

To a solution of 2-phenylimidazo[1,2-a]pyridin-7-amine (500 mg, 2.39 mmol) in DMF (2 mL) was added under an atmosphere of nitrogen sodium hydride 60% (172 mg, 4.3 mmol). After stirring at ambient temperature for 30 min, iodomethane (611 mg, 269 µL, 4.3 mmol) was added and the reaction mixture was stirred in a closed flask for 18 h. The concentrated mixture was adsorbed on Isolute® and purification by chromatography (heptane:dichloromethane=80:20 to 0:100) afforded the title compound (42 mg, 8%) as a brown solid. MS m/z: 224.5 [M+H]$^+$ Example 5

7-(4-Fluoropiperidin-1-yl)-2-phenylimidazo[1,2-a]pyridine

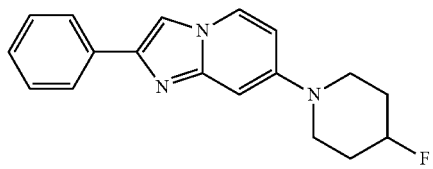 [SMILES: FC1CCN(c2ccn3cc(-c4ccccc4)nc3c2)CC1]

To a solution of 7-bromo-2-phenylimidazo[1,2-a]pyridine (51 mg, 149 µmol) and 4-fluoropiperidine hydrochloride (52.1 mg, 373 µmol) in dioxane (2.5 mL) was added cesium carbonate (243 mg, 747 µmol). Under an argon atmosphere [Pd$_2$(dba)$_3$](13.7 mg, 14.9 µmol) and xantphos (17.3 mg, 29.9 µmol) were added and the reaction mixture was stirred at 110° C. for 20 h. It was filtered over Celit® and washed with dioxane (~20 mL). Concentration and purification by chromatography (dichloromethane:methanol=100:0 to 95:5) afforded the title compound (15 mg, 33%) as a light brown solid. MS m/z: 296.5 [M+H]$^+$ Example 6

(S)-7-(3-Fluoropyrrolidin-1-yl)-2-(4-methoxyphenyl)imidazo[1,2-a]pyridine

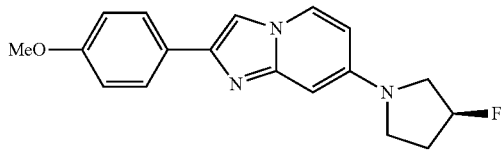 [SMILES: COc1ccc(-c2cn3ccc(N4CC[C@H](F)C4)cc3n2)cc1]

a) 7-Bromo-2-(4-methoxyphenyl)imidazo[1,2-a]pyridine

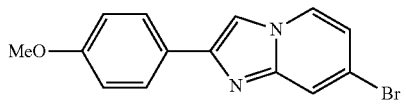 [SMILES: COc1ccc(-c2cn3ccc(Br)cc3n2)cc1]

To 4-bromopyridin-2-amine (1.04 g, 6.01 mmol) and 2-bromo-1-(4-methoxyphenyl)ethanone (1.38 g, 6.01 mmol) was added acetone (10 mL). The reaction mixture was heated at 70° C. for 20 h. The reaction mixture was filtered and washed with acetone. To the resulting white solid was added aqueous ammonium hydroxide (25%) and water. The resulting light yellow suspension was filtrated and washed with water. Drying at high vacuum afforded the title compound (1.69 g, 79%) as a light yellow solid. MS m/z: 303.4 [M]$^+$ b) (S)-7-(3-Fluoropyrrolidin-1-yl)-2-(4-methoxyphenyl)imidazo[1,2-a]pyridine

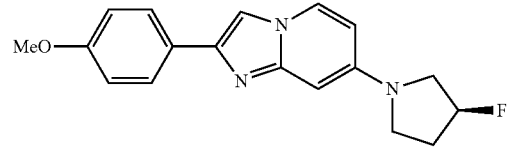 [SMILES: COc1ccc(-c2cn3ccc(N4CC[C@H](F)C4)cc3n2)cc1]

In analogy to the experimental procedure of example 5) 7-bromo-2-(4-methoxyphenyl)imidazo[1,2-a]pyridine instead of 7-bromo-2-phenylimidazo[1,2-a]pyridine was converted using (S)-3-fluoropyrrolidine hydrochloride instead of 4-fluoropiperidine hydrochloride into the title compound (35 mg, 39%) which was obtained as a light brown solid. MS m/z: 312.5 [M+H]$^+$ Example 7

(R)-7-(3-Fluoropyrrolidin-1-yl)-2-(4-methoxyphenyl)imidazo[1,2-a]pyridine

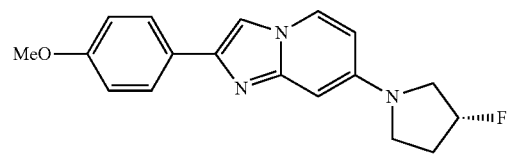 [SMILES: COc1ccc(-c2cn3ccc(N4CC[C@@H](F)C4)cc3n2)cc1]

In analogy to the experimental procedure of example 5) 7-bromo-2-(4-methoxyphenyl)imidazo[1,2-a]pyridine instead of 7-bromo-2-phenylimidazo[1,2-a]pyridine was converted using (R)-3-fluoropyrrolidine hydrochloride instead of 4-fluoropiperidine hydrochloride into the title compound (13 mg, 15%) which was obtained as an off-white solid. MS m/z: 312.5 [M+H]$^+$ Example 8

2-(3-Methoxy-phenyl)-7-piperidin-1-yl-imidazo[1,2-a]pyridine

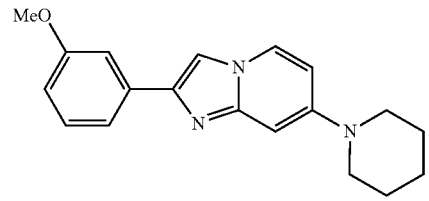 [SMILES: COc1cccc(-c2cn3ccc(N4CCCCC4)cc3n2)c1]

a) 7-Bromo-2-(3-methoxyphenyl)imidazo[1,2-a]pyridine

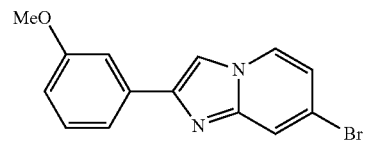 [SMILES: COc1cccc(-c2cn3ccc(Br)cc3n2)c1]

In analogy to the experimental procedure of example 6a) 4-bromopyridin-2-amine was converted using 2-bromo-1-(3-methoxyphenyl)ethanone instead of 2-bromo-1-(4- methoxyphenyl)ethanone into the title compound (950 mg, 72%) which was obtained as an off-white solid. MS m/z: 302.8 [M]+ b) 2-(3-Methoxy-phenyl)-7-piperidin-1-yl-imidazo[1,2-a]pyridine

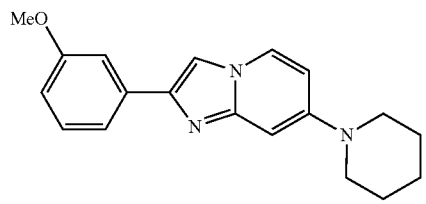 [SMILES: COc1cccc(-c2cn3ccc(N4CCCCC4)cc3n2)c1]

In analogy to the experimental procedure of example 5) 7-bromo-2-(3-methoxyphenyl)imidazo[1,2-a]pyridine instead of 7-bromo-2-phenylimidazo[1,2-a]pyridine was converted using piperidine instead of 4-fluoropiperidine hydrochloride into the title compound (25 mg, 12%) which was obtained as an off-white solid. MS m/z: 308.2 [M+H]+

Example 9

2-(3-Methoxy-phenyl)-7-pyrrolidin-1-yl-imidazo[1,2-a]pyridine

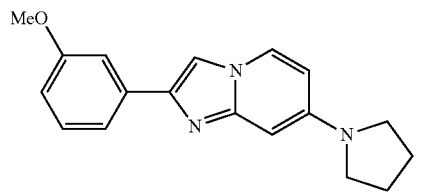 [SMILES: COc1cccc(-c2cn3ccc(N4CCCC4)cc3n2)c1]

In analogy to the experimental procedure of example 5) 7-bromo-2-(3-methoxyphenyl)imidazo[1,2-a]pyridine instead of 7-bromo-2-phenylimidazo[1,2-a]pyridine was converted using pyrrolidine instead of 4-fluoropiperidine hydrochloride into the title compound (45 mg, 23%) which was obtained as an off-white solid. MS m/z: 294.0 [M+H]+

Example 10

2-(3-Methoxy-phenyl)-7-morpholin-4-yl-imidazol[1,2-a]pyridine

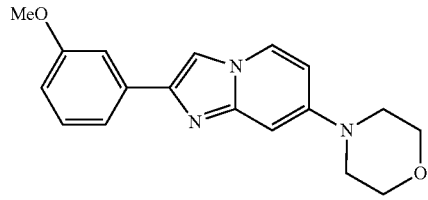 [SMILES: COc1cccc(-c2cn3ccc(N4CCOCC4)cc3n2)c1]

In analogy to the experimental procedure of example 5) 7-bromo-2-(3-methoxyphenyl)imidazo[1,2-a]pyridine instead of 7-bromo-2-phenylimidazo[1,2-a]pyridine was converted using morpholine instead of 4-fluoropiperidine hydrochloride into the title compound (95 mg, 31%) which was obtained as an off-white solid. MS m/z: 310.4 [M+H]+

Example 11

2-(4-Methoxy-phenyl)-7-pyrrolidin-1-yl-imidazo[1,2-a]pyridine

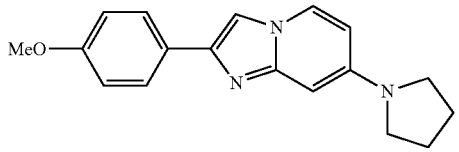 [SMILES: COc1ccc(-c2cn3ccc(N4CCCC4)cc3n2)cc1]

In analogy to the experimental procedure of example 5) 7-bromo-2-(4-methoxyphenyl)imidazo[1,2-a]pyridine instead of 7-bromo-2-phenylimidazo[1,2-a]pyridine was converted using pyrrolidine instead of 4-fluoropiperidine hydrochloride into the title compound (60 mg, 21%) which was obtained as a white solid. MS m/z: 293.8 [M+H]+

Example 12

2-(4-Methoxy-phenyl)-7-piperidin-1-yl-imidazo[1,2-a]pyridine

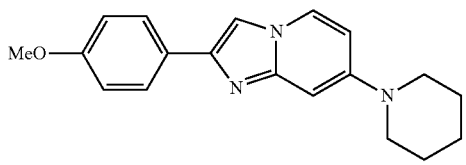 [SMILES: COc1ccc(-c2cn3ccc(N4CCCCC4)cc3n2)cc1]

In analogy to the experimental procedure of example 5) 7-bromo-2-(4-methoxyphenyl)imidazo[1,2-a]pyridine instead of 7-bromo-2-phenylimidazo[1,2-a]pyridine was converted using piperidine instead of 4-fluoropiperidine hydrochloride into the title compound (55 mg, 18%) which was obtained as a white solid. MS m/z: 308.2 [M+H]+

Example 13

2-(4-Methoxy-phenyl)-7-morpholin-4-yl-imidazo[1,2-a]pyridine

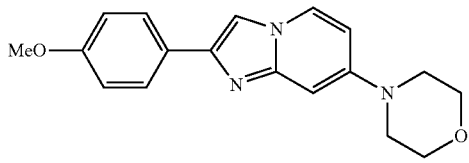 [SMILES: COc1ccc(-c2cn3ccc(N4CCOCC4)cc3n2)cc1]

In analogy to the experimental procedure of example 5) 7-bromo-2-(4-methoxyphenyl)imidazo[1,2-a]pyridine instead of 7-bromo-2-phenylimidazo[1,2-a]pyridine was converted using morpholine instead of 4-fluoropiperidine hydrochloride into the title compound (60 mg, 20%) which was obtained as a white solid. MS m/z: 310.2 [M+H]+

Example 14

7-(4-Fluoro-piperidin-1-yl)-2-(4-methoxy-phenyl)-imidazo[1,2-a]pyridine

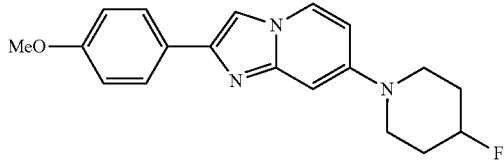 [SMILES: COc1ccc(-c2cn3ccc(N4CCC(F)CC4)cc3n2)cc1]

In analogy to the experimental procedure of example 5) 7-bromo-2-(3-methoxyphenyl)imidazo[1,2-a]pyridine instead of 7-bromo-2-phenylimidazo[1,2-a]pyridine was converted using 4-fluoropiperidine hydrochloride into the title compound (15 mg, 12%) which was obtained as a white solid. MS m/z: 326.2 [M+H]$^+$

Example 15

7-[4-(2-Fluoro-ethyl)-piperazin-1-yl]-2-(4-methoxy-phenyl)-imidazo[1,2-a]pyridine

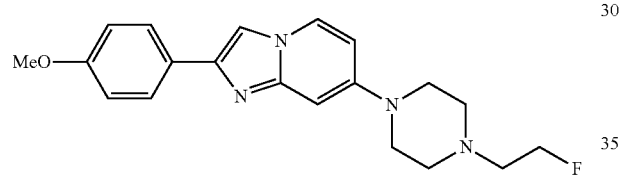

In analogy to the experimental procedure of example 5) 7-bromo-2-(4-methoxyphenyl)imidazo[1,2-a]pyridine instead of 7-bromo-2-phenylimidazo[1,2-a]pyridine was converted using 1-(2-fluoroethyl)piperazine hydrochloride instead of 4-fluoropiperidine hydrochloride into the title compound (25 mg, 22%) which was obtained as an off-white solid. MS m/z: 355.4 [M+H]$^+$

Example 16

[2-(4-Dimethylamino-phenyl)-imidazo[1,2-a]pyridin-7-yl]-dimethyl-amine

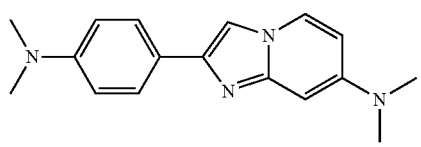

In analogy to the experimental procedure of example 6a) N4,N4-dimethylpyridine-2,4-diamine instead of 4-bromopyridin-2-amine was converted using 2-bromo-1-(4-(dimethylamino)phenyl)ethanone instead of 2-bromo-1-(4-methoxyphenyl)ethanone into the title compound (120 mg, 26%) which was obtained as a light grey solid. MS m/z: 281.5 [M+H]$^+$

Example 17

{2-[4-(2-Fluoro-ethoxy)-phenyl]-imidazo[1,2-a]pyridin-7-yl}-dimethyl-amine

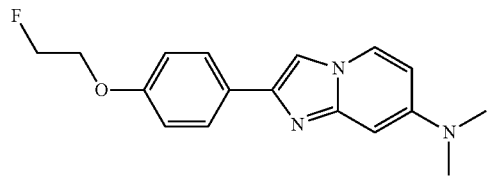 [SMILES: CN(C)c1ccn2cc(-c3ccc(OCCF)cc3)nc2c1]

a) 4-(7-Dimethylamino-imidazo[1,2-a]pyridin-2-yl)-phenol

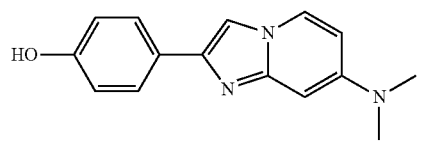 [SMILES: CN(C)c1ccn2cc(-c3ccc(O)cc3)nc2c1]

In analogy to the experimental procedure of example 6a) N4,N4-dimethylpyridine-2,4-diamine instead of 4-bromopyridin-2-amine was converted using 2-bromo-1-(4-hydroxyphenyl)ethanone instead of 2-bromo-1-(4-methoxyphenyl)ethanone into the title compound (995 mg, 80%) which was obtained as an off-white solid. MS m/z: 254.5 [M+H]$^+$ b) {2-[4-(2-Fluoro-ethoxy)-phenyl]-imidazo[1,2-a]pyridin-7-yl}-dimethyl-amine

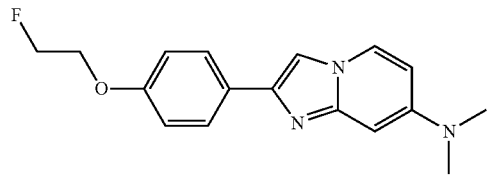 [SMILES: CN(C)c1ccn2cc(-c3ccc(OCCF)cc3)nc2c1]

A solution of 4-(7-(dimethylamino)imidazo[1,2-a]pyridin-2-yl)phenol (155 mg, 490 µmol) and 1-bromo-2-fluoroethane (62.1 mg, 490 µmol) in DMF (2.5 mL) was stirred for 15 min at ambient temperature. Cesium carbonate (207 mg, 636 µmol) was added and the vessel was sealed and heated at 70° C. for 20 h. It was filtrated, washed and dried at high vacuum. Purification by chromatography (dichloromethane:methanol=100:0 to 85:15) afforded the title compound (79 mg, 53%) as a light yellow solid. MS m/z: 300.5 [M+H]$^+$

Example 18

[2-(4-Fluoromethoxy-phenyl)-imidazo[1,2-a]pyridin-7-yl]-dimethyl-amine

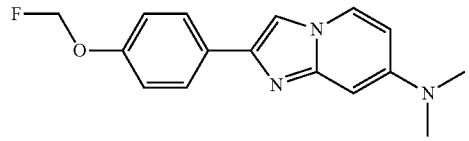 [SMILES: CN(C)c1ccn2cc(-c3ccc(OCF)cc3)nc2c1]

In analogy to the experimental procedure of example 17b) 4-(7-(dimethylamino)imidazo[1,2-a]pyridin-2-yl)phenol was converted using fluoromethyl 4-methylbenzenesulfonate instead of 1-bromo-2-fluoroethane into the title compound (6 mg, 4%) which was obtained as a light brown solid. MS m/z: 286.4 [M+H]⁺

Example 19

[2-(2,3-Dihydro-benzo[1,4]dioxin-6-yl)-imidazo[1,2-a]pyridin-7-yl]-methyl-amine

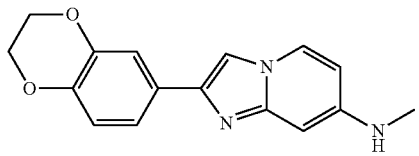 [SMILES: CNc1ccn2cc(-c3ccc4c(c3)OCCO4)nc2c1]

In analogy to the experimental procedure of example 6a) N4-methylpyridine-2,4-diamine instead of 4-bromopyridin-2-amine was converted using 2-bromo-1-(2,3-dihydrobenzo[b][1,4]dioxin-6-yl)ethanone instead of 2-bromo-1-(4-methoxyphenyl)ethanone into the title compound (327 mg, 91%) which was obtained as an off-white solid. MS m/z: 282.4 [M+H]⁺

Example 20

[2-(4-Methoxy-phenyl)-imidazo[1,2-a]pyridin-7-yl]-dimethyl-amine

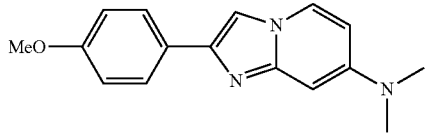

In analogy to the experimental procedure of example 5) 7-bromo-2-(4-methoxyphenyl)imidazo[1,2-a]pyridine instead of 7-bromo-2-phenylimidazo[1,2-a]pyridine was converted using dimethylamine (2 M solution in THF) instead of 4-fluoropiperidine hydrochloride into the title compound (65 mg, 37%) which was obtained as an off-white solid. MS m/z: 268.2 [M+H]⁺

Example 21

2-Benzo[1,3]dioxol-5-yl-7-[4-(2-fluoro-ethyl)-piperidin-1-yl]-imidazo[1,2-a]pyridine

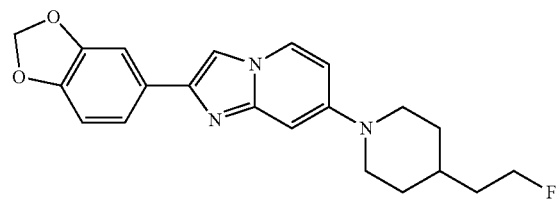 [SMILES: FCCC1CCN(c2ccn3cc(-c4ccc5c(c4)OCO5)nc3c2)CC1]

a) 2-Benzo[1,3]dioxol-5-yl-7-bromo-imidazo[1,2-a]pyridine

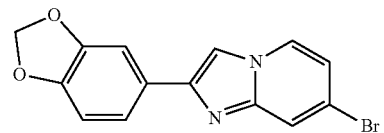 [SMILES: Brc1ccn2cc(-c3ccc4c(c3)OCO4)nc2c1]

In analogy to the experimental procedure of example 6a) 4-bromopyridin-2-amine was converted using 1-benzo[1,3]dioxol-5-yl-2-bromo-ethanone instead of 2-bromo-1-(4-methoxyphenyl)ethanone into the title compound (1.7 g, 93%) which was obtained as a white solid. MS m/z: 319.1 [M]⁺ b) 2-Benzo[1,3]dioxol-5-yl-7-[4-(2-fluoro-ethyl)-piperidin-1-yl]-imidazo[1,2-a]pyridine

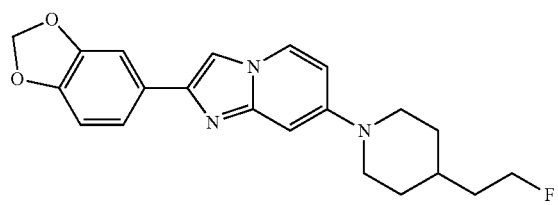 [SMILES: FCCC1CCN(c2ccn3cc(-c4ccc5c(c4)OCO5)nc3c2)CC1]

In analogy to the experimental procedure of example 5) 2-benzo[1,3]dioxol-5-yl-7-bromo-imidazo[1,2-a]pyridine instead of 7-bromo-2-phenylimidazo[1,2-a]pyridine was converted using 4-(2-fluoro-ethyl)-piperidine hydrochloride instead of 4-fluoropiperidine hydrochloride into the title compound (65 mg, 37%) which was obtained as a light yellow solid. MS m/z: 368.3 [M+H]⁺

Example 22

[2-(2,3-Dihydro-benzo[1,4]dioxin-6-yl)-imidazo[1,2-a]pyridin-7-yl]-dimethyl-amine

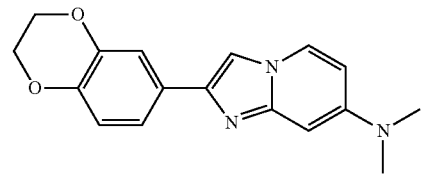 [SMILES: CN(C)c1ccn2cc(-c3ccc4c(c3)OCCO4)nc2c1]

In analogy to the experimental procedure of example 6a) N4,N4-dimethylpyridine-2,4-diamine instead of 4-bromopyridin-2-amine was converted using 2-bromo-1-(2,3-dihydrobenzo[1,4]dioxin-6-yl)ethanone instead of 2-bromo-1-(4-methoxyphenyl)ethanone into the title compound (164 mg, 47%) which was obtained as a light-grey solid. MS m/z: 296.5 [M+H]⁺

Example 23

[2-(2,3-Dihydro-benzo[1,4]dioxin-6-yl)-imidazo[1,2-a]pyridin-7-yl]-(2-fluoro-ethyl)-methyl-amine a) N4-(2-Fluoro-ethyl)-N4-methyl-pyridine-2,4-diamine

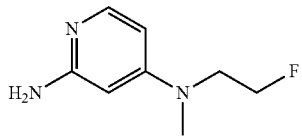

To a solution of 4-chloropyridin-2-amine (2.00 g, 15.6 mmol) and 2-fluoro-N-methylethanamine hydrochloride (2.65 g, 23.3 mmol) in sulfolane (10.0 mL) was added potassium carbonate (3.23 g, 23.3 mmol). The vessel was sealed and it was irradiated for 30 min at 180° C. in the microwave. It was poured into aqueous NaOH (1M) and extracted twice with ethyl acetate. The organic layers were washed with brine. The organic layers were combined, dried over sodium sulfate, filtrated and concentrated affording the title compound (2.1 g, 79%) as an orange liquid (15% solution in sulfolane). MS m/z: 170.4 [M+H]$^+$ b) [2-(2,3-Dihydro-benzo[14]dioxin-6-yl)-imidazo[1,2-a]pyridin-7-yl]-(2-fluoro-ethyl)-methyl-amine

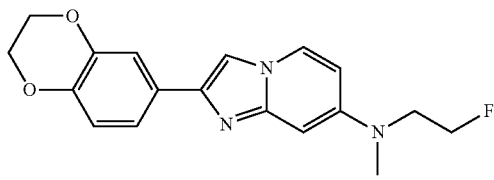 [SMILES: CN(CCF)c1ccn2cc(-c3ccc4c(c3)OCCO4)nc2c1]

In analogy to the experimental procedure of example 6a) N4-(2-fluoro-ethyl)-N4-methyl-pyridine-2,4-diamine instead of 4-bromopyridin-2-amine was converted using 2-bromo-1-(2,3-dihydrobenzo[b][1,4]dioxin-6-yl)ethanone instead of 2-bromo-1-(4-methoxyphenyl)ethanone into the title compound (100 mg, 50%) which was obtained as an off-white solid. MS m/z: 328.5 [M+H]$^+$

Example 24

7-Azetidin-1-yl-2-(4-methoxy-phenyl)-imidazo[1,2-a]pyridine

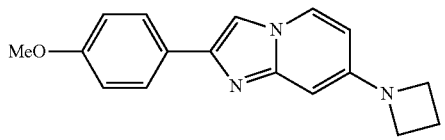 [SMILES: COc1ccc(-c2cn3ccc(N4CCC4)cc3n2)cc1]

a) 4-Azetidin-1-yl-pyridin-2-ylamine

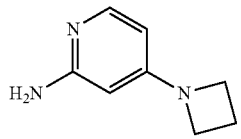 [SMILES: Nc1cc(N2CCC2)ccn1]

A microwave vial was charged with 4-chloropyridin-2-amine (0.400 g, 3.11 mmol), azetidine (847 mg, 1.0 ml, 14.8 mmol), cesium carbonate (2.03 g, 6.22 mmol) and 2.5 mL N-methyl pyrrolidone (NMP). The vial was flushed with argon and sealed. The reaction mixture was stirred at 120° C. overnight. The reaction mixture was cooled to ambient temperature and extracted with water and ethyl acetate. The aqueous layer was extracted with ethyl acetate. The organic layers were washed twice with water and once with brine. The organic layers were combined, dried over sodium sulfate, filtered and concentrated. The residue was triturated with ethyl acetate to afford the title compound (78 mg, 17%) as an off-white powder. MS m/z: 150.4 [M+H]$^+$ b) 7-Azetidin-1-yl-2-(4-methoxy-phenyl)-imidazo[1,2-a]pyridine

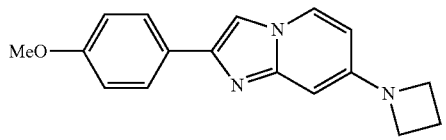 [SMILES: COc1ccc(-c2cn3ccc(N4CCC4)cc3n2)cc1]

In analogy to the experimental procedure of example 6a) 4-azetidin-1-yl-pyridin-2-ylamine instead of 4-bromopyridin-2-amine was converted using 2-bromo-1-(4-methoxyphenyl)ethanone into the title compound (41 mg, 55%) which was obtained as an off-white powder. MS m/z: 280.5 [M+H]$^+$

Example 25

N-Methyl-2-m-tolylimidazo[1,2-a]pyridin-7-amine

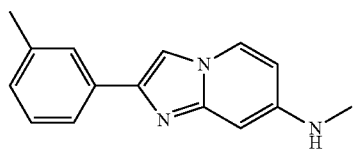 [SMILES: CNc1ccn2cc(-c3cccc(C)c3)nc2c1]

a) N4-Methyl-pyridine-2,4-diamine

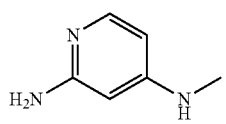

To 4-chloropyridin-2-amine (2.04 g, 15.9 mmol) was added methylamine solution, 40 wt. % in H$_2$O (4.37 g, 4.88 ml, 56.3 mmol). The vessel was sealed and it was irradiated b) N-Methyl-2-m-tolylimidazo[1,2-a]pyridin-7-amine

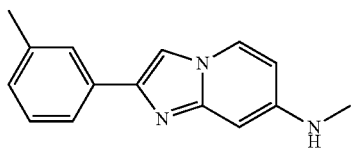 [SMILES: CNc1ccn2cc(-c3cccc(C)c3)nc2c1]

In analogy to the experimental procedure of example 6a) N4-methyl-pyridine-2,4-diamine instead of 4-bromopyridin-2-amine was converted using 2-bromo-1-m-tolylethanone instead of 2-bromo-1-(4-methoxyphenyl)ethanone into the title compound (53 mg, 26%) which was obtained as a light grey solid. MS m/z: 238.6 [M+H]$^+$

Example 26

N,N-Dimethyl-(2-m-tolyl-imidazo[1,2-a]pyridin-7-yl)-amine

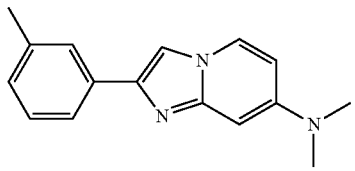 [SMILES: Cc1cccc(-c2cn3ccc(N(C)C)cc3n2)c1]

In analogy to the experimental procedure of example 6a) N4,N4-dimethyl-pyridine-2,4-diamine instead of 4-bromopyridin-2-amine was converted using 2-bromo-1-m-tolylethanone instead of 2-bromo-1-(4-methoxyphenyl)ethanone into the title compound (40 mg, 20%) which was obtained as a light yellow solid. MS m/z: 252.5 [M+H]$^+$

Example 27

N,N-Dimethyl-(2-p-tolyl-imidazo[1,2-a]pyridin-7-yl)-amine

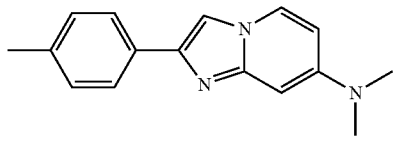

In analogy to the experimental procedure of example 6a) N4,N4-dimethyl-pyridine-2,4-diamine instead of 4-bromopyridin-2-amine was converted using 2-bromo-1-p-tolylethanone instead of 2-bromo-1-(4-methoxyphenyl)ethanone into the title compound (78 mg, 40%) which was obtained as a white solid. MS m/z: 252.5 [M+H]$^+$

Example 28

N-Methyl-(2-p-tolyl-imidazo[1,2-a]pyridin-7-yl)-amine

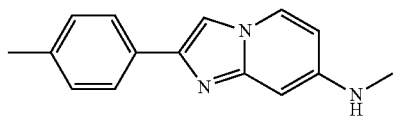

In analogy to the experimental procedure of example 6a) N4-methyl-pyridine-2,4-diamine instead of 4-bromopyridin-2-amine was converted using 2-bromo-1-p-tolylethanone instead of 2-bromo-1-(4-methoxyphenyl)ethanone into the title compound (100 mg, 51%) which was obtained as a light grey solid. MS m/z: 238.5 [M+H]$^+$

Example 29

N-(2-Fluoroethyl)-N-methyl-(2-p-tolyl-imidazo[1,2-a]pyridin-7-yl)-amine

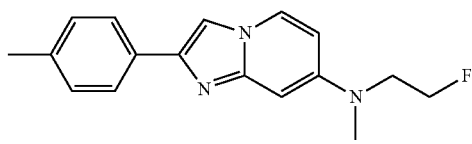 [SMILES: Cc1ccc(-c2cn3ccc(N(C)CCF)cc3n2)cc1]

In analogy to the experimental procedure of example 6a)) N4-(2-fluoro-ethyl)-N4-methyl-pyridine-2,4-diamine instead of 4-bromopyridin-2-amine was converted using 2-bromo-1-p-tolylethanone instead of 2-bromo-1-(4-methoxyphenyl)ethanone into the title compound (35 mg, 17%) which was obtained as a white solid. MS m/z: 284.6 [M+H]$^+$

Example 30

2-(4-(Dimethylamino)phenyl)-N-(2-fluoroethyl)-N-methylimidazo[1,2-a]pyridin-7-amine

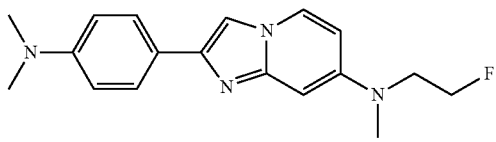 [SMILES: CN(C)c1ccc(-c2cn3ccc(N(C)CCF)cc3n2)cc1]

In analogy to the experimental procedure of example 6a)) N4-(2-fluoro-ethyl)-N4-methyl-pyridine-2,4-diamine instead of 4-bromopyridin-2-amine was converted using 2-bromo-1-(4-(dimethylamino)phenyl)ethanone instead of 2-bromo-1-(4-methoxyphenyl)ethanone into the title compound (44 mg, 28%) which was obtained as an off-white solid. MS m/z: 313.6 [M+H]$^+$

Example 31

(S)-7-(3-Fluoropyrrolidin-1-yl)-2-phenyl-imidazo[1,2-a]pyridine

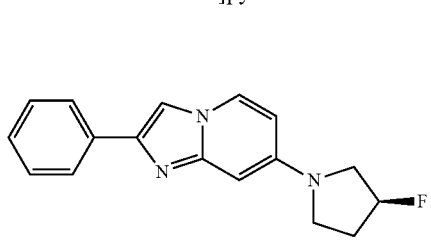

In analogy to the experimental procedure of example 5) 7-bromo-2-phenylimidazo[1,2-a]pyridine was converted using (S)-3-fluoro-pyrrolidine hydrochloride instead of 4-fluoropiperidine hydrochloride into the title compound (15 mg, 14%) which was obtained as an off-white solid. MS m/z: 282.2 [M+H]$^+$

Example 32

[2-(3-Methoxy-phenyl)-imidazo[1,2-a]pyridin-7-yl]-dimethyl-amine

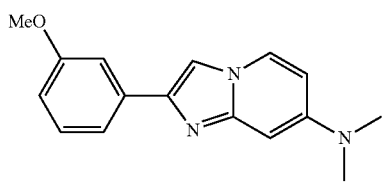 [SMILES: COc1cccc(-c2cn3ccc(N(C)C)cc3n2)c1]

In analogy to the experimental procedure of example 5) 7-bromo-2-(3-methoxy-phenyl)-imidazo[1,2-a]pyridine instead of 7-bromo-2-phenylimidazo[1,2-a]pyridine was converted using dimethylamine (2 M solution in THF) instead of 4-fluoropiperidine hydrochloride into the title compound (24 mg, 27%) which was obtained as a light green solid. MS m/z: 268.2 [M+H]$^+$

Example 33

2-(2,3-Dihydro-benzo[1,4]dioxin-6-yl)-7-[4-(2-fluoro-ethyl)-piperidin-1-yl]-imidazo[1,2-a]pyridine

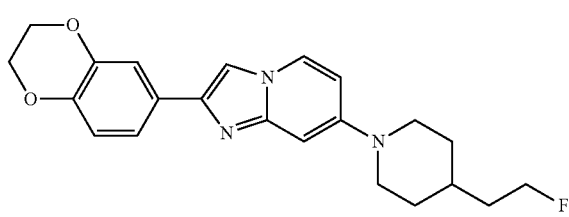 [SMILES: FCCC1CCN(c2ccn3cc(-c4ccc5c(c4)OCCO5)nc3c2)CC1]

a) 7-Bromo-2-(2,3-dihydro-benzo[1,4]dioxin-6-yl)-imidazo[1,2-a]pyridine

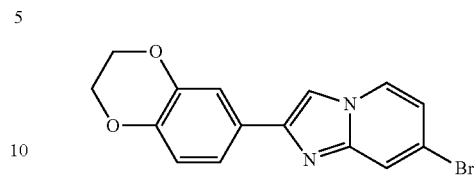

In analogy to the experimental procedure of example 6a) 4-bromopyridin-2-amine was converted using 2-bromo-1-(2,3-dihydro-benzo[1,4]dioxin-6-yl)-ethanone instead of 2-bromo-1-(4-methoxyphenyl)ethanone into the title compound (2.5 g, 87%) which was obtained as a white solid. MS m/z: 331.0 [M]$^+$ b) 2-(2,3-Dihydro-benzo[1,4]dioxin-6-yl)-7-[4-(2-fluoro-ethyl)-piperidin-1-yl]-imidazo[1,2-a]pyridine

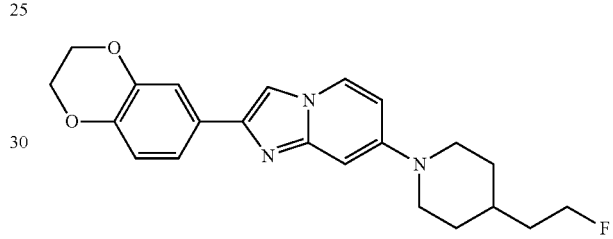

In analogy to the experimental procedure of example 5) 7-bromo-2-(2,3-dihydro-benzo[1,4]dioxin-6-yl)-imidazo[1,2-a]pyridine instead of 7-bromo-2-phenylimidazo[1,2-a]pyridine was converted using 4-(2-fluoro-ethyl)-piperidine hydrochloride instead of 4-fluoropiperidine hydrochloride into the title compound (11 mg, 6%) which was obtained as an off-white solid. MS m/z: 382.3 [M+H]$^+$

Example 34

(2-Fluoro-ethyl)-methyl-(2-m-tolyl-imidazo[1,2-a]pyridin-7-yl)-amine

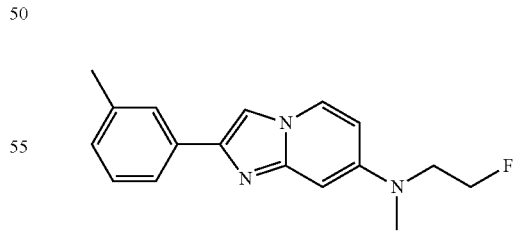

In analogy to the experimental procedure of example 6a)) N4-(2-fluoro-ethyl)-N4-methyl-pyridine-2,4-diamine instead of 4-bromopyridin-2-amine was converted using 2-bromo-1-m-tolylethanone instead of 2-bromo-1-(4-methoxyphenyl)ethanone into the title compound (92 mg, 45%) which was obtained as a white solid. MS m/z: 284.5 [M+H]$^+$

Example 35

7-Morpholin-4-yl-2-m-tolyl-imidazol[1,2-a]pyridine a) 7-Bromo-2-m-tolyl-imidazo[1,2-a]pyridine

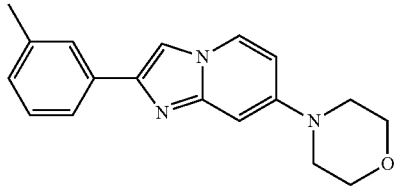 [SMILES: Cc1cccc(-c2cn3ccc(N4CCOCC4)cc3n2)c1]

In analogy to the experimental procedure of example 6a) 4-bromopyridin-2-amine was converted using 2-bromo-1-m-tolylethanone instead of 2-bromo-1-(4-methoxyphenyl)ethanone into the title compound (164 mg, 55%) which was obtained as an off-white solid. MS m/z: 287.4 [M+H]$^+$ b) 7-Morpholin-4-yl-2-m-tolyl-imidazo[1,2-a]pyridine

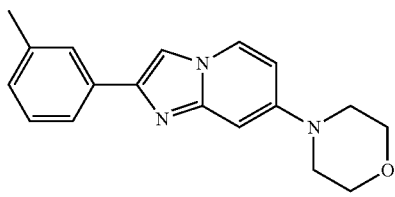 [SMILES: Cc1cccc(-c2cn3ccc(N4CCOCC4)cc3n2)c1]

In analogy to the experimental procedure of example 5) 7-bromo-2-m-tolyl-imidazo[1,2-a]pyridine instead of 7-bromo-2-phenylimidazo[1,2-a]pyridine was converted using morpholine hydrochloride instead of 4-fluoropiperidine hydrochloride into the title compound (33 mg, 20%) which was obtained as an off-white solid. MS m/z: 294.5 [M+H]$^+$

Example 36

7-Morpholin-4-yl-2-p-tolyl-imidazo[1,2-a]pyridine

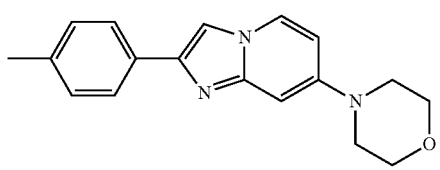 [SMILES: Cc1ccc(-c2cn3ccc(N4CCOCC4)cc3n2)cc1]

a) 7-Bromo-2-p-tolyl-imidazo[12-a]pyridine

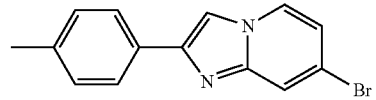 [SMILES: Cc1ccc(-c2cn3ccc(Br)cc3n2)cc1]

In analogy to the experimental procedure of example 6a) 4-bromopyridin-2-amine was converted using 2-bromo-1-p-tolylethanone instead of 2-bromo-1-(4-methoxyphenyl)ethanone into the title compound (159 mg, 61%) which was obtained as an off-white solid. MS m/z: 287.4 [M+H]$^+$ b) 7-Morpholin-4-yl-2-p-tolyl-imidazo[12-a]pyridine

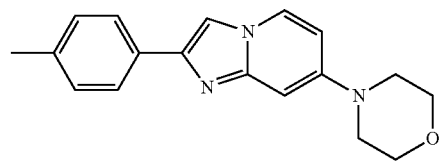 [SMILES: Cc1ccc(-c2cn3ccc(N4CCOCC4)cc3n2)cc1]

In analogy to the experimental procedure of example 5) 7-bromo-2-p-tolyl-imidazo[1,2-a]pyridine instead of 7-bromo-2-phenylimidazo[1,2-a]pyridine was converted using morpholine hydrochloride instead of 4-fluoropiperidine hydrochloride into the title compound (26 mg, 16%) which was obtained as an off-white solid. MS m/z: 294.5 [M+H]$^+$

Example 37

(2-Benzo[1,3]dioxol-5-yl-imidazo[1,2-a]pyridin-7-yl)-methyl-amine

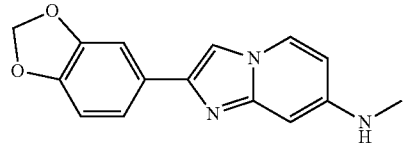 [SMILES: CNc1ccn2cc(-c3ccc4c(c3)OCO4)nc2c1]

In analogy to the experimental procedure of example 6a) N4-methyl-pyridine-2,4-diamine instead of 4-bromopyridin-2-amine was converted using 1-(benzo[1,3]dioxol-5-yl)-2-bromoethanone instead of 2-bromo-1-(4-methoxyphenyl)ethanone into the title compound (120 mg, 55%) which was obtained as an off-white solid. MS m/z: 268.4 [M+H]$^+$

Example 38

(2-Benzo[1,3]dioxol-5-yl-imidazo[1,2-a]pyridin-7-yl)-dimethyl-amine

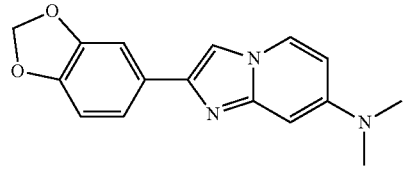 [SMILES: CN(C)c1ccn2cc(-c3ccc4c(c3)OCO4)nc2c1]

In analogy to the experimental procedure of example 6a) N4,N4-dimethyl-pyridine-2,4-diamine instead of 4-bromopyridin-2-amine was converted using 1-(benzo[1,3]dioxol-5-yl)-2-bromoethanone instead of 2-bromo-1-(4-methoxyphenyl)ethanone into the title compound (170 mg, 97%) which was obtained as an off-white solid. MS m/z: 282.5 [M+H]+

Example 39

(2-Benzo[1,3]dioxol-5-yl-imidazo[1,2-a]pyridin-7-yl)-(2-fluoro-ethyl)-methyl-amine

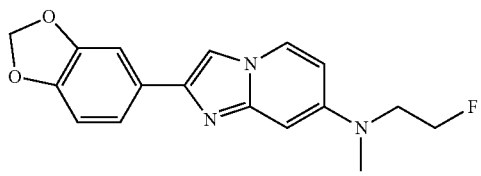 [SMILES: CN(CCF)c1ccn2cc(-c3ccc4c(c3)OCO4)nc2c1]

In analogy to the experimental procedure of example 6a) N4-(2-fluoroethyl)-N4-methylpyridine-2,4-diamine instead of 4-bromopyridin-2-amine was converted using 1-(benzo[d][1,3]dioxol-5-yl)-2-bromoethanone instead of 2-bromo-1-(4-methoxyphenyl)ethanone into the title compound (189 mg, 96%) which was obtained as an off-white solid. MS m/z: 314.5 [M+H]+

Example 40

4-(7-Azetidin-1-yl-imidazo[1,2-a]pyridin-2-yl)-phenol

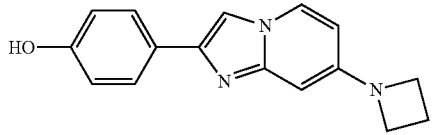 [SMILES: Oc1ccc(-c2cn3ccc(N4CCC4)cc3n2)cc1]

In analogy to the experimental procedure of example 6a) 4-(azetidin-1-yl)pyridin-2-amine instead of 4-bromopyridin-2-amine was converted using 2-bromo-1-(4-hydroxyphenyl)ethanone instead of 2-bromo-1-(4-methoxyphenyl)ethanone into the title compound (41 mg, 81%) which was obtained as a light yellow solid. MS m/z: 266.5 [M+H]+

Example 41

{4-[7-(4-Fluoro-piperidin-1-yl)-imidazo[1,2-a]pyridin-2-yl]-phenyl}-dimethyl-amine

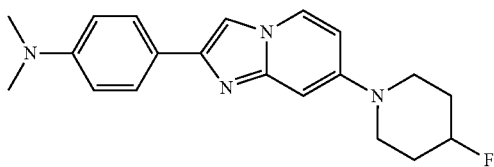 [SMILES: CN(C)c1ccc(-c2cn3ccc(N4CCC(F)CC4)cc3n2)cc1]

a) [4-(7-Bromo-imidazo[12-a]pyridin-2-yl)-phenyl]-dimethyl-amine

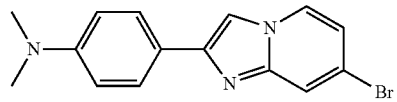 [SMILES: CN(C)c1ccc(-c2cn3ccc(Br)cc3n2)cc1]

In analogy to the experimental procedure of example 6a) 4-bromopyridin-2-amine was converted using 2-bromo-1-(4-(dimethylamino)phenyl)ethanone instead of 2-bromo-1-(4-methoxyphenyl)ethanone into the title compound (141 mg, 61%) which was obtained as an off-white solid. MS m/z: 316.4 [M]+ b) {4-[7-(4-Fluoro-piperidin-1-yl)-imidazo[1,2-a]pyridin-2-yl]-phenyl}-dimethyl-amine

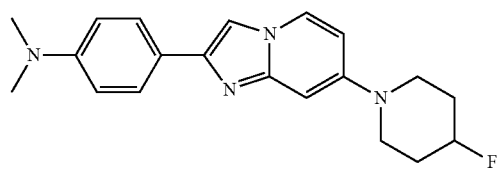 [SMILES: CN(C)c1ccc(-c2cn3ccc(N4CCC(F)CC4)cc3n2)cc1]

In analogy to the experimental procedure of example 5) [4-(7-bromo-imidazo[1,2-a]pyridin-2-yl)-phenyl]-dimethyl-amine instead of 7-bromo-2-phenylimidazo[1,2-a]pyridine was converted using 4-fluoropiperidine hydrochloride into the title compound (13 mg, 10%) which was obtained as a light yellow solid. MS m/z: 339.5 [M+H]+

Example 42

7-((R)-3-Fluoro-pyrrolidin-1-yl)-2-phenyl-imidazo[1,2-a]pyridine

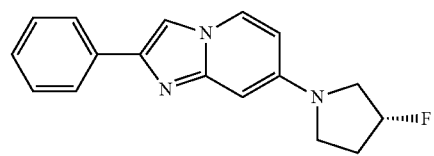 [SMILES: F[C@@H]1CCN(c2ccn3cc(-c4ccccc4)nc3c2)C1]

In analogy to the experimental procedure of example 5) 7-bromo-2-phenylimidazo[1,2-a]pyridine was converted using (R)-3-fluoro-pyrrolidine hydrochloride instead of 4-fluoropiperidine hydrochloride into the title compound (9 mg, 6%) which was obtained as an off-white solid. MS m/z: 282.0 [M+H]+

Example 43

7-((R)-3-Methoxy-pyrrolidin-1-yl)-2-phenyl-imidazo[1,2-a]pyridine

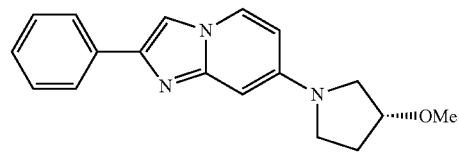 [SMILES: CO[C@@H]1CCN(c2ccn3cc(-c4ccccc4)nc3c2)C1]

In analogy to the experimental procedure of example 5) 7-bromo-2-phenylimidazo[1,2-a]pyridine was converted using (R)-3-methoxy-pyrrolidine hydrochloride instead of 4-fluoropiperidine hydrochloride into the title compound (35 mg, 22%) which was obtained as an off-white solid. MS m/z: 294.0 [M+H]⁺

Example 44

[2-(3-Methoxy-phenyl)-imidazo[1,2-a]pyridin-7-yl]-methyl-amine

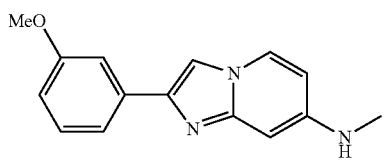 [SMILES: CNc1ccn2cc(-c3cccc(OC)c3)nc2c1]

In analogy to the experimental procedure of example 5) 7-bromo-2-(3-methoxy-phenyl)-imidazo[1,2-a]pyridine instead of 7-bromo-2-phenylimidazo[1,2-a]pyridine was converted using methylamine (2 M solution in THF) instead of 4-fluoropiperidine hydrochloride into the title compound (70 mg, 56%) which was obtained as a brown solid. MS m/z: 254.1 [M+H]⁺

Example 45

[2-(4-Fluoromethoxy-phenyl)-imidazo[1,2-a]pyridin-7-yl]-methyl-amine

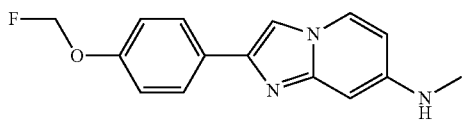 [SMILES: CNc1ccn2cc(-c3ccc(OCF)cc3)nc2c1]

a) 4-(7-Methylamino-imidazo[12-a]pyridin-2-yl)-phenol

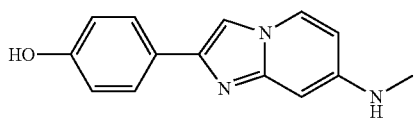 [SMILES: CNc1ccn2cc(-c3ccc(O)cc3)nc2c1]

In analogy to the experimental procedure of example 6a) N4-methylpyridine-2,4-diamine instead of 4-bromopyridin-2-amine was converted using 2-bromo-1-(4-hydroxyphenyl)ethanone instead of 2-bromo-1-(4-methoxyphenyl)ethanone into the title compound (1.36 g, 80%) which was obtained as a light yellow solid. MS m/z: 240.5 [M+H]⁺ b) [2-(4-Fluoromethoxy-phenyl)-imidazo[1,2-a]pyridin-7-yl]-methyl-amine

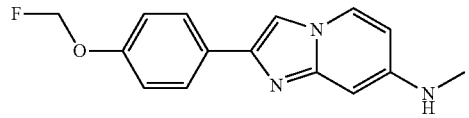

In analogy to the experimental procedure of example 17b) 4-(7-(methylamino)imidazo[1,2-a]pyridin-2-yl)phenol was converted using fluoromethyl 4-methylbenzenesulfonate instead of 1-bromo-2-fluoroethane into the title compound (232 mg, 18%) which was obtained as a light brown solid. MS m/z: 272.5 [M+H]⁺

Example 46

(2-Fluoro-ethyl)-(2-p-tolyl-imidazo[1,2-a]pyridin-7-yl)-amine

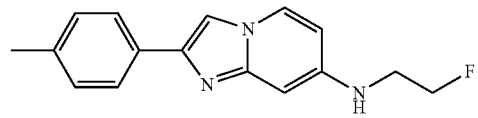 [SMILES: Cc1ccc(-c2cn3ccc(NCCF)cc3n2)cc1]

In analogy to the experimental procedure of example 5) 7-bromo-2-p-tolylimidazo[1,2-a]pyridine instead of 7-bromo-2-phenylimidazo[1,2-a]pyridine was converted using 2-fluoroethanamine hydrochloride instead of 4-fluoropiperidine hydrochloride into the title compound (38 mg, 14%) which was obtained as a light yellow solid. MS m/z: 270.5 [M+H]⁺

Example 47

(2-Fluoro-ethyl)-(2-m-tolyl-imidazo[1,2-a]pyridin-7-yl)-amine

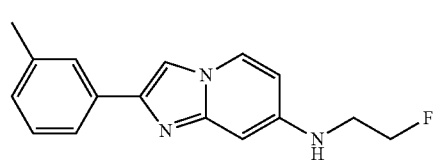 [SMILES: Cc1cccc(-c2cn3ccc(NCCF)cc3n2)c1]

In analogy to the experimental procedure of example 5) 7-bromo-2-m-tolylimidazo[1,2-a]pyridine instead of 7-bromo-2-phenylimidazo[1,2-a]pyridine was converted using 2-fluoroethanamine hydrochloride instead of 4-fluoropiperidine hydrochloride into the title compound (33 mg, 13%) which was obtained as a yellow solid. MS m/z: 270.5 [M+H]⁺

Example 48

7-((S)-3-Methoxy-pyrrolidin-1-yl)-2-m-tolyl-imidazo[1,2-a]pyridine

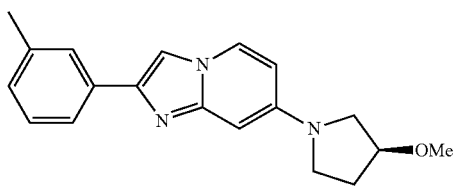 [SMILES: CO[C@H]1CCN(c2ccn3cc(-c4cccc(C)c4)nc3c2)C1]

In analogy to the experimental procedure of example 5) 7-bromo-2-m-tolyl-imidazo[1,2-a]pyridine instead of 7-bromo-2-phenylimidazo[1,2-a]pyridine was converted using (S)-3-methoxy-pyrrolidine hydrochloride instead of 4-fluoropiperidine hydrochloride into the title compound (15 mg, 7%) which was obtained as a light yellow solid. MS m/z: 308.0 [M+H]$^+$

Example 49

2-(4-Fluoromethoxy-phenyl)-7-morpholin-4-yl-imidazo[1,2-a]pyridine

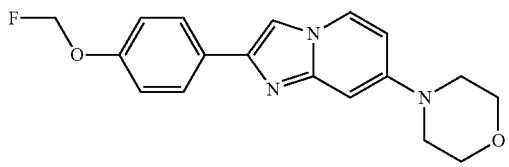 [SMILES: FCOc1ccc(-c2cn3ccc(N4CCOCC4)cc3n2)cc1]

a) 4-(7-Bromo-imidazo[1,2-a]pyridin-2-yl)-phenol

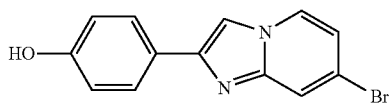

In analogy to the experimental procedure of example 6a) 4-bromopyridin-2-amine was converted using 2-bromo-1-(4-hydroxyphenyl)ethanone instead of 2-bromo-1-(4-methoxyphenyl)ethanone into the title compound (2.37 g, 80%) which was obtained as a grey solid. MS m/z: 289.3 [M]$^+$ b) 7-Bromo-2-(4-fluoromethoxy-phenyl)-imidazo[12-a]pyridine

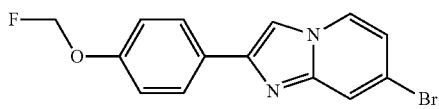 [SMILES: FCOc1ccc(-c2cn3ccc(Br)cc3n2)cc1]

In analogy to the experimental procedure of example 17b) 4-(7-bromo-imidazo[1,2-a]pyridin-2-yl)phenol instead of 4-(7-(dimethylamino)imidazo[1,2-a]pyridin-2-yl)phenol was converted using fluoromethyl 4-methylbenzenesulfonate instead of 1-bromo-2-fluoroethane into the title compound (1.69 g, 48%) which was obtained as a light brown solid. MS m/z: 321.3 [M]$^+$ c) 2-(4-Fluoromethoxy-phenyl)-7-morpholin-4-yl-imidazo[1,2-a]pyridine

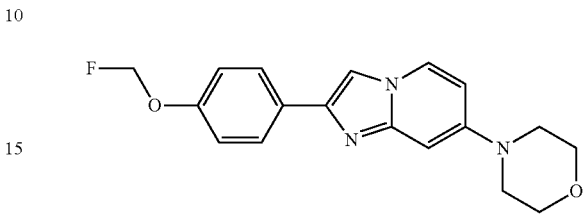

In analogy to the experimental procedure of example 5) 7-bromo-2-(4-fluoromethoxy-phenyl)-imidazo[1,2-a]pyridine instead of 7-bromo-2-phenylimidazo[1,2-a]pyridine was converted using morpholine hydrochloride instead of 4-fluoropiperidine hydrochloride into the title compound (85 mg, 41%) which was obtained as a light yellow solid. MS m/z: 328.4 [M+H]$^+$

Example 50

(2-Fluoro-ethyl)-[2-(4-fluoromethoxy-phenyl)-imidazo[1,2-a]pyridin-7-yl]-amine

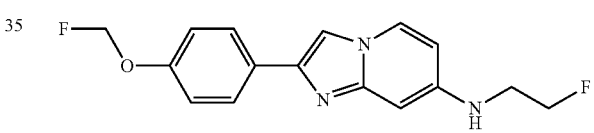

In analogy to the experimental procedure of example 5) 7-bromo-2-(4-fluoromethoxy-phenyl)-imidazo[1,2-a]pyridine instead of 7-bromo-2-phenylimidazo[1,2-a]pyridine was converted using 2-fluoroethylamine hydrochloride instead of 4-fluoropiperidine hydrochloride into the title compound (43 mg, 20%) which was obtained as a light yellow solid. MS m/z: 304.5 [M+H]$^+$

Example 51

(2-Benzo[1,3]dioxol-5-yl-imidazo[1,2-a]pyridin-7-yl)-(2-fluoro-ethyl)-amine

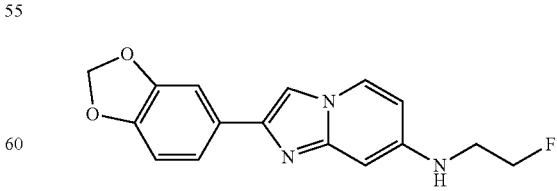

In analogy to the experimental procedure of example 6a) N4-(2-fluoroethyl)pyridine-2,4-diamine instead of 4-bromopyridin-2-amine was converted using 1-(benzo[1,3]dioxol-5-yl)-2-bromoethanone instead of 2-bromo-1-(4-

Example 52

[2-(3,4-Dimethyl-phenyl)-imidazo[1,2-a]pyridin-7-yl]-dimethyl-amine

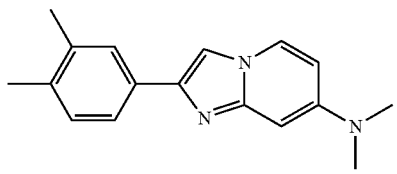

In analogy to the experimental procedure of example 6a) N4,N4-dimethylpyridine-2,4-diamine instead of 4-bromopyridin-2-amine was converted using 2-bromo-1-(3,4-dimethylphenyl)ethanone instead of 2-bromo-1-(4-methoxyphenyl)ethanone into the title compound (220 mg, 94%) which was obtained as an off-white solid. MS m/z: 266.5 [M+H]+

Example 53

[2-(3,4-Dimethyl-phenyl)-imidazo[1,2-a]pyridin-7-yl]-methyl-amine

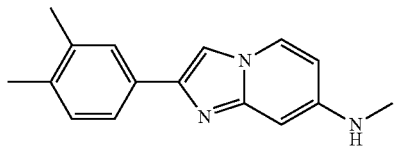

In analogy to the experimental procedure of example 6a) N4-methylpyridine-2,4-diamine instead of 4-bromopyridin-2-amine was converted using 2-bromo-1-(3,4-dimethylphenyl)ethanone instead of 2-bromo-1-(4-methoxyphenyl)ethanone into the title compound (107 mg, 65%) which was obtained as an off-white solid. MS m/z: 252.5 [M+H]+

Example 54

7-Azetidin-1-yl-2-p-tolyl-imidazo[1,2-a]pyridine

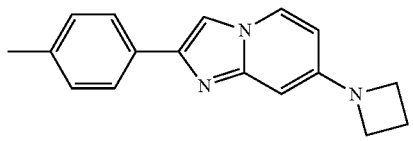 [SMILES: Cc1ccc(-c2cn3ccc(N4CCC4)cc3n2)cc1]

In analogy to the experimental procedure of example 6a) 4-(azetidin-1-yl)pyridin-2-amine instead of 4-bromopyridin-2-amine was converted using 2-bromo-1-p-tolylethanone instead of 2-bromo-1-(4-methoxyphenyl)ethanone into the title compound (107 mg, 65%) which was obtained as a light yellow solid. MS m/z: 264.5 [M+H]+

Example 55

7-Azetidin-1-yl-2-m-tolyl-imidazo[1,2-a]pyridine

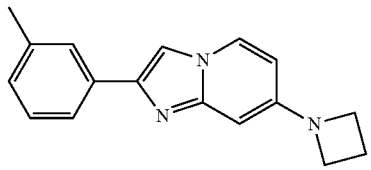 [SMILES: Cc1cccc(-c2cn3ccc(N4CCC4)cc3n2)c1]

In analogy to the experimental procedure of example 6a) 4-(azetidin-1-yl)pyridin-2-amine instead of 4-bromopyridin-2-amine was converted using 2-bromo-1-m-tolylethanone instead of 2-bromo-1-(4-methoxyphenyl)ethanone into the title compound (106 mg, 27%) which was obtained as a light brown solid. MS m/z: 264.5 [M+H]+

Example 56

7-((R)-3-Methoxy-pyrrolidin-1-yl)-2-p-tolyl-imidazo[1,2-a]pyridine

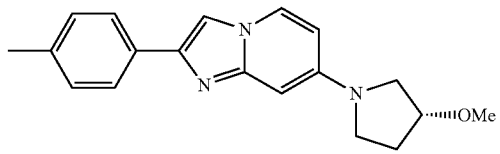 [SMILES: CO[C@@H]1CCN(c2ccn3cc(-c4ccc(C)cc4)nc3c2)C1]

In analogy to the experimental procedure of example 5) 7-bromo-2-p-tolyl-imidazo[1,2-a]pyridine instead of 7-bromo-2-phenylimidazo[1,2-a]pyridine was converted using (R)-3-methoxy-pyrrolidine hydrochloride instead of 4-fluoropiperidine hydrochloride into the title compound (4 mg, 2%) which was obtained as a white solid. MS m/z: 308.0 [M+H]+

Example 57

7-(4-Fluoro-piperidin-1-yl)-2-p-tolyl-imidazo[1,2-a]pyridine

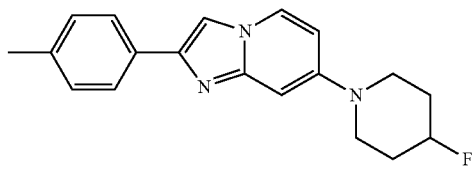 [SMILES: Cc1ccc(-c2cn3ccc(N4CCC(F)CC4)cc3n2)cc1]

In analogy to the experimental procedure of example 5) 7-bromo-2-p-tolyl-imidazo[1,2-a]pyridine instead of 7-bromo-2-phenylimidazo[1,2-a]pyridine was converted using 4-fluoropiperidine hydrochloride into the title compound (7 mg, 3%) which was obtained as an off-white solid. MS m/z: 310.2 [M+H]+

(Example 51 cont.) methoxyphenyl)ethanone into the title compound (31 mg, 17%) which was obtained as an off-white solid. MS m/z: 300.4 [M]+

Example 58

7-[4-(2-Fluoro-ethyl)-piperidin-1-yl]-2-phenyl-imidazo[1,2-a]pyridine

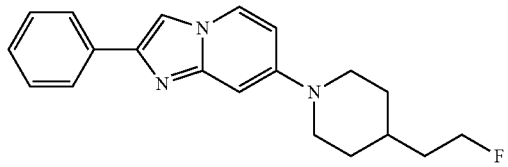 [SMILES: FCCC1CCN(c2ccn3cc(-c4ccccc4)nc3c2)CC1]

In analogy to the experimental procedure of example 5) 7-bromo-2-phenylimidazo[1,2-a]pyridine was converted using 4-(2-fluoro-ethyl)-piperidine hydrochloride instead of 4-fluoropiperidine hydrochloride into the title compound (6 mg, 3%) which was obtained as a light yellow solid. MS m/z: 324.4 [M+H]$^+$

Example 59

7-((S)-3-Methoxy-pyrrolidin-1-yl)-2-phenyl-imidazo[1,2-a]pyridine

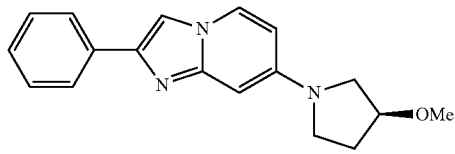 [SMILES: CO[C@H]1CCN(c2ccn3cc(-c4ccccc4)nc3c2)C1]

In analogy to the experimental procedure of example 5) 7-bromo-2-phenylimidazo[1,2-a]pyridine was converted using (S)-3-methoxy-pyrrolidine hydrochloride instead of 4-fluoropiperidine hydrochloride into the title compound (12 mg, 11%) which was obtained as a green solid. MS m/z: 294.0 [M+H]$^+$

Example 60

7-(4-Fluoro-piperidin-1-yl)-2-(3-methoxy-phenyl)-imidazo[1,2-a]pyridine

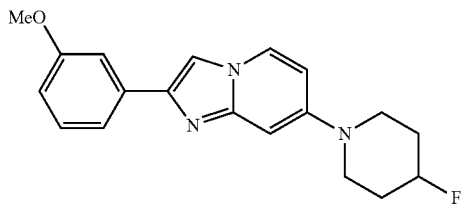 [SMILES: COc1cccc(-c2cn3ccc(N4CCC(F)CC4)cc3n2)c1]

In analogy to the experimental procedure of example 5) 7-bromo-2-(3-methoxy-phenyl)-imidazo[1,2-a]pyridine instead of 7-bromo-2-phenylimidazo[1,2-a]pyridine was converted using 4-fluoropiperidine hydrochloride into the title compound (26 mg, 12%) which was obtained as an off-white solid. MS m/z: 326.0 [M+H]$^+$

Example 61

[$^3$H]-[2-(4-Fluoromethoxy-phenyl)-imidazo[1,2-a]pyridin-7-yl]-methyl-amine

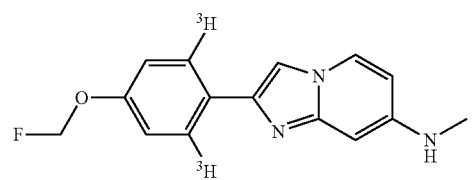 [SMILES: [3H]c1cc(OCF)cc([3H])c1-c1cn2ccc(NC)cc2n1]

In a 2 ml tritiation flask, [2-(4-fluoromethoxy-phenyl)-imidazo[1,2-a]pyridin-7-yl]-methyl-amine (2.0 mg, 7.4 µmol) and Crabtree's catalyst (8.9 mg, 11.1 µmol) were dissolved in dichloromethane (0.9 ml) and DMF (0.1 ml). The flask was attached to the tritium manifold (RC-TRITEC) and degassed by freeze-pump-thaw. Tritium gas was introduced, and the light orange solution was vigorously stirred for 4 hours in an atmosphere of tritium at 1000 mbar. The solution was cooled by liquid nitrogen and the excess tritium gas in the reaction vessel was reabsorbed on a uranium-trap for waste-tritium. The solvent was lyophilized off and labile tritium was removed by lyophilization with a 9:1-mixture of ethanol and water (3×1 ml) and toluene (2×1 ml). The remaining brownish oil was dissolved in ethanol (1.5 ml) and transferred on a SCX-2 cation exchanger. Remaining catalyst was eluted with MeOH/CH$_2$Cl$_2$ (3:1, 30 ml) and discarded, the product was eluted with NH$_3$ in MeOH (1 N)/CH$_2$Cl$_2$ (1:1, 30 ml), collected separately, and concentrated under reduced pressure. The crude product was purified by preparative HPLC (XBridge Prep, 5 µm, 10×250 mm) using acetonitrile, water, and pH 10 buffer as eluent. 555 MBq (15 mCi) were obtained of the title compound with a radiochemical purity of 95% and a specific activity of 1.81 TBq/mmol (49 Ci/mmol), determined by MS spectrometry. The compound was stored as an ethanolic solution. MS m/z: 276.2 [M+H]$^+$

Example 62

[$^3$H]—N-methyl-2-phenyl-imidazo[1,2-a]pyridin-7-amine

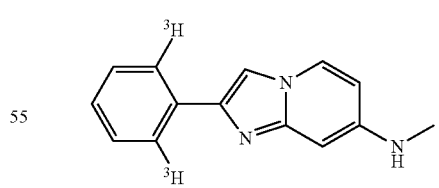

In a 2 ml tritiation flask, N-methyl-2-phenyl-imidazo[1,2-a]pyridin-7-amine (1.9 mg, 8.6 µmol) and Crabtree's catalyst (7.4 mg, 9.2 µmol) were dissolved in dichloromethane (0.9 ml) and DMSO (0.1 ml). The reaction and the purification were performed in analogy to example 61 to provide 4.9 GBq (133 mCi) of the desired compound with a radiochemical purity of 97% and a specific activity of 1.85 TBq/mmol (50 Ci/mmol). MS m/z: 228.2 [M+H]$^+$

Example 63

[³H]—N-(2-Fluoroethyl)-2-phenyl)-2-phenyl-imidazo[1,2-a]pyridin-7-amine

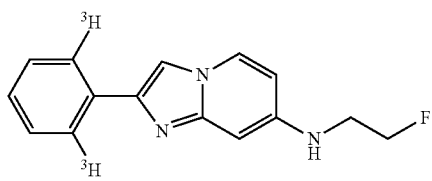 [SMILES: [3H]c1cccc([3H])c1-c1cn2ccc(NCCF)cc2n1]

In a 2 ml tritiation flask, N-(2-fluoroethyl)-2-phenyl-imidazo[1,2-a]pyridin-7-amine (2.0 mg, 7.8 µmol) and Crabtree's catalyst (9.6 mg, 12 µmol) were dissolved in dichloromethane (1.0 ml). The reaction and the purification were performed in analogy to example 61 to provide 1.5 GBq (40 mCi) of the desired compound with a radiochemical purity of 96% and a specific activity of 1.96 TBq/mmol (52.9 Ci/mmol). MS m/z: 260.2 [M+H]⁺

Example 64

[³H]—N-Methyl-(2-p-tolyl-imidazo[1,2-a]pyridin-7-yl)-amine

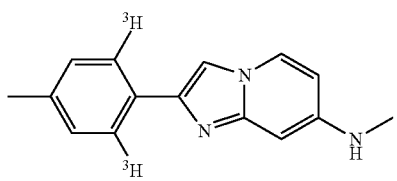

In a 2 ml tritiation flask, N-methyl-(2-p-tolyl-imidazo[1,2-a]pyridin-7-yl)-amine (2.0 mg, 8.4 µmol) and Crabtree's catalyst (6.8 mg, 8.4 µmol) were dissolved in dichloromethane (0.9 ml) and DMSO (0.1 ml). The reaction and the purification were performed in analogy to experiment of example 61 to provide 2.6 GBq (71 mCi) of the desired compound with a radiochemical purity of 98% and a specific activity of 1.72 TBq/mmol (46.6 Ci/mmol). MS m/z: 242.1 [M+H]⁺

Example 65

(2-Fluoro-ethyl)-[2-(4-methoxy-phenyl)-imidazo[1,2-a]pyridin-7-yl]-methyl-amine

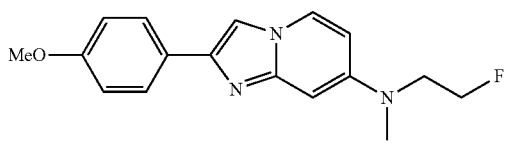 [SMILES: COc1ccc(-c2cn3ccc(N(C)CCF)cc3n2)cc1]

In analogy to the experimental procedure of example 5) 7-bromo-2-(4-methoxy-phenyl)-imidazo[1,2-a]pyridine instead of 7-bromo-2-phenylimidazo[1,2-a]pyridine was converted using (2-fluoro-ethyl)-methyl-amine hydrochloride instead of 4-fluoropiperidine hydrochloride into the title compound (20 mg, 20%) which was obtained as an off-white solid. MS m/z: 300.0 [M+H]⁺

Example 66

[2-(3,4-Dimethoxy-phenyl)-imidazo[1,2-a]pyridin-7-yl]-methyl-amine

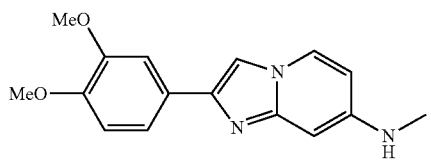 [SMILES: CNc1ccn2cc(-c3ccc(OC)c(OC)c3)nc2c1]

In analogy to the experimental procedure of example 6a) N4-methylpyridine-2,4-diamine instead of 4-bromopyridin-2-amine was converted using 2-bromo-1-(3,4-dimethoxy-phenyl)ethanone instead of 2-bromo-1-(4-methoxyphenyl)ethanone into the title compound (60 mg, 55%) which was obtained as an orange solid. MS m/z: 284.5 [M+H]⁺

Example 67

Cyclopropyl-[2-(4-methoxy-phenyl)-imidazo[1,2-a]pyridin-7-yl]-amine

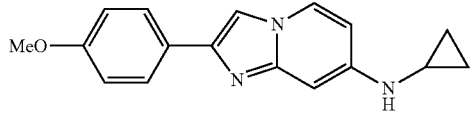 [SMILES: COc1ccc(-c2cn3ccc(NC4CC4)cc3n2)cc1]

a) N4-Cyclopropyl-pyridine-2,4-diamine

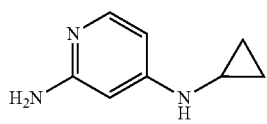

4-Chloropyridin-2-amine (400 mg, 3.11 mmol) was added to 1.6 ml water. HCl (4 M in dioxane, 0.86 ml, 3.44 mmol) was added dropwise (exothermic) followed by dropwise addition of cyclopropylamine (194 mg, 3.4 mmol). The vial was flushed with Argon, sealed and heated at 170° C. for 30 min under microwave irradiation. The reaction mixture was extracted with dichloromethane and aqueous NaOH (2M). The aqueous layer was extracted with dichloromethane. The organic layers were combined, dried over sodium sulfate, filtered and concentrated. The resulting residue (yellow solid) was triturated with ethyl acetate to afford the title compound (135 mg, 29% yield) as a light yellow solid. MS m/z: 150.3 [M+H]⁺ b) Cyclopropyl-[2-(4-methoxy-phenyl)-imidazo[1,2-a]pyridin-7-yl]-amine

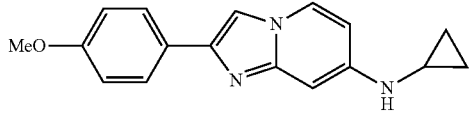

In analogy to the experimental procedure of example 6a) N4-cyclopropyl-pyridine-2,4-diamine instead of 4-bromopyridin-2-amine was converted using 2-bromo-1-(4-methoxyphenyl)ethanone into the title compound (52 mg, 53%) which was obtained as a light yellow foam. MS m/z: 280.5 [M+H]$^+$ Example 68

2-Benzo[1,3]dioxol-5-yl-7-(4-fluoro-piperidin-1-yl)-imidazo[1,2-a]pyridine

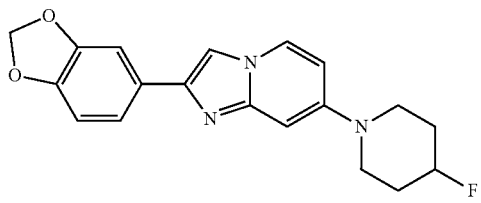 [SMILES: FC1CCN(c2ccn3cc(-c4ccc5c(c4)OCO5)nc3c2)CC1]

In analogy to the experimental procedure of example 5) 2-benzo[1,3]dioxol-5-yl-7-bromo-imidazo[1,2-a]pyridine instead of 7-bromo-2-phenylimidazo[1,2-a]pyridine was converted using 4-fluoropiperidine hydrochloride into the title compound (70 mg, 33%) which was obtained as an off-white solid. MS m/z: 340.0 [M+H]$^+$ Example 69

7-(4-Fluoro-piperidin-1-yl)-2-m-tolyl-imidazo[1,2-a]pyridine

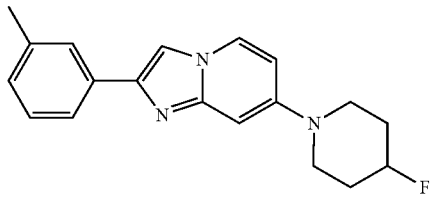 [SMILES: Cc1cccc(-c2cn3ccc(N4CCC(F)CC4)cc3n2)c1]

In analogy to the experimental procedure of example 5) 7-bromo-2-m-tolyl-imidazo[1,2-a]pyridine instead of 7-bromo-2-phenylimidazo[1,2-a]pyridine was converted using 4-fluoropiperidine hydrochloride into the title compound (27 mg, 12%) which was obtained as an off-white solid. MS m/z: 310.2 [M+H]$^+$ Example 70

7-Azetidin-1-yl-2-(4-fluoromethoxy-phenyl)-imidazo[1,2-a]pyridine

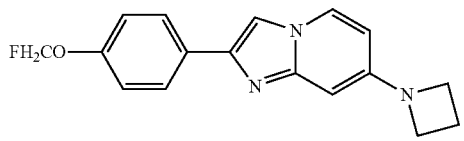

In analogy to the experimental procedure of example 17b) 4-(7-(azetidin-1-yl)imidazo[1,2-a]pyridin-2-yl)phenol instead of 4-(7-(dimethylamino)imidazo[1,2-a]pyridin-2-yl)phenol was converted using fluoromethyl 4-methylbenzenesulfonate instead of 1-bromo-2-fluoroethane into the title compound (28 mg, 19%) which was obtained as an off-white solid. MS m/z: 298.4 [M]$^+$ Example 71

Methyl-[2-(4-methylsulfanyl-phenyl)-imidazo[1,2-a]pyridin-7-yl]-amine

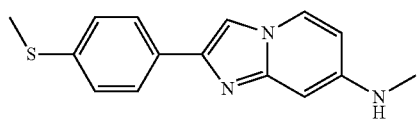

In analogy to the experimental procedure of example 6a) N4-methylpyridine-2,4-diamine instead of 4-bromopyridin-2-amine was converted using 2-bromo-1-(4-(methylthio)phenyl)ethanone instead of 2-bromo-1-(4-methoxyphenyl)ethanone into the title compound (17 mg, 15%) which was obtained as an orange solid. MS m/z: 270.4 [M+H]$^+$ Example 72

[2-(3,4-Dimethyl-phenyl)-imidazo[1,2-a]pyridin-7-yl]-(2-fluoro-ethyl)-amine

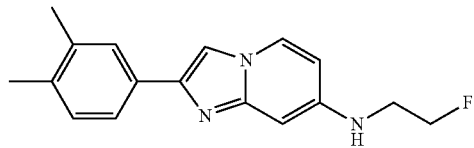 [SMILES: Cc1ccc(-c2cn3ccc(NCCF)cc3n2)cc1C]

In analogy to the experimental procedure of example 6a) N4-(2-fluoroethyl)pyridine-2,4-diamine instead of 4-bromopyridin-2-amine was converted using 2-bromo-1-(3,4-dimethylphenyl)ethanone instead of 2-bromo-1-(4-methoxyphenyl)ethanone into the title compound (33 mg, 17%) which was obtained as an off-white solid. MS m/z: 284.5 [M+H]$^+$

Example 73

[2-(3,4-Dimethoxy-phenyl)-imidazo[1,2-a]pyridin-7-yl]-(2-fluoro-ethyl)-amine

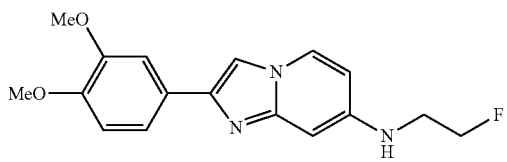 [SMILES: COc1ccc(-c2cn3ccc(NCCF)cc3n2)cc1OC]

In analogy to the experimental procedure of example 6a) N4-(2-fluoroethyl)pyridine-2,4-diamine instead of 4-bromopyridin-2-amine was converted using 2-bromo-1-(3,4-dimethoxyphenyl)ethanone instead of 2-bromo-1-(4-methoxyphenyl)ethanone into the title compound (9 mg, 7%) which was obtained as an off-white solid. MS m/z: 316.5 [M+H]$^+$

Example 74

[2-(4-Methoxy-phenyl)-imidazo[1,2-a]pyridin-7-yl]-methyl-amine

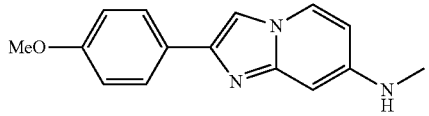 [SMILES: CNc1ccn2cc(-c3ccc(OC)cc3)nc2c1]

In analogy to the experimental procedure of example 5) 7-bromo-2-(4-methoxy-phenyl)-imidazo[1,2-a]pyridine instead of 7-bromo-2-phenylimidazo[1,2-a]pyridine was converted using methylamine (2M solution in THF) instead of 4-fluoropiperidine hydrochloride into the title compound (26 mg, 15%) which was obtained as an off-white solid. MS m/z: 253.8 [M+H]$^+$

Example 75

(2-Fluoro-ethyl)-[2-(4-methoxy-phenyl)-imidazo[1,2-a]pyridin-7-yl]-amine

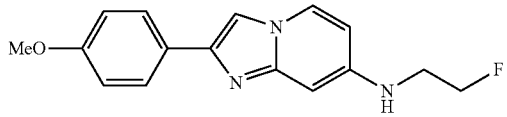 [SMILES: COc1ccc(-c2cn3ccc(NCCF)cc3n2)cc1]

In analogy to the experimental procedure of example 5) 7-bromo-2-(4-methoxy-phenyl)-imidazo[1,2-a]pyridine instead of 7-bromo-2-phenylimidazo[1,2-a]pyridine was converted using 2-fluoro-ethylamine hydrochloride instead of 4-fluoropiperidine hydrochloride into the title compound (80 mg, 34%) which was obtained as a light green solid. MS m/z: 285.8 [M+H]$^+$

Example 76

(2-Fluoro-ethyl)-[2-(3-methoxy-phenyl)-imidazo[1,2-a]pyridin-7-yl]-amine

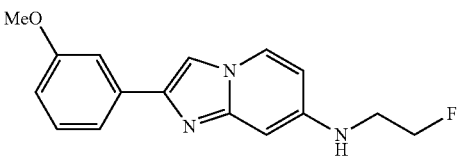 [SMILES: COc1cccc(-c2cn3ccc(NCCF)cc3n2)c1]

In analogy to the experimental procedure of example 5) 7-bromo-2-(3-methoxy-phenyl)-imidazo[1,2-a]pyridine instead of 7-bromo-2-phenylimidazo[1,2-a]pyridine was converted using 2-fluoro-ethylamine hydrochloride instead of 4-fluoropiperidine hydrochloride into the title compound (85 mg, 36%) which was obtained as an sticky off-white solid. MS m/z: 285.8 [M+H]$^+$

Example 77

7-[4-(2-Fluoro-ethyl)-piperidin-1-yl]-2-(4-methoxy-phenyl)-imidazo[1,2-a]pyridine

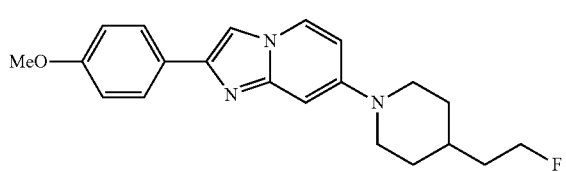

In analogy to the experimental procedure of example 5) 7-bromo-2-(4-methoxy-phenyl)-imidazo[1,2-a]pyridine instead of 7-bromo-2-phenylimidazo[1,2-a]pyridine was converted using 4-(2-fluoro-ethyl)-piperidine hydrochloride instead of 4-fluoropiperidine hydrochloride into the title compound (31 mg, 18%) which was obtained as an off-white solid. MS m/z: 353.8 [M+H]$^+$

Example 78

[2-(3-Fluoromethoxy-phenyl)-imidazo[1,2-a]pyridin-7-yl]-dimethyl-amine

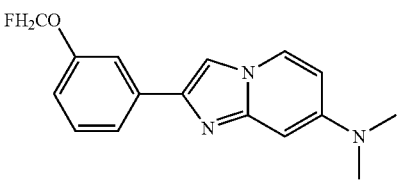

In analogy to the experimental procedure of example 17b) 3-(7-(dimethylamino)imidazo[1,2-a]pyridin-2-yl)phenol hydrobromide instead of 4-(7-(dimethylamino)imidazo[1,2-a]pyridin-2-yl)phenol was converted using fluoromethyl 4-methylbenzenesulfonate instead of 1-bromo-2-fluoroethane into the title compound (7 mg, 7%) which was obtained as a yellow solid. MS m/z: 286.5 [M]$^+$

Example 79

(2-Fluoro-ethyl)-[2-(4-methylsulfanyl-phenyl)-imidazo[1,2-a]pyridin-7-yl]-amine

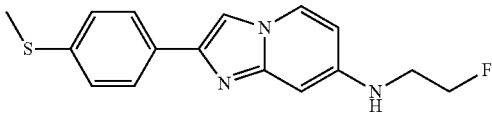 [SMILES: CSc1ccc(-c2cn3ccc(NCCF)cc3n2)cc1]

In analogy to the experimental procedure of example 6a) N4-(2-fluoroethyl)pyridine-2,4-diamine instead of 4-bromopyridin-2-amine was converted using 2-bromo-1-(4-(methylthio)phenyl)ethanone instead of 2-bromo-1-(4-methoxyphenyl)ethanone into the title compound (15 mg, 12%) which was obtained as an off-white solid. MS m/z: 302.4 [M+H]$^+$

Example 80

Cyclopropyl-[2-(4-fluoromethoxy-phenyl)-imidazo[1,2-a]pyridin-7-yl]-amine

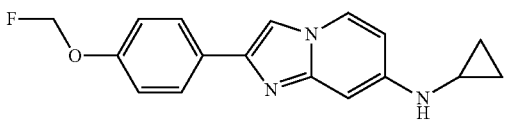

a) 4-(7-Cyclopropylamino-imidazo[1,2-a]pyridin-2-yl)-phenol

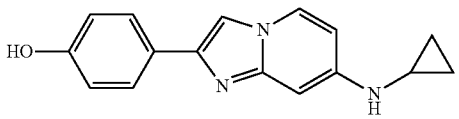 [SMILES: Oc1ccc(-c2cn3ccc(NC4CC4)cc3n2)cc1]

In analogy to the experimental procedure of example 6a) N4-cyclopropyl-pyridine-2,4-diamine instead of 4-bromopyridin-2-amine was converted using 2-bromo-1-(4-hydroxyphenyl)ethanone instead of 2-bromo-1-(4-methoxyphenyl)ethanone into the title compound (130 mg, 77%) which was obtained as a light yellow solid. MS m/z: 266.5 [M+H]$^+$ b) Cyclopropyl-[2-(4-fluoromethoxy-phenyl)-imidazo[1,2-a]pyridin-7-yl]-amine

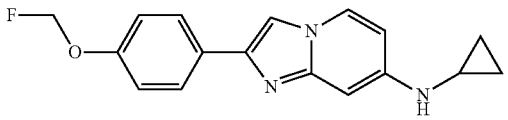

In analogy to the experimental procedure of example 17b) 4-(7-cyclopropylamino-imidazo[1,2-a]pyridin-2-yl)-phenol instead of 4-(7-(dimethylamino)imidazo[1,2-a]pyridin-2-yl) phenol was converted using fluoromethyl 4-methylbenzenesulfonate instead of 1-bromo-2-fluoroethane into the title compound (30 mg, 20%) which was obtained as a brown foam. MS m/z: 298.4 [M+H]$^+$

Example 81

2-Methoxy-4-(7-methylamino-imidazo[1,2-a]pyridin-2-yl)-phenol

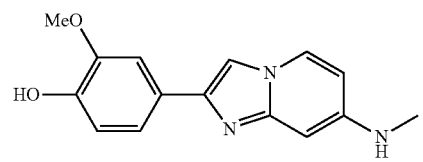 [SMILES: CNc1ccn2cc(-c3ccc(O)c(OC)c3)nc2c1]

In analogy to the experimental procedure of example 6a) N4-methylpyridine-2,4-diamine instead of 4-bromopyridin-2-amine was converted using 2-bromo-1-(4-hydroxy-3-methoxyphenyl)ethanone instead of 2-bromo-1-(4-methoxyphenyl)ethanone into the title compound (60 mg, 54%) which was obtained as a light brown solid. MS m/z: 270.5 [M+H]$^+$

Example 82

3-(7-Dimethylamino-imidazo[1,2-a]pyridin-2-yl)-phenol hydrobromide

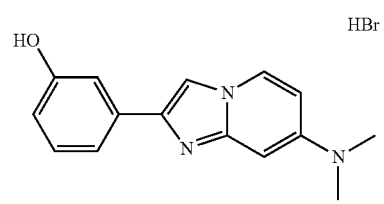 [SMILES: Br ; CN(C)c1ccn2cc(-c3cccc(O)c3)nc2c1]

In analogy to the experimental procedure of example 6a) N4,N4-dimethylpyridine-2,4-diamine instead of 4-bromopyridin-2-amine was converted using 2-bromo-1-(3-hydroxyphenyl)ethanone instead of 2-bromo-1-(4-methoxyphenyl)ethanone into the title compound (760 mg, 80%) which was obtained as an off-white solid. MS m/z: 254.5 [M+H]$^+$

Example 83

N-(2-fluoroethyl)-2-(3-methoxyphenyl)-N-methyl-imidazo[1,2-a]pyridin-7-amine, acetic acid adduct

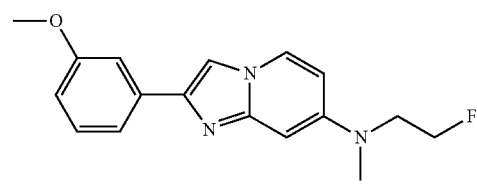

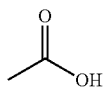

N-(2-fluoroethyl)-2-(3-methoxyphenyl)-N-methylimidazo[1,2-a]pyridin-7-amine, acetic acid adduct, was prepared following the same method adopted for the synthesis of 7-(4-fluoropiperidin-1-yl)-2-phenylimidazo[1,2-a]pyridine (example 5) from 7-bromo-2-(3-methoxy-phenyl)-imidazo[1,2-a]pyridine (100 mg, 0.33 mmol) and (2-fluoroethyl)-methyl-amine hydrochloride (93 mg, 0.825 mmol). Light yellow sticky solid (10 mg, 10%); MS m/z: 300.2 [M+H]$^+$

Example 84

2-(2, 3-Dihydro-benzo[1, 4]dioxin-6-yl)-7-(4-fluoropiperidin-1-yl)-imidazo[1,2-a]pyridine

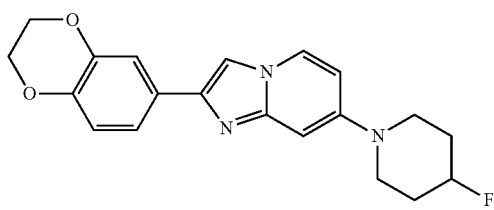 [SMILES: FC1CCN(c2ccn3cc(-c4ccc5c(c4)OCCO5)nc3c2)CC1]

2-(2,3-Dihydro-benzo[1,4]dioxin-6-yl)-7-(4-fluoro-piperidin-1-yl)-imidazo[1,2-a]pyridine was prepared in analogy to 7-(4-fluoropiperidin-1-yl)-2-phenylimidazo[1,2-a]pyridine (example 5) from 7-bromo-2-(2,3-dihydro-benzo[1,4]dioxin-6-yl)-imidazo[1,2-a]pyridine (200 mg, 0.60 mmol) and 4-fluoro-piperidine hydrochloride (211 mg, 1.51 mmol). Off-white solid (13 mg, 6%); MS m/z: 353.8 [M+H]$^+$

Example 85

7-[4-(2-Fluoro-ethyl)-piperidin-1-yl]-2-m-tolyl-imidazo[1,2-a]pyridine

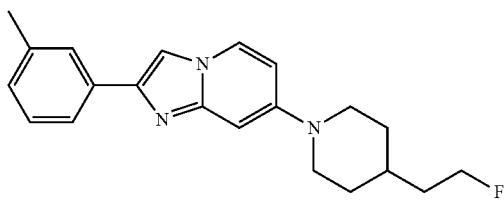 [SMILES: Cc1cccc(-c2cn3ccc(N4CCC(CCF)CC4)cc3n2)c1]

7-[4-(2-Fluoro-ethyl)-piperidin-1-yl]-2-m-tolyl-imidazo[1,2-a]pyridine was prepared in analogy to 7-(4-fluoropiperidin-1-yl)-2-phenylimidazo[1,2-a]pyridine (example 5) from 7-bromo-2-m-tolyl-imidazo[1,2-a]pyridine (150 mg, 0.52 mmol) and 4-(2-fluoro-ethyl)-piperidine hydrochloride (218 mg, 1.31 mmol). Off-white solid (20 mg, 11%); MS m/z: 337.8 [M+H]$^+$

Example 86

7-((R)-3-Methoxy-pyrrolidin-1-yl)-2-m-tolyl-imidazo[1,2-a]pyridine

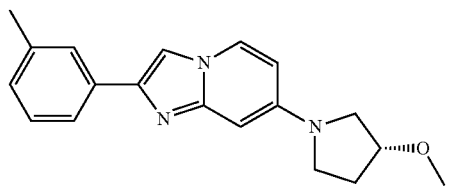 [SMILES: CO[C@@H]1CCN(c2ccn3cc(-c4cccc(C)c4)nc3c2)C1]

7-((R)-3-Methoxy-pyrrolidin-1-yl)-2-m-tolyl-imidazo[1,2-a]pyridine was prepared in analogy to 7-(4-fluoropiperidin-1-yl)-2-phenylimidazo[1,2-a]pyridine (example 5) from 7-bromo-2-m-tolyl-imidazo[1,2-a]pyridine (200 mg, 0.697 mmol) and (R)-3-methoxy-pyrrolidine hydrochloride (239 mg, 1.74 mmol). Light yellow solid (46 mg, 21%); MS m/z: 308.0 [M+H]$^+$

Example 87

7-[4-(2-Fluoro-ethyl)-piperidin-1-yl]-2-p-tolyl-imidazo[1,2-a]pyridine

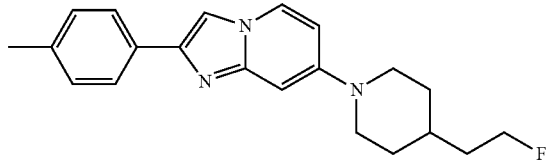 [SMILES: Cc1ccc(-c2cn3ccc(N4CCC(CCF)CC4)cc3n2)cc1]

7-[4-(2-Fluoro-ethyl)-piperidin-1-yl]-2-p-tolyl-imidazo[1,2-a]pyridine was prepared in analogy to 7-(4-fluoropiperidin-1-yl)-2-phenylimidazo[1,2-a]pyridine (example 5) from 7-bromo-2-p-tolyl-imidazo[1,2-a]pyridine (150 mg, 0.523 mmol) and 4-(2-fluoro-ethyl)-piperidine hydrochloride (218 mg, 1.31 mmol). Off-white solid (37 mg, 21%); MS m/z: 338.0 [M+H]$^+$

Example 88

7-((S)-3-Methoxy-pyrrolidin-1-yl)-2-p-tolyl-imidazo[1,2-a]pyridine

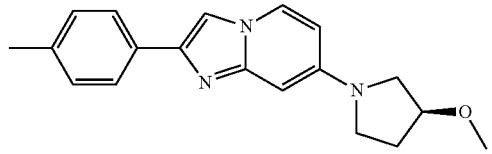

7-((S)-3-Methoxy-pyrrolidin-1-yl)-2-p-tolyl-imidazo[1,2-a]pyridine was prepared in analogy to 7-(4-fluoropiperidin-1-yl)-2-phenylimidazo[1,2-a]pyridine (example 5) from 7-bromo-2-p-tolyl-imidazo[1,2-a]pyridine (200 mg, 0.697 mmol) and (S)-3-methoxy-pyrrolidine hydrochloride (240 mg, 1.74 mmol). Off-white solid (45 mg, 21%); MS m/z: 308.0 [M+H]$^+$

Example 89

[4-[7-(Methylamino)imidazo[1,2-a]pyridin-2-yl]phenyl]methanol acetic acid adduct a) Methyl 4-[7-(methylamino)imidazo[1,2-a]pyridin-2-yl]benzoate

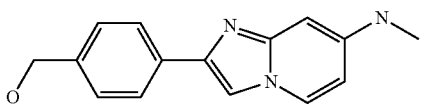 [SMILES: CNc1ccn2cc(-c3ccc(CO)cc3)nc2c1]

In analogy to the experimental procedure of example 6a) N4-methylpyridine-2,4-diamine instead of 4-bromopyridin-2-amine was converted using methyl 4-(2-bromoacetyl)benzoate instead of 2-bromo-1-(4-methoxyphenyl)ethanone into the title compound (250 mg, 55%) which was obtained as a yellow solid. MS m/z: 282.2 [M+H]$^+$ b) [4-[7-(Methylamino)imidazo[1,2-a]pyridin-2-yl]phenyl]methanol acetic acid adduct

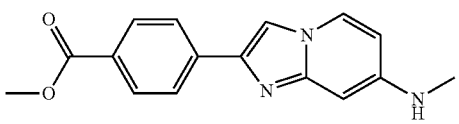

To a cold solution of compound 1 (100 mg, 0.354 mmol) in THF (10 mL), DIBAL (2M in toluene) (0.354 mL, 0.708 mmol) was added and the reaction mixture was stirred at 25° C. for 30 min. Further DIBAL (2M in toluene) (0.885 mL, 1.77 mmol) was added and stirred for 20 min at 25° C. Then reaction mixture was quenched with sat aq. NH$_4$Cl and evoporated in vaccuo. Residue was washed with 10% MeOH/dichloromethane and the filtrate evaporated. Purified by prep-HPLC afforded the title compounds (40 mg, 45%) as an off-white solid. MS m/z: 254.0 [M+H]$^+$

Example 90

[4-[7-(Dimethylamino)imidazo[1,2-a]pyridin-2-yl]phenyl]methanol acetic acid adduct

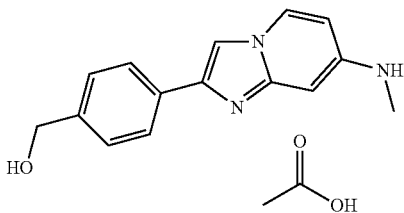

a) Methyl 4-[7-(dimethylamino)imidazo[1,2-a]pyridin-2-yl]benzoate

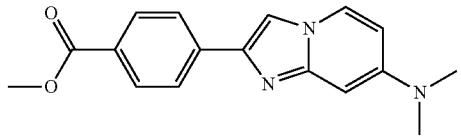

In analogy to the experimental procedure of example 6a) N4,N4-dimethylpyridine-2,4-diamine instead of 4-bromopyridin-2-amine was converted using methyl 4-(2-bromoacetyl)benzoate instead of 2-bromo-1-(4-methoxyphenyl)ethanone into the title compound (319 mg, 75%) which was obtained as a light green solid. MS m/z: 296.0 [M+H]$^+$ b) [4-[7-(Dimethylamino)imidazo[12-a]pyridin-2-yl]phenyl]methanol acetic acid adduct

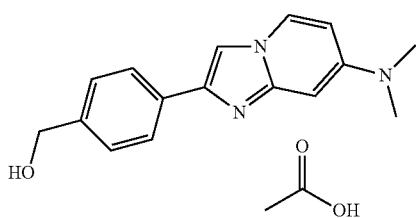

In analogy to the experimental procedure of example 89b) methyl 4-[7-(dimethylamino)imidazo[1,2-a]pyridin-2-yl]benzoate instead of methyl 4-[7-(methylamino)imidazo[1,2-a]pyridin-2-yl]benzoate was converted into the title compound (235 mg, 86%) which was obtained as a brown solid. MS m/z: 268.0 [M+H]$^+$

Example 91

7-(azetidin-1-yl)-2-(3-methoxyphenyl)imidazo[1,2-a]pyridine

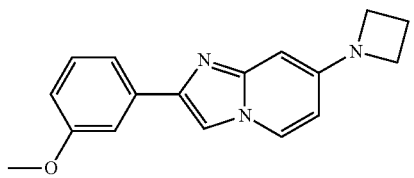 [SMILES: COc1cccc(-c2cn3ccc(N4CCC4)cc3n2)c1]

In analogy to the experimental procedure of example 6a) 4-(azetidin-1-yl)pyridin-2-amine instead of 4-bromopyridin-2-amine was converted using 2-bromo-1-(3-methoxyphenyl)ethanone instead of 2-bromo-1-(4-methoxyphenyl)ethanone into the title compound (30 mg, 28%) which was obtained as an off-white solid. MS m/z: 280.5 [M+H]$^+$

Example 92

2-(3,5-dimethoxyphenyl)-N-methylimidazo[1,2-a]pyridin-7-amine

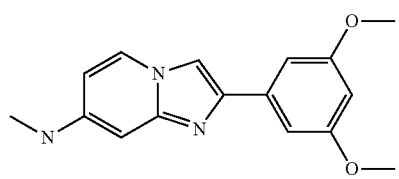

In analogy to the experimental procedure of example 6a) N4-methylpyridine-2,4-diamine instead of 4-bromopyridin-2-amine was converted using 2-bromo-1-(3,5-dimethoxyphenyl)ethanone instead of 2-bromo-1-(4-methoxyphenyl)ethanone into the title compound (27 mg, 24%) which was obtained as a light brown oil. MS m/z: 284.5 [M+H]$^+$

Example 93

N-[2-(4-Ethoxy-phenyl)-imidazo[1,2-a]pyridin-7-yl]-methyl-amine acetic acid adduct

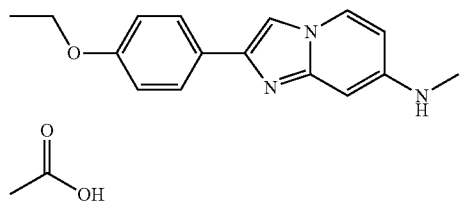

To a solution of N4-methyl-pyridine-2, 4-diamine (Example 25a) (155 mg, 1.26 mmol) in ethanol (10 ml) was added 2-bromo-1-(4-ethoxyphenyl) ethanone (459 mg, 1.89 mmol). The mixture was stirred for 30 min at 25° C. and then allowed to reflux for another 12 h under N$_2$. Volatiles were removed under reduced pressure. The crude material was purified by prep. HPLC (column: Reprosil Gold; column size & packing material: 100×30 mm, 5µ/C18, reverse phase; mobile phase: MeCN and 5 mM NH$_4$OAc in H$_2$O) to afford N-[2-(4-ethoxy-phenyl)-imidazo[1,2-a]pyridin-7-yl]-methyl-amine as acetic acid adduct. Light green sticky solid (27 mg, 8%). MS m/z: 267.8 [M+H]$^+$.

Example 94

Methyl-[2-(4-pyrrolidin-1-yl-phenyl)-imidazo[1,2-a]pyridin-7-yl]-amine acetic acid adduct

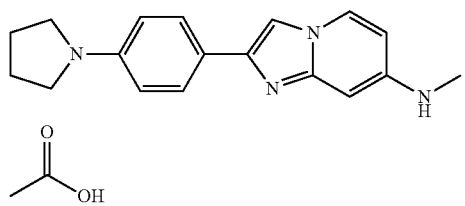

This compound was prepared following the same method as adopted for synthesis of N-[2-(4-ethoxy-phenyl)-imidazo[1,2-a]pyridin-7-yl]-methyl-amine acetic acid adduct (Example 87) from N4-methyl-pyridine-2,4-diamine (155 mg, 1.26 mmol) and alpha-bromo-4'-(1-pyrrolidino)acetophenone (505 mg, 1.89 mmol). Light green sticky solid (12 mg, 3%). MS m/z: 293.0 [M+H]$^+$.

Example 95

N-[2-(3-Fluoro-4-methoxy-phenyl)-imidazo[1,2-a]pyridin-7-yl]-methyl-amine

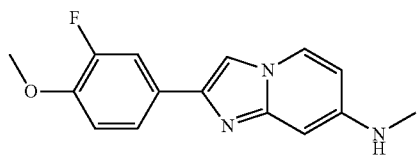

This compound was prepared following the same method as adopted for synthesis of N-[2-(4-ethoxy-phenyl)-imidazo[1,2-a]pyridin-7-yl]-methyl-amine acetic acid adduct (Example 87) from N4-methyl-pyridine-2,4-diamine (155 mg, 1.26 mmol) and 3-fluoro-4-methoxyphenacyl bromide (468 mg, 1.89 mmol). The crude material was purified by flash chromatography using amine bound silica gel (40% EtOAc/hexane). Off-white solid (35 mg, 10%). MS m/z: 272.0 [M+H]$^+$.

Example 96

N-[2-(3,4-Dihydro-2H-benzo[b][1,4]dioxepin-7-yl)-imidazo[1,2-a]pyridin-7-yl]-methyl-amine

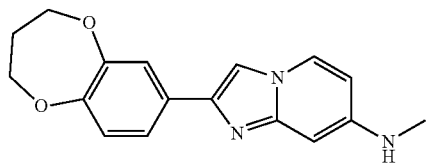 [SMILES: CNc1ccn2cc(-c3ccc4c(c3)OCCCO4)nc2c1]

This compound was prepared following the same method as adopted for synthesis of N-[2-(4-ethoxy-phenyl)-imidazo[1,2-a]pyridin-7-yl]-methyl-amine acetic acid adduct (Example 93) from N4-methyl-pyridine-2,4-diamine (152 mg, 1.23 mmol) and 2-bromo-1-(3,4-dihydro-2H-1,5-benzodioxepin-7-yl)ethan-1-one (502 mg, 1.85 mmol). The crude material was purified by flash chromatography using amine bound silica gel (50% EtOAc/hexane). Off-white solid (45 mg, 12%). MS m/z: 296.0 [M+H]$^+$.

Example 97

N-[2-(4-Diethylamino-phenyl)-imidazo[1,2-a]pyridin-7-yl]-methyl-amine

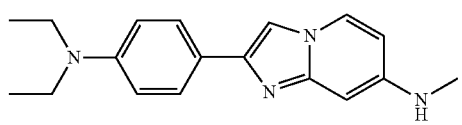 [SMILES: CCN(CC)c1ccc(-c2cn3ccc(NC)cc3n2)cc1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and alpha-bromo-4'-(diethylamino)acetophenone (493 mg, 1.83 mmol). Off-white solid (70 mg, 19%). MS m/z: 294.8 [M+H]⁺.

Example 98

N-[2-(4-Ethyl-phenyl)-imidazo[1,2-a]pyridin-7-yl]-methyl-amine

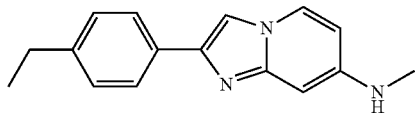 [SMILES: CCc1ccc(-c2cn3ccc(NC)cc3n2)cc1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (155 mg, 1.26 mmol) and 2-bromo-1-(4-ethylphenyl)-ethanone (429 mg, 1.89 mmol). Off-white solid (85 mg, 27%). MS m/z: 251.8 [M+H]⁺.

Example 99

2-[4-(Methoxymethyl)phenyl]-N,N-dimethyl-imidazo[1,2-a]pyridin-7-amine acetic acid adduct

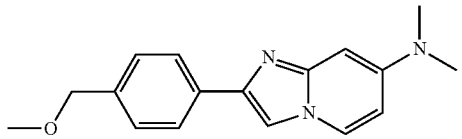

To a stirred solution of [4-[7-(dimethylamino)imidazo[1,2-a]pyridin-2-yl]phenyl]methanol (100 mg, 0.375 mmol) in DMF (3 mL), K₂CO₃ (129 mg, 0.936 mmol) and methyl iodide (0.047 ml, 0.749 mmol) were added and stirred at 25° C. for 12 h. Then reaction mixture was filtered and residue was washed with DMF. The filtrate was evaporated. Purification by prep-HPLC afforded the title compound (55 mg, 52%) as an off white solid. MS m/z: 282.0 [M+H]⁺.

Example 100

Methyl-(2-thiophen-3-yl-imidazo[1,2-a]pyridin-7-yl)-amine

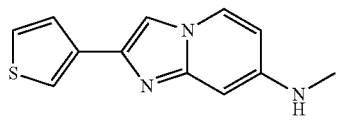 [SMILES: CNc1ccn2cc(-c3ccsc3)nc2c1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and 2-bromo-1-(3-thienyl)-1-ethanone (375 mg, 1.83 mmol). Grey solid (76 mg, 27%). MS m/z: 229.8 [M+H]⁺.

Example 101

N-(2-Furan-2-yl-imidazo[1,2-a]pyridin-7-yl)-methyl-amine

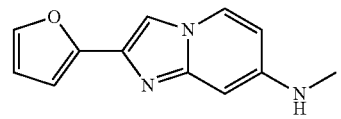

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (157 mg, 1.27 mmol) and 2-bromo-1-(2-furyl)-1-ethanone (361 mg, 1.91 mmol). Light green solid (53 mg, 19%). MS m/z: 214.0 [M+H]⁺.

Example 102

N-(2-Thiophen-2-yl-imidazo[1,2-a]pyridin-7-yl)-methyl-amine

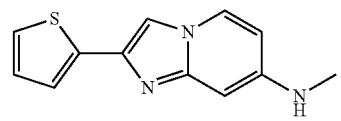

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (153 mg, 1.24 mmol) and 2-bromo-1-(2-thienyl)-1-ethanone (382 mg, 1.86 mmol). Light yellow solid (62 mg, 22%). MS m/z: 230.0 [M+H]⁺.

Example 103

Methyl-[2-(4-morpholin-4-yl-phenyl)-imidazo[1,2-a]pyridin-7-yl]-amine

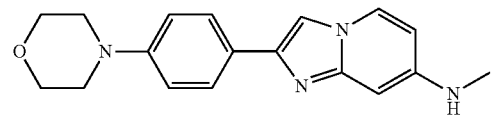 [SMILES: CNc1ccn2cc(-c3ccc(N4CCOCC4)cc3)nc2c1]

This compound was prepared following the same method as adopted for synthesis of N-[2-(3-fluoro-4-methoxy-phenyl)-imidazo[1,2-a]pyridin-7-yl]-methyl-amine (Example 89) from N4-methyl-pyridine-2,4-diamine (158 mg, 1.28 mmol) and 2-bromo-1-(4-morpholinophenyl)-1-ethanone (547 mg, 1.92 mmol). Off-white solid (68 mg, 17%). MS m/z: 309.0 [M+H]⁺.

Example 104

Methyl-(2-thiazol-2-yl-imidazo[1,2-a]pyridin-7-yl)-amine

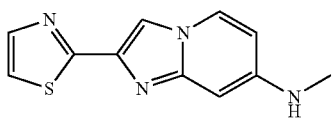 [SMILES: CNc1ccn2cc(-c3nccs3)nc2c1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and 2-bromo-1-(1,3-thiazol-2-yl)ethanone (376 mg, 1.83 mmol). Brown solid (50 mg, 18%). MS m/z: 231.0 [M+H]+.

Example 105

2-[4-(2-Fluoroethoxymethyl)phenyl]-N,N-dimethyl-imidazo[1,2-a]pyridin-7-amine

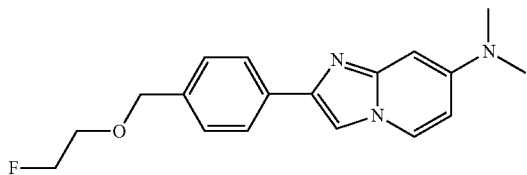 [SMILES: CN(C)c1ccn2cc(-c3ccc(COCCF)cc3)nc2c1]

To a solution of [4-[7-(dimethylamino)imidazo[1,2-a]pyridin-2-yl]phenyl]methanol (100 mg, 0.374 mmol) in dry toluene (10 mL) was added powered KOH (73.3 mg, 1.309 mmol) and nBu4NHSO4 (25.4 mg, 0.075 mmol) at 25° C. The mixture was heated to 50° C. while 1-bromo-2-fluoroethane (71.8 mg, 0.568 mmol) was added slowly with vigorous stirring. Reaction temperature was subsequently increased to 80° C. and stirring continued for another 12 h. Solvent was evaporated. Purification by prep. HPLC afforded the title compound (47 mg, 40%) as an off-white solid. MS m/z: 314.4 [M+H]+.

Example 106

7-(Azetidin-1-yl)-2-[4-(2-fluoroethoxy)phenyl]imi-dazo[1,2-a]pyridine

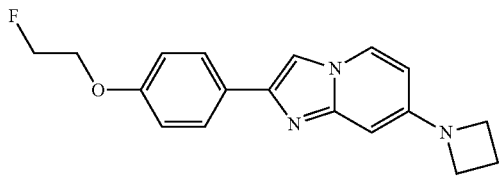 [SMILES: FCCOc1ccc(-c2cn3ccc(N4CCC4)cc3n2)cc1]

4-(7-(Azetidin-1-yl)imidazo[1,2-a]pyridin-2-yl)phenol (120 mg, 398 μmol; Example 40), 1-bromo-2-fluoroethane (70.7 mg, 557 μmol) and Cs2CO3 (259 mg, 796 μmol) were combined with DMF (2 ml) under Ar in a sealed tube. The reaction mixture was stirred at 90° C. overnight. After cooling to r.t. the mixture was diluted with CH2Cl2 and H2O. The aqueous layer (pH-9) was extracted back with CH2Cl2. The organic layers were washed three times with H2O and one time with brine. The organic layers were combined, dried over MgSO4, filtered and concentrated. The residue was triturated with EtOAc to afford 7-(azetidin-1-yl)-2-(4-(2-fluoroethoxy)phenyl)imidazo[1,2-a]pyridine (72 mg, 58%) as an off-white solid. MS m/z: 312.5 [M+H]+.

Example 107

7-(Azetidin-1-yl)-2-[3-(fluoromethoxy)phenyl]imi-dazo[1,2-a]pyridine

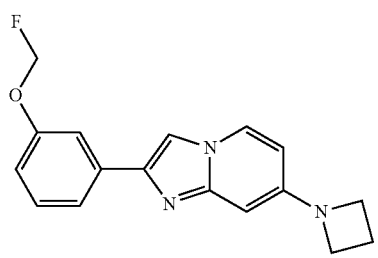 [SMILES: FCOc1cccc(-c2cn3ccc(N4CCC4)cc3n2)c1]

3-(7-(Azetidin-1-yl)imidazo[1,2-a]pyridin-2-yl)phenol (110 mg, 373 μmol; Example 95), fluoromethyl 4-methyl-benzenesulfonate (107 mg, 522 μmol) and Cs2CO3 (243 mg, 746 μmol) were combined in sealed tube with DMF (1.85 ml) under Ar. The reaction mixture was stirred at 90° C. overnight. After cooling to r.t. the mixture was diluted with CH2Cl2 and H2O. The aqueous layer (pH-9) was extracted back with CH2Cl2. The organic layers were washed three times with H2O and one time with brine. The combined organic layers were dried over MgSO4, filtered and concentrated. The crude product was dried under high vacuum overnight to remove residual DMF. The residue was absorbed on Isolute and purified by flash chromatography (10 g NH2-silica gel cartridge with heptane/EtOAc 1:1). A second chromatography was performed on a 10 g NH2-silica gel cartridge with heptane/EtOAc 0-50%. The product was then further purified by trituration with EtOAc and finally by prep. HPLC to yield 7-(azetidin-1-yl)-2-(3-(fluoromethoxy)phenyl)imidazo[1,2-a]pyridine as light yellow solid (39 mg, 34%). MS m/z: 298.1 [M+H]+.

Example 108

2-(3-methoxy-4-methylphenyl)-N-methylimidazo[1,2-a]pyridin-7-amine

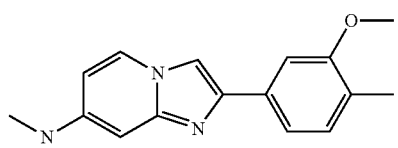

In analogy to the experimental procedure of example 6a) N4-methylpyridine-2,4-diamine instead of 4-bromopyridin-2-amine was converted using 2-bromo-1-(3-methoxy-4-methylphenyl)ethanone instead of 2-bromo-1-(4-methoxyphenyl)ethanone into the title compound (43 mg, 39%) which was obtained as a light red solid. MS m/z: 268.5 [M+H]+

Example 109

2-[4-(2-Fluoroethoxy)phenyl]-N-methylimidazo[1,2-a]pyridin-7-amine

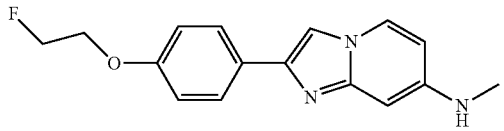 [SMILES: CNc1ccn2cc(-c3ccc(OCCF)cc3)nc2c1]

4-(7-(Methylamino)imidazo[1,2-a]pyridin-2-yl)phenol (150 mg, 627 µmol; Example 45a), 1-bromo-2-fluoroethane (111 mg, 878 µmol) and Cs$_2$CO$_3$ (409 mg, 1.25 mmol) were combined in a sealed tube with DMF (3.25 ml) under Ar. The reaction mixture was stirred at 80° C. overnight. The reaction mixture was cooled to r.t. and extracted with EtOAc and H$_2$O. The aqueous layer was extracted back with EtOAc. The organic layers were washed 3 times with H$_2$O and one time with brine. The combined organic layers were dried over MgSO$_4$, filtered and concentrated. The crude product was purified by flash chromatography (10 g SiO$_2$ cartridge with CH$_2$Cl$_2$/MeOH 0% to 5%). After two consecutive triturations with EtOAc the final product was obtained as light brown solid (10 mg, 5%). MS m/z: 286.1 [M+H]+.

Example 110

2-(4-(benzyl(methyl)amino)phenyl)-N-methylimidazo[1,2-a]pyridin-7-amine

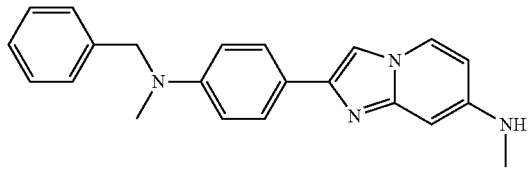

a) 2-(4-bromophenyl)-7-chloro-imidazo[1,2-a]pyridine

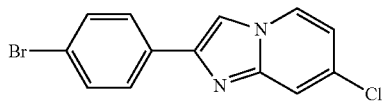 [SMILES: Clc1ccn2cc(-c3ccc(Br)cc3)nc2c1]

In analogy to the experimental procedure of example 6a) 4-chloropyridin-2-amine instead of 4-bromopyridin-2-amine was converted using 2-bromo-1-(4-bromophenyl)ethanone instead of 2-bromo-1-(4-methoxyphenyl)ethanone into the title compound (2.66 g, 73%) which was obtained as a light brown solid. MS m/z: 309.4 [M+H]+ b) N-benzyl-2-[4-[benzyl(methyl)amino]phenyl]-N-methyl-imidazo[1,2-a]pyridin-7-amine

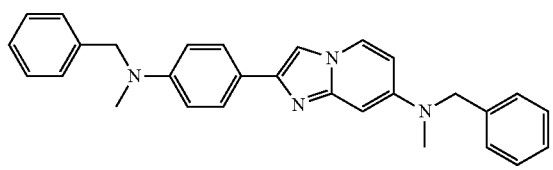 [SMILES: CN(Cc1ccccc1)c1ccc(-c2cn3ccc(N(C)Cc4ccccc4)cc3n2)cc1]

A suspension of 2-(4-bromophenyl)-7-chloroimidazo[1,2-a]pyridine (161 mg, 523 µmol), cesium carbonate (512 mg, 1.57 mmol) and N-methyl-1-phenylmethanamine (159 mg, 167 µl, 1.31 mmol) in dioxane (3 mL) was evacuated and backfilled with argon for 5 times. Then palladium (II) acetate (5.88 mg, 26.2 µmol) and 2-(dicyclohexylphosphino)biphenyl (18.3 mg, 52.3 µmol) was added. The suspension was stirred in a closed tube at 110° C. for 5 h. After cooling to ambient temperature the reaction mixture was concentrated and was purified by flash chromatography (heptane:ethyl acetate=80:20 to 50:50) affording the title compound (73 mg, 32%) which was obtained as a light brown solid. MS m/z: 433.7 [M+H]+.

c) 2-(4-(benzyl(methyl)amino)phenyl)-N-methylimidazo[12-a]pyridin-7-amine

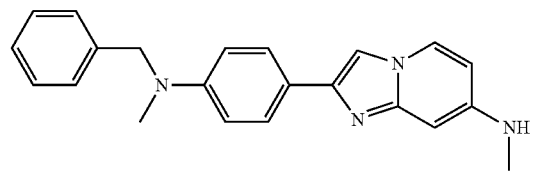 [SMILES: CNc1ccn2cc(-c3ccc(N(C)Cc4ccccc4)cc3)nc2c1]

To a N-benzyl-2-(4-(benzyl(methyl)amino)phenyl)-N-methylimidazo[1,2-a]pyridin-7-amine (156 mg, 361 µmol) was added under an atmosphere of nitrogen hydrobromic acid 48% in water (29.2 mg, 19.6 µl, 361 µmol). Then the solution was stirred at 100° C. for 1 h. After cooling to ambient temperature it was concentrated in vacuum and the residue was diluted with ethyl acetate (15 mL) and was washed with a 1 M solution of sodium carbonate (30 ml), water (15 mL) and brine (10 mL). The aqueous layers were extracted with ethyl acetate (15 mL). The combined organic layers were dried over magnesium sulfate. The filtered and concentrated solution was purified by flash chromatography (heptane:ethyl acetate=60:40 to 20:80) affording the title compound (33 mg, 26%) which was obtained as a light brown solid. MS m/z: 343.2 [M+H]+.

Example 111

N-[2-(3-Bromo-thiophen-2-yl)-imidazo[1,2-a]pyridin-7-yl]-methyl-amine

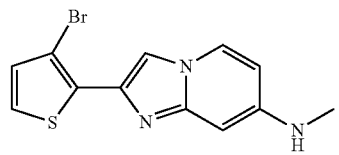 [SMILES: CNc1ccn2cc(-c3sccc3Br)nc2c1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and 2-bromo-1-(3-bromo-2-thienyl)-1-ethanone (518 mg, 1.83 mmol). Brown solid (55 mg, 15%). MS m/z: 307.8 [M*]⁺.

Example 112

N-[2-(3-Chloro-thiophen-2-yl)-imidazo[1,2-a]pyridin-7-yl]-methyl-amine

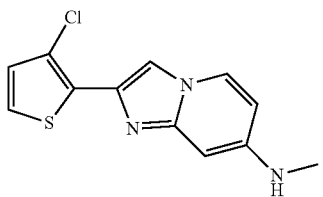 [SMILES: CNc1ccn2cc(-c3sccc3Cl)nc2c1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (157 mg, 1.27 mmol) and 2-bromo-1-(3-chloro-2-thienyl)-1-ethanone (458 mg, 1.91 mmol). Light brown solid (7 mg, 2%). MS m/z: 263.8 [M+H]⁺.

Example 113

N-[2-(4-Difluoromethoxy-phenyl)-imidazo[1,2-a]pyridin-7-yl]-methyl-amine

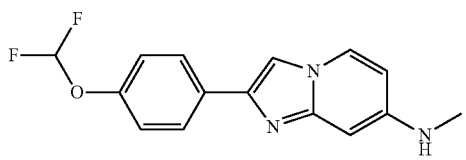 [SMILES: CNc1ccn2cc(-c3ccc(OC(F)F)cc3)nc2c1]

This compound was prepared following the same method as adopted for synthesis of N-[2-(3-fluoro-4-methoxy-phenyl)-imidazo[1,2-a]pyridin-7-yl]-methyl-amine (Example 89) from N4-methyl-pyridine-2,4-diamine (150 mg, 1.22 mmol) and 4-(difluoromethoxy)phenacyl bromide (484 mg, 1.83 mmol). Yellow solid (32 mg, 9%). MS m/z: 289.8 [M+H]⁺.

Example 114

N-[2-(4-Bromo-phenyl)-imidazo[1,2-a]pyridin-7-yl]-methyl-amine

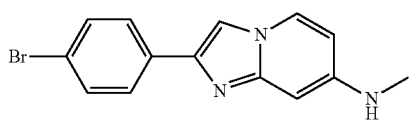

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and 2,4'-dibromoacetophenone (508 mg, 1.83 mmol). Yellow solid (82 mg, 22%). MS m/z: 301.8 [M]⁺.

Example 115

Methyl-[2-(5-methyl-furan-2-yl)-imidazo[1,2-a]pyridin-7-yl]-amine

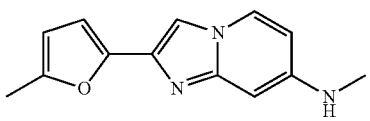

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and 2-bromo-1-(5-methylfuran-2-yl)-ethanone (371 mg, 1.83 mmol). Yellow solid (23 mg, 8%). MS m/z: 228.1 [M+H]⁺.

Example 116

N-[2-(Benzofuran-2-yl)-imidazo[1,2-a]pyridin-7-yl]-methyl-amine

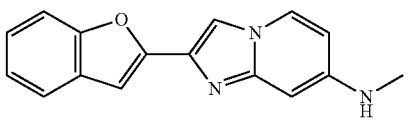 [SMILES: CNc1ccn2cc(-c3cc4ccccc4o3)nc2c1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (153 mg, 1.24 mmol) and 1-(1-benzofuran-2-yl)-2-bromoethan-1-one (445 mg, 1.86 mmol). Yellow solid (14 mg, 4%). MS m/z: 263.8 [M+H]⁺.

Example 117

N-[2-(2,5-Dimethyl-2H-pyrazol-3-yl)-imidazo[1,2-a]pyridin-7-yl]-methyl-amine

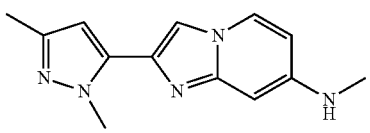

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and 2-bromo-1-(1,3-dimethyl-1H-pyrazol-5-yl)ethanone (397 mg, 1.83 mmol).

Sticky brown solid (75 mg, 25%). MS m/z: 242.2 [M+H]⁺.

Example 118

Methyl-[2-(4-piperidin-1-yl-phenyl)-imidazo[1,2-a]pyridin-7-yl]-amine

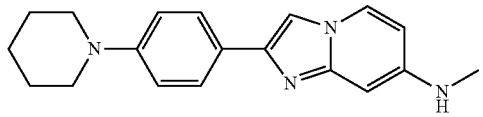 [SMILES: CNc1ccn2cc(-c3ccc(N4CCCCC4)cc3)nc2c1]

This compound was prepared following the same method as adopted for synthesis of N-[2-(3-fluoro-4-methoxy-phenyl)-imidazo[1,2-a]pyridin-7-yl]-methyl-amine (Example 95) from N4-methyl-pyridine-2,4-diamine (150 mg, 1.22 mmol) and 2-bromo-1-(4-(piperidin-1-yl)phenyl)ethanone (515 mg, 1.83 mmol). Yellow solid (100 mg, 27%). MS m/z: 307.0 [M+H]$^+$.

Example 119

6-(7-Methylamino-imidazo[1,2-a]pyridin-2-yl)-4H-benzo[1,4]oxazin-3-one

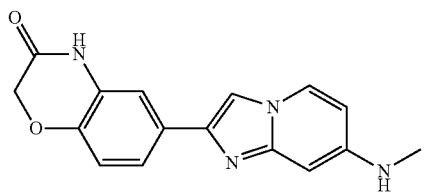 [SMILES: CNc1ccn2cc(-c3ccc4c(c3)NC(=O)CO4)nc2c1]

This compound was prepared following the same method as adopted for synthesis of N-[2-(3-fluoro-4-methoxy-phenyl)-imidazo[1,2-a]pyridin-7-yl]-methyl-amine (Example 89) from N4-methyl-pyridine-2,4-diamine (150 mg, 1.22 mmol) and 6-(2-chloroacetyl)-2H-1,4-benzoxazin-3(4H)-one (412 mg, 1.83 mmol). Off-white solid (7 mg, 2%). MS m/z: 295.0 [M+H]$^+$.

Example 120

2-(7-Methylamino-imidazo[1,2-a]pyridin-2-yl)-phenol

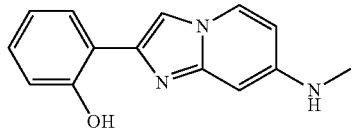 [SMILES: CNc1ccn2cc(-c3ccccc3O)nc2c1]

To a solution at 25° C. under nitrogen of N4-methyl-pyridine-2,4-diamine (200 mg, 1.62 mmol) in acetone (10 ml) was added 2-bromo-1-(2-hydroxyphenyl)ethanone (603 mg, 2.47 mmol) and pTSA (catalytic amount). The mixture was stirred for 30 min at 25° C. and then allowed to reflux for another 16 h. Volatilities were removed under vacuum. The resultant crude material was purified by column chromatography using amine bound silica gel (70% EtOAc/hexane) to afford 2-(7-methylamino-imidazo[1,2-a]pyridin-2-yl)-phenol as yellow solid (55 mg, 14%). MS m/z: 239.6 [M+H]$^+$.

Example 121

Methyl-[2-(1-methyl-1H-benzoimidazol-2-yl)-imidazo[1,2-a]pyridin-7-yl]-amine

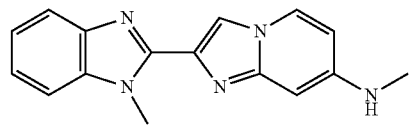 [SMILES: CNc1ccn2cc(-c3nc4ccccc4n3C)nc2c1]

This compound was prepared following the same method as adopted for synthesis of N-[2-(3-fluoro-4-methoxy-phenyl)-imidazo[1,2-a]pyridin-7-yl]-methyl-amine from N4-methyl-pyridine-2,4-diamine (150 mg, 1.22 mmol) and 2-bromo-1-(1-methyl-1H-benzimidazol-2-yl)-1-ethanone (462 mg, 1.83 mmol). Yellow solid (48 mg, 14%). MS m/z: 278.0 [M+H]$^+$.

Example 122

Methyl 3-[7-(methylamino)imidazo[1,2-a]pyridin-2-yl]benzoate

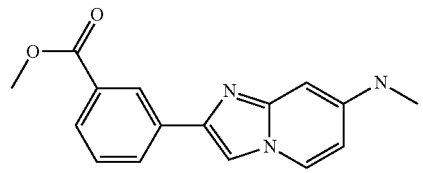

In analogy to the experimental procedure of example 6a) N4-methylpyridine-2,4-diamine instead of 4-bromopyridin-2-amine was converted using methyl 3-(2-bromoacetyl)benzoate instead of 2-bromo-1-(4-methoxyphenyl)ethanone into the title compound (700 mg, 44%) which was obtained as a yellow solid. MS m/z: 282.0 [M+H]$^+$

Example 123

[3-[7-(Methylamino)imidazo[1,2-a]pyridin-2-yl]phenyl]methanol

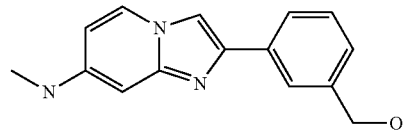 [SMILES: CNc1ccn2cc(-c3cccc(CO)c3)nc2c1]

In analogy to the experimental procedure of example 89b) methyl 3-[7-(methylamino)imidazo[1,2-a]pyridin-2-yl]benzoate instead of methyl 4-[7-(methylamino)imidazo[1,2-a]pyridin-2-yl]benzoate was converted into the title compound (220 mg, 82%) which was obtained as a white solid. MS m/z: 254.2 [M+H]$^+$

Example 124

N-Cyclopropyl-2-[4-(2-fluoroethoxy)phenyl]imidazo[1,2-a]pyridin-7-amine

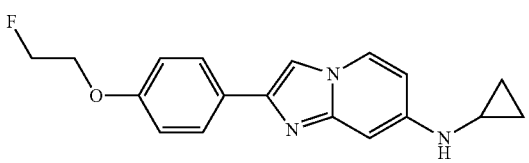 [SMILES: FCCOc1ccc(-c2cn3ccc(NC4CC4)cc3n2)cc1]

a) 4-(7-(Cyclopropylamino)imidazo[1,2-a]pyridin-2-yl)phenol hydrobromide

N4-Cyclopropylpyridine-2,4-diamine (125 mg, 754 µmol; Example 67a) and 2-bromo-1-(4-hydroxyphenyl)ethanone (170 mg, 792 µmol) were combined with acetone (1.4 ml) in a sealed vial under Ar. The reaction mixture was stirred at 65° C. overnight. After cooling to r.t. solids were filtered off and washed with acetone. The resulting white solid was dried under high vacuum to yield 4-(7-(cyclopropylamino)imidazo[1,2-a]pyridin-2-yl)phenol hydrobromide (250 mg, 88%). MS m/z: 266.1 [M+H]$^+$.

b) N-Cyclopropyl-2-[4-(2-fluoroethoxy)phenyl]imidazo[1,2-a]pyridin-7-amine 4-(7-(Cyclopropylamino)imidazo[1,2-a]pyridin-2-yl)phenol hydrobromide (120 mg, 347 µmol) was dissolved in DMF (1.6 ml) to give a colorless solution. Cs$_2$CO$_3$ (339 mg, 1.04 mmol) was added and the mixture was stirred at r.t. for 1 h. 1-Bromo-2-fluoroethane (61.6 mg, 485 µmol) dissolved in 0.5 ml DMF was added and the reaction mixture was stirred at 90° C. overnight. After cooling to r.t. the mixture was diluted with CH$_2$Cl$_2$ and washed with H$_2$O. The aqueous layer was extracted back with CH$_2$Cl$_2$. The organic layers were washed three times with H$_2$O and one time with brine. The organic layers were combined, dried over MgSO$_4$, filtered and concentrated. The residue was triturated with EtOAc to afford N-cyclopropyl-2-(4-(2-fluoroethoxy)phenyl)imidazo[1,2-a]pyridin-7-amine (12 mg, 10%) as an light brown solid. MS m/z: 312.1 [M+H]$^+$.

Example 125

7-(Azetidin-1-yl)-2-[4-(3-fluoropropoxy)phenyl]imidazo[1,2-a]pyridine

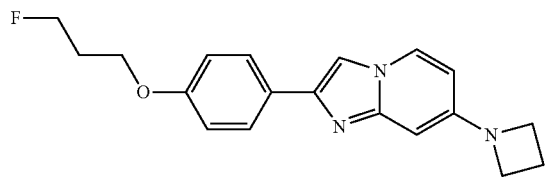 [SMILES: FCCCOc1ccc(-c2cn3ccc(N4CCC4)cc3n2)cc1]

4-(7-(Azetidin-1-yl)imidazo[1,2-a]pyridin-2-yl)phenol (120 mg, 398 µmol; Example 40), 1-bromo-3-fluoropropane (78.6 mg, 557 µmol) and Cs$_2$CO$_3$ (259 mg, 796 µmol) were combined with DMF (2.0 ml) in a sealed tube under Ar. The reaction mixture was stirred overnight at 90° C. After cooling to r.t. CH$_2$Cl$_2$ was added and the mixture was washed with H$_2$O. The aqueous layer (pH-9) was extracted back with CH$_2$Cl$_2$. The organic layers were washed three times with H$_2$O and one time with brine. The organic layers were combined, dried over MgSO$_4$, filtered and concentrated. The residue was dried on high vacuum for 4 h, then triturated with EtOAc to afford 7-(azetidin-1-yl)-2-(4-(3-fluoropropoxy)phenyl)imidazo[1,2-a]pyridine (77 mg, 58%) as an off-white solid. MS m/z: 326.2 [M+H]$^+$.

Example 126

Methyl-(2-pyridin-3-yl-imidazo[1,2-a]pyridin-7-yl)-amine

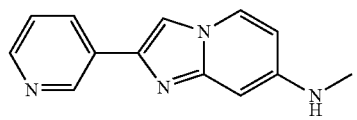 [SMILES: CNc1ccn2cc(-c3cccnc3)nc2c1]

This compound was prepared following the same method as adopted for synthesis of N-[2-(3-fluoro-4-methoxy-phenyl)-imidazo[1,2-a]pyridin-7-yl]-methyl-amine (Example 89) from N4-methyl-pyridine-2,4-diamine (152 mg, 1.23 mmol) and 3-(2-bromoacetyl)pyridinium bromide (520 mg, 1.85 mmol). Brown sticky solid (7 mg, 2%). MS m/z: 225.0 [M+H]$^+$.

Example 127

N-[2-(5-Chloro-thiophen-2-yl)-imidazo[1,2-a]pyridin-7-yl]-methyl-amine

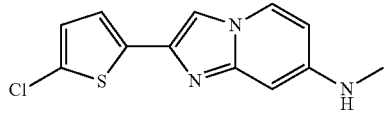 [SMILES: CNc1ccn2cc(-c3ccc(Cl)s3)nc2c1]

This compound was prepared following the same method as adopted for synthesis of N-[2-(3-fluoro-4-methoxy-phenyl)-imidazo[1,2-a]pyridin-7-yl]-methyl-amine (Example 89) from N4-methyl-pyridine-2,4-diamine (150 mg, 1.22 mmol) and 2-bromo-1-(5-chloro-2-thienyl)-1-ethanone (437 mg, 1.83 mmol). Yellow solid (12 mg, 4%). MS m/z: 263.8 [M+H]$^+$.

Example 128

4-Methyl-2-(7-methylamino-imidazo[1,2-a]pyridin-2-yl)-phenol

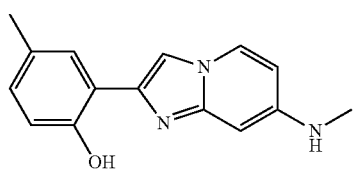 [SMILES: CNc1ccn2cc(-c3cc(C)ccc3O)nc2c1]

a) 2-Bromo-1-(2-hydroxy-5-methyl-phenyl)-ethanone

To a solution of 1-(2-hydroxy-5-methyl-phenyl)-ethanone (500 mg, 3.33 mmol) in CHCl$_3$ (12 ml) and EtOAc (12 ml)

was added CuBr₂ (1.5 g, 6.67 mmol) at 25° C. under nitrogen. The mixture was stirred at 100° C. for 16 h. After cooling, solids were filtered off and the filtrate was concentrated under reduced pressure to get 2-bromo-1-(2-hydroxy-5-methyl-phenyl)-ethanone as brown oil (as crude, 625 mg) that was used in the next step as such without any further purification.

b) 4-Methyl-2-(7-methylamino-imidazo[1,2-a]pyridin-2-yl)-phenol

This compound was prepared following the same method as adopted for synthesis of 2-(7-methylamino-imidazo[1,2-a]pyridin-2-yl)-phenol (Example 117) from N4-methyl-pyridine-2,4-diamine (250 mg, 2.03 mmol) and 2-bromo-1-(2-hydroxy-5-methyl-phenyl)ethanone (697 mg, 3.04 mmol). Off-white solid (35 mg, 7%). MS m/z: 253.8 [M+H]⁺.

Example 129

Methyl-[2-(1-methyl-1H-pyrazol-4-yl)-imidazo[1,2-a]pyridin-7-yl]-amine

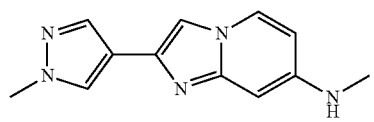

To a solution of 2-bromo-1-(1-methyl-1H-pyrazol-4-yl)-ethanone hydrobromide (346 mg, 1.22 mmol) in EtOH (10 ml) at 25° C. was added NaHCO₃ (82 mg, 0.97 mmol) and the mixture was stirred for 5 min at 25° C. To this mixture was then added N4-methyl-pyridine-2,4-diamine (100 mg, 0.81 mmol) and it was stirred for another 16 h under reflux. Volatiles were removed under reduced pressure. The resultant crude material was purified by flash chromatography using amine bound silica gel (EtOAc/hexane 4:1) followed by prep. HPLC to afford methyl-[2-(1-methyl-1H-pyrazol-4-yl)-imidazo[1,2-a]pyridin-7-yl]-amine as sticky brown solid (29 mg, 16%). MS m/z: 228.2 [M+H]⁺.

Example 130

2-[3-(Methoxymethyl)phenyl]-N-methyl-imidazo[1,2-a]pyridine-7-amine HCl adduct

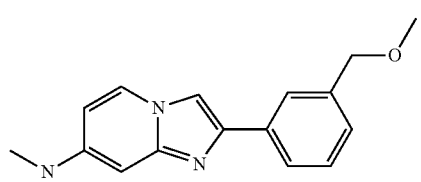

a) 4-(7-Methylamino-imidazo[1,2-a]pyrimidin-2-yl)-benzoic acid methyl ester

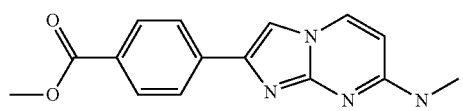

In analogy to the experimental procedure of example 6a) N4-methylpyridine-2,4-diamine instead of 4-bromopyridin-2-amine was converted using 4-(2-bromo-acetyl)-benzoic acid methyl ester instead of 2-bromo-1-(4-methoxyphenyl) ethanone into the title compound (100 mg, 18%) which was obtained as an off-white solid. MS m/z: 283.0 [M+H]⁺ b) 4-[7-(tert-Butoxycarbonyl-methyl-amino)-imidazo[1,2-a]pyrimidin-2-yl]-benzoic acid methyl ester

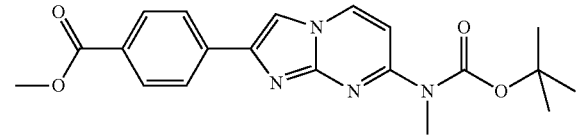 [SMILES: COC(=O)c1ccc(-c2cn3ccc(N(C)C(=O)OC(C)(C)C)nc3n2)cc1]

To a solution of 4-(7-methylamino-imidazo[1,2-a]pyrimidin-2-yl)-benzoic acid methyl ester (600 mg, 2.12 mmol) in THF (30 mL) were added di-tert-butyl dicarbonate (0.95 mL, 4.251 mmol) and DMAP (11.92 mg, 0.106 mmol), and stirred the reaction mixture at 25° C. for 6 h. After evaporation of excess solvent under reduced pressure; the crude thus obtained was purified by chromatography over normal silica gel (30% EtOAc/hexane) to give the title compound (670 mg, 82%) as an off white solid. MS m/z: 383.0 [M+H]⁺ c) [2-(4-Hydroxymethyl-phenyl)-imidazo[1,2-a]pyrimidin-7-yl]-methyl-carbamic acid tert-butyl ester

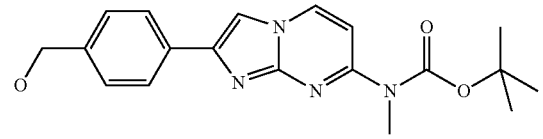 [SMILES: CN(C(=O)OC(C)(C)C)c1ccn2cc(-c3ccc(CO)cc3)nc2n1]

In analogy to the experimental procedure of example 89b) 4-[7-(tert-butoxycarbonyl-methyl-amino)-imidazo[1,2-a]pyrimidin-2-yl]-benzoic acid methyl ester instead of methyl 4-[7-(methylamino)imidazo[1,2-a]pyridin-2-yl]benzoate was converted into the title compound (152 mg, 82%) which was obtained as a white solid. MS m/z: 355.0 [M+H]⁺ d) [2-(4-Methoxymethyl-phenyl)-imidazo[1,2-a]pyrimidin-7-yl]-methylcarbamic acid tert-butyl ester

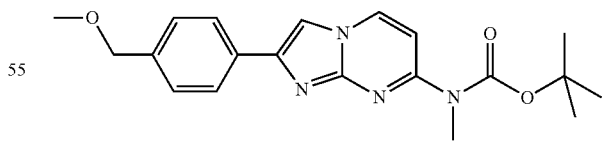

To a solution of [2-(4-hydroxymethyl-phenyl)-imidazo[1,2-a]pyrimidin-7-yl]-methyl-carbamic acid tert-butyl ester (100 mg, 0.282 mmol) in DMF (5 mL) was added K2CO3 (78 mg, 0.564 mmol), and the reaction mixture was stirred at 25° C. for 20 min. To this mixture was then added methyl iodide (0.1 mL, 1.6 mmol) at 0° C., and the mixture was stirred at 25° C. for 16 h. It was filtered, and filtrate was concentrated under reduced pressure. Crude material thus obtained was purified by silica gel column chromatography over normal silica gel (10% EtOAc/DCM) to give the title compound (100 mg, 96%) as an off white solid. MS m/z: 368.8 [M+H]+ e) [2-(4-Methoxymethyl-phenyl)-imidazo[1,2-a]pyrimidin-7-yl]-methylamine

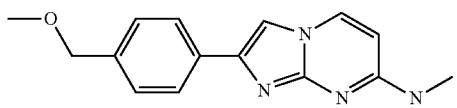

To a solution of [2-(4-Methoxymethyl-phenyl)-imidazo[1,2-a]pyrimidin-7-yl]-methylcarbamic acid tert-butyl ester (100 mg, 0.271 mmol) in MeOH (3 mL) at 0° C. was added 4N HCl/MeOH (0.5 mL, 1.87 mmol) slowly, and the reaction mixture was stirred at 25° C. for 16 h. Volatiles were removed under reduced pressure; and crude material thus obtained was purified by triturating with ethyl acetate to give the title compound (50 mg, 69%) as a yellow solid MS m/z: 269.2 [M+H]+

Example 131

2-(4-(2-fluoroethylamino)phenyl)-N-methylimidazo[1,2-a]pyridin-7-amine

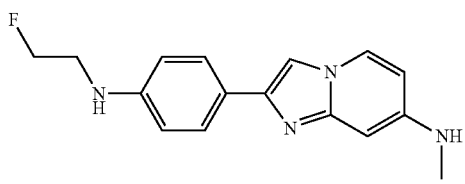 [SMILES: CNc1ccn2cc(-c3ccc(NCCF)cc3)nc2c1]

a) 2-(4-bromophenyl)-N-methyl-imidazo[1,2-a]pyridin-7-amine

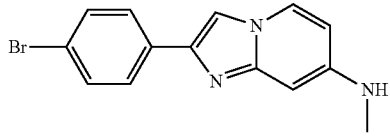 [SMILES: CNc1ccn2cc(-c3ccc(Br)cc3)nc2c1]

In analogy to the experimental procedure of example 6a) N4-methylpyridine-2,4-diamine instead of 4-bromopyridin-2-amine was converted using 2-bromo-1-(4-bromophenyl)ethanone instead of 2-bromo-1-(4-methoxyphenyl)ethanone into the title compound (865 mg, 67%) which was obtained as an off-white oil. MS m/z: 302.5/304.5 [M+H]+ b) 2-(4-(2-fluoroethylamino)phenyl)-N-methylimidazo[1,2-a]pyridin-7-amine

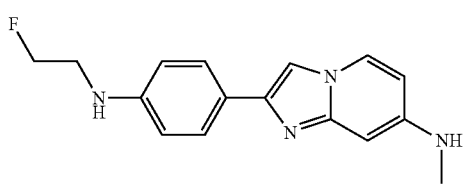 [SMILES: CNc1ccn2cc(-c3ccc(NCCF)cc3)nc2c1]

In analogy to the experimental procedure of example 110b) 2-(4-bromophenyl)-N-methylimidazo[1,2-a]pyridin-7-amine instead of 2-(4-bromophenyl)-7-chloroimidazo[1,2-a]pyridine was converted using 2-fluoroethanamine hydrochloride instead of N-methyl-1-phenylmethanamine into the title compound (5 mg, 4%) which was obtained as a light brown solid. MS m/z: 285.5 [M+H]+

Example 132

N-(3-fluoropropyl)-2-(4-methoxyphenyl)imidazo[1,2-a]pyridin-7-amine

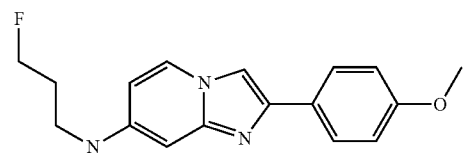 [SMILES: COc1ccc(-c2cn3ccc(NCCCF)cc3n2)cc1]

In analogy to the experimental procedure of example 110b) 7-bromo-2-(4-methoxyphenyl)imidazo[1,2-a]pyridine instead of 2-(4-bromophenyl)-7-chloroimidazo[1,2-a]pyridine was converted using 3-fluoropropan-1-amine hydrochloride instead of N-methyl-1-phenylmethanamine into the title compound (8 mg, 8%) which was obtained as a light brown solid. MS m/z: 300.5 [M+H]+

Example 133

2-(3-(fluoromethoxy)phenyl)-N-methylimidazo[1,2-a]pyridin-7-amine

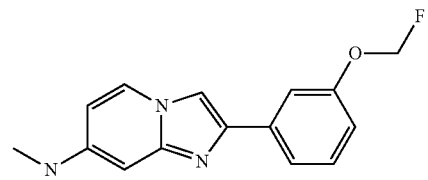 [SMILES: CNc1ccn2cc(-c3cccc(OCF)c3)nc2c1]

In analogy to the experimental procedure of example 107 3-(7-(methylamino)imidazo[1,2-a]pyridin-2-yl)phenol hydrobromide instead of 3-(7-(azetidin-1-yl)imidazo[1,2-a]pyridin-2-yl)phenol was converted into the title compound (27 mg, 19%) which was obtained as an off-white solid. MS m/z: 272.5 [M+H]+

Example 134

2-(2-(4-methoxyphenyl)imidazo[1,2-a]pyridin-7-ylamino)propan-1-ol

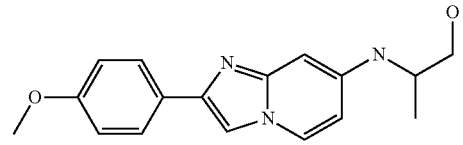 [SMILES: COc1ccc(-c2cn3ccc(NC(C)CO)cc3n2)cc1]

To a suspension of 7-bromo-2-(4-methoxyphenyl)imidazo[1,2-a]pyridine (129 mg, 426 μmol) in toluene (2 mL) was added under an atmosphere of nitrogen 2-aminopropan-1-ol (47.9 mg, 50.8 μL, 638 μmol) and sodium tert-butoxide (123 mg, 1.28 mmol). After the flask was evacuated and backfilled with argon for five times 2-di-tert-butylphosphino-2',4',6'-triisopropylbiphenyl (18.1 mg, 42.6 µmol) and tris(dibenzylideneacetone)dipalladium(0) chloroform adduct (13.2 mg, 12.8 µmol) was added. The reaction mixture was stirred at 110° C. for 18 h. It was concentrated purification by flash chromatography (dichloromethane:(dichloromethane:methanol:ammonia=90:9:1)=80:20 to 30:70) afforded the title compound (47 mg, 37%) which was obtained as a light brown foam. MS m/z: 298.5 [M+H]+

Example 135

N-(2-fluoroethyl)-2-(3-methoxy-4-methylphenyl)imidazo[1,2-a]pyridin-7-amine

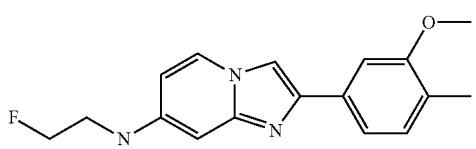 [SMILES: COc1cc(-c2cn3ccc(NCCF)cc3n2)ccc1C]

In analogy to the experimental procedure of example 6a) N4-(2-fluoroethyl)pyridine-2,4-diamine instead of 4-bromopyridin-2-amine was converted using 2-bromo-1-(3-methoxy-4-methylphenyl)ethanone instead of 2-bromo-1-(4-methoxyphenyl)ethanone into the title compound (5 mg, 4%) which was obtained as a brown oil. MS m/z: 300.5 [M+H]+

Example 136

N-methyl-2-(3-(methylthio)phenyl)imidazo[1,2-a]pyridin-7-amine

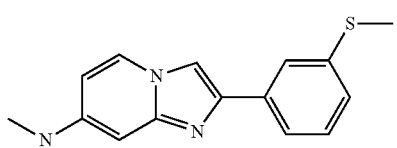

In analogy to the experimental procedure of example 6a) N4-methylpyridine-2,4-diamine instead of 4-bromopyridin-2-amine was converted using 2-bromo-1-(3-(methylthio)phenyl)ethanone instead of 2-bromo-1-(4-methoxyphenyl)ethanone into the title compound (7 mg, 7%) which was obtained as a brown oil. MS m/z: 270.5 [M+H]+

Example 137

2-(3-(2-fluoroethoxy)phenyl)-N-methylimidazo[1,2-a]pyridin-7-amine

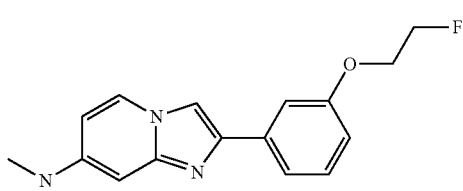 [SMILES: CNc1ccn2cc(-c3cccc(OCCF)c3)nc2c1]

In analogy to the experimental procedure of example 106 3-(7-(methylamino)imidazo[1,2-a]pyridin-2-yl)phenol hydrobromide instead 4-(7-(azetidin-1-yl)imidazo[1,2-a]pyridin-2-yl)phenol of was converted into the title compound (89 mg, 50%) which was obtained as a light yellow foam. MS m/z: 286.5 [M+H]+

Example 138

2-(4-methoxyphenyl)-7-(2-methylaziridin-1-yl)imidazo[1,2-a]pyridine

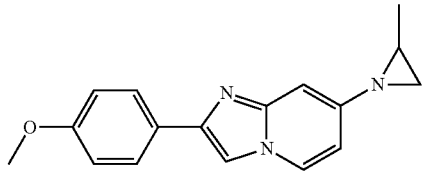 [SMILES: COc1ccc(-c2cn3ccc(N4CC4C)cc3n2)cc1]

To a solution of 2-(2-(4-methoxyphenyl)imidazo[1,2-a]pyridin-7-ylamino)propan-1-ol (42 mg, 141 µmol) in dichloromethane (2 mL) was added under an atmosphere of nitrogen at −70° C. bis(2-methoxyethyl)aminosulfur trifluoride (62.5 mg, 52.1 µL, 282 µmol). After stirring at −70° C. for 30 min the cooling bath was removed and the reaction mixture was stirred at ambient temperature for 1 h. It was added onto a aqueous sodium carbonate solution (1M, 15 mL) and was extracted twice with dichloromethane (15 mL). The combined organic layers were dried over magnesium sulfate. The filtered and concentrated solution was purified by flash chromatography (dichloromethane:(dichloromethane:methanol:ammonia=90:9:1)=90:10 to 30:70) affording the title compound (19 mg, 49%) which was obtained as an off-white solid. MS m/z: 280.5 [M+H]+

Example 139

2-(3-(3-fluoropropoxy)phenyl)-N-methylimidazo[1,2-a]pyridin-7-amine

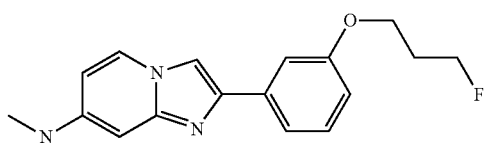 [SMILES: CNc1ccn2cc(-c3cccc(OCCCF)c3)nc2c1]

In analogy to the experimental procedure of example 106 3-(7-(methylamino)imidazo[1,2-a]pyridin-2-yl)phenol hydrobromide instead 4-(7-(azetidin-1-yl)imidazo[1,2-a]pyridin-2-yl)phenol of was converted using 1-fluoro-3-iodopropane instead of 1-bromo-2-fluoroethane into the title compound (72 mg, 41%) which was obtained as a brown foam. MS m/z: 300.5 [M+H]+

Example 140

7-(azetidin-1-yl)-2-(3-(2-fluoroethoxy)phenyl)imidazo[1,2-a]pyridine

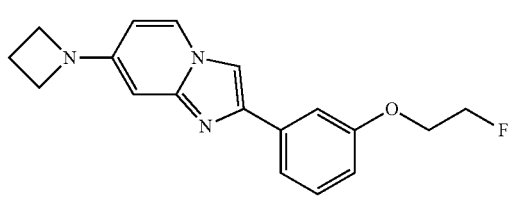 [SMILES: FCCOc1cccc(-c2cn3ccc(N4CCC4)cc3n2)c1]

In analogy to the experimental procedure of example 106 3-(7-(azetidin-1-yl)imidazo[1,2-a]pyridin-2-yl)phenol hydrobromide instead 4-(7-(azetidin-1-yl)imidazo[1,2-a]pyridin-2-yl)phenol of was converted into the title compound (57 mg, 33%) which was obtained as a white solid. MS m/z: 312.5 [M+H]$^+$ Example 141

2-(4-(4-fluoropiperidin-1-yl)phenyl)-N-methylimidazo[1,2-a]pyridin-7-amine

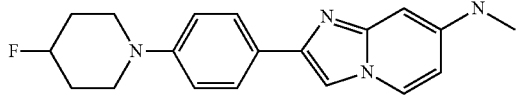 [SMILES: CNc1ccn2cc(-c3ccc(N4CCC(F)CC4)cc3)nc2c1]

In analogy to the experimental procedure of example 110b) 2-(4-bromophenyl)-N-methylimidazo[1,2-a]pyridin-7-amine hydrochloride instead of 2-(4-bromophenyl)-7-chloroimidazo[1,2-a]pyridine was converted using 4-fluoropiperidine hydrochloride instead of N-methyl-1-phenylmethanamine into the title compound (5 mg, 4%) which was obtained as an off-white solid. MS m/z: 325.6 [M+H]$^+$ Example 142

4-(7-(2-fluoroethylamino)imidazo[1,2-a]pyridin-2-yl)-2-methoxyphenol

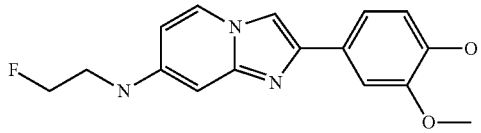 [SMILES: COc1cc(-c2cn3ccc(NCCF)cc3n2)ccc1O]

In analogy to the experimental procedure of example 6a) N4-(2-fluoroethyl)pyridine-2,4-diamine instead of 4-bromopyridin-2-amine was converted using 2-bromo-1-(4-hydroxy-3-methoxyphenyl)ethanone instead of 2-bromo-1-(4-methoxyphenyl)ethanone into the title compound (58 mg, 37%) which was obtained as a light red solid. MS m/z: 302.1 [M+H]$^+$ Example 143

2-(2,3-dihydrobenzo[b][1,4]dioxin-6-yl)-N-(2-fluoroethyl)imidazo[1,2-a]pyridin-7-amine

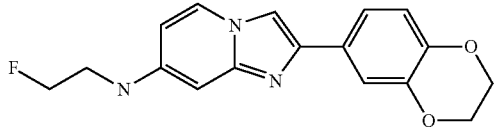 [SMILES: FCCNc1ccn2cc(-c3ccc4c(c3)OCCO4)nc2c1]

In analogy to the experimental procedure of example 6a) N4-(2-fluoroethyl)pyridine-2,4-diamine instead of 4-bromopyridin-2-amine was converted using 2-bromo-1-(2,3-dihydrobenzo[b][1,4]dioxin-6-yl)ethanone instead of 2-bromo-1-(4-methoxyphenyl)ethanone into the title compound (45 mg, 28%) which was obtained as a light yellow oil. MS m/z: 314.1 [M+H]$^+$ Example 144

7-(azetidin-1-yl)-2-(4-(2-(2-fluoroethoxy)ethoxy)phenyl)imidazo[1,2-a]pyridine

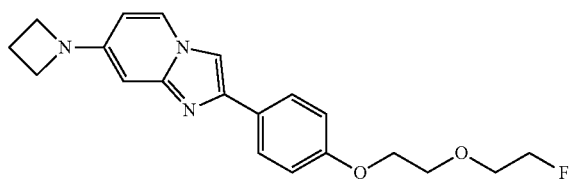 [SMILES: FCCOCCOc1ccc(-c2cn3ccc(N4CCC4)cc3n2)cc1]

In analogy to the experimental procedure of example 125 4-(7-(azetidin-1-yl)imidazo[1,2-a]pyridin-2-yl)phenol was converted using 2-(2-fluoroethoxy)ethyl 4-methylbenzenesulfonate instead of 1-bromo-3-fluoropropane into the title compound (189 mg, 76%) which was obtained as an off-white solid. MS m/z: 356.2 [M+H]$^+$ Example 145

4-(7-(2-fluoroethylamino)imidazo[1,2-a]pyridin-2-yl)phenol

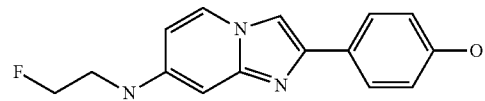 [SMILES: Oc1ccc(-c2cn3ccc(NCCF)cc3n2)cc1]

In analogy to the experimental procedure of example 6a) N4-(2-fluoroethyl)pyridine-2,4-diamine instead of 4-bromopyridin-2-amine was converted using 2-bromo-1-(4-hydroxyphenyl)ethanone instead of 2-bromo-1-(4-methoxyphenyl)ethanone into the title compound (6 mg, 11%) which was obtained as a white solid. MS m/z: 272.5 [M+H]$^+$ Example 146

3-(7-(2-fluoroethylamino)imidazo[1,2-a]pyridin-2-yl)phenol

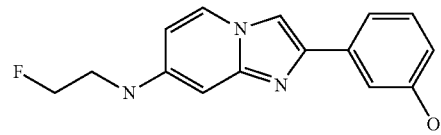 [SMILES: Oc1cccc(-c2cn3ccc(NCCF)cc3n2)c1]

In analogy to the experimental procedure of example 6a) N4-(2-fluoroethyl)pyridine-2,4-diamine instead of 4-bromopyridin-2-amine was converted using 2-bromo-1-(3-hydroxyphenyl)ethanone instead of 2-bromo-1-(4-methoxyphenyl)ethanone into the title compound (26 mg, 11%) which was obtained as an off-white foam. MS m/z: 272.5 [M+H]$^+$

Example 147

N-(2-Fluoroethyl)-2-(4-morpholin-4-ylphenyl)imidazo[1,2-a]pyridin-7-amine

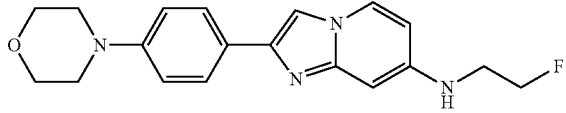

4-(4-(7-Bromoimidazo[1,2-a]pyridin-2-yl)phenyl)morpholine (150 mg, 419 µmol), 2-fluoroethanamine hydrochloride (50.0 mg, 502 µmol) and Cs$_2$CO$_3$ (682 mg, 2.09 mmol) were combined with dioxane (6.0 ml). The reaction mixture was put under Ar, then [Pd$_2$(dba)$_3$].CHCl$_3$ (19.2 mg, 20.9 µmol) and Xantphos (24.2 mg, 41.9 µmol) were added. The mixture was flushed one more time with Ar and stirred in the closed tube at 110° C. for 5 h. After cooling to r.t. the reaction mixture was concentrated in vacuum. The product was purified by flash chromatography (20 g SiO$_2$ cartridge, CH$_2$Cl$_2$ to CH$_2$Cl$_2$/MeOH/aq. NH$_3$ 140:10:1) followed by prep. HPLC to yield 10 mg (7%) of N-(2-fluoroethyl)-2-(4-morpholin-4-ylphenyl)imidazo[1,2-a]pyridin-7-amine as light yellow solid. MS m/z: 341.2 [M+H]$^+$.

Example 148

N-Cyclopropyl-2-[4-(3-fluoropropoxy)phenyl]imidazo[1,2-a]pyridin-7-amine

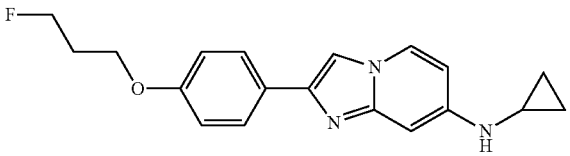 [SMILES: FCCCOc1ccc(-c2cn3ccc(NC4CC4)cc3n2)cc1]

4-(7-(Cyclopropylamino)imidazo[1,2-a]pyridin-2-yl)phenol hydrobromide (125 mg, 332 µmol, Example 121a) was combined with DMF (2.0 ml) to give a colorless solution. Cs$_2$CO$_3$ (325 mg, 996 µmol) was added and the reaction mixture was stirred at r.t. for 1 h. 1-Bromo-3-fluoropropane (65.6 mg, 465 µmol) dissolved in DMF (0.5 ml) was added. The vial was flushed with Ar and the reaction mixture was stirred at 90° C. overnight. The reaction mixture was cooled to r.t., diluted with CH$_2$Cl$_2$ and washed with H$_2$O. The aqueous layer (pH ~9) was extracted back with CH$_2$Cl$_2$. The organic layers were washed three times with H$_2$O and one time with brine. The organic layers were combined, dried over MgSO$_4$, filtered and concentrated. The residue was purified by prep. HPLC to yield the title compound (34 mg, 22%) as light green solid. MS m/z: 326.2 [M+H]$^+$.

Example 149

N-(2-Fluoroethyl)-2-(furan-2-yl)imidazo[1,2-a]pyridin-7-amine

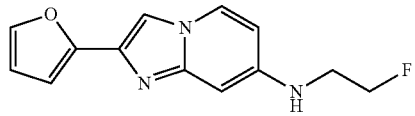 [SMILES: FCCNc1ccn2cc(-c3ccco3)nc2c1]

a) 7-Bromo-2-(furan-2-yl)imidazo[1,2-a]pyridine

4-Bromopyridin-2-amine (300 mg, 1.73 mmol) and 2-bromo-1-(furan-2-yl)ethanone (328 mg, 1.73 mmol) were combined with acetone (3.0 ml) under Ar. The reaction mixture was stirred at 70° C. overnight. Solids were collected by filtration and washed with acetone. H$_2$O (4.4 ml) and 25% aq. NH$_4$OH (3.9 ml) were added. The light yellow suspension was stirred at r.t. for 15 min before filtering it and washing with H$_2$O. The resulting solid was purified by flash chromatography (20 g SiO$_2$ cartridge, CH$_2$Cl$_2$ to CH$_2$Cl$_2$/MeOH/aq. NH$_3$ 140:10:1) to yield the title compound as white solid (276 mg, 61%). MS m/z: 263.0 [M+H]$^+$.

b) N-(2-Fluoroethyl)-2-(furan-2-yl)imidazo[1,2-a]pyridin-7-amine

7-Bromo-2-(furan-2-yl)imidazo[1,2-a]pyridine (276 mg, 1.05 mmol), 2-fluoroethanamine hydrochloride (126 mg, 1.26 mmol) and Cs$_2$CO$_3$ (1.71 g, 5.25 mmol) were combined with dioxane (15 ml). The reaction mixture was placed under Ar, then [Pd$_2$(dba)$_3$].CHCl$_3$ (48.1 mg, 52.5 µmol) and Xantphos (60.8 mg, 105 µmol) were added. The mixture was stirred in the closed tube at 110° C. for 5 h, then at r.t. overnight. The mixture was concentrated under vacuum. The crude product was purified by flash chromatography (50 g SiO$_2$ cartridge, CH$_2$Cl$_2$ to CH$_2$Cl$_2$/MeOH/aq. NH$_3$ 140:10:1) and finally by prep. HPLC. N-(2-Fluoroethyl)-2-(furan-2-yl)imidazo[1,2-a]pyridin-7-amine was obtained as a light yellow solid (23 mg, 9%). MS m/z: 246.1 [M+H]$^+$.

We claim:
1. A compound selected from the group consisting of:
N-(2-fluoroethyl)-2-phenylimidazo[1,2-a]pyridin-7-amine,
N-(2-fluoroethyl)-N-methyl-2-phenylimidazo[1,2-a]pyridin-7-amine,
N,N-dimethyl-2-phenylimidazo[1,2-a]pyridin-7-amine,
N-methyl-2-phenylimidazo[1,2-a]pyridin-7-amine,
[2-(4-dimethylamino-phenyl)-imidazo[1,2-a]pyridin-7-yl]-dimethyl-amine,
(2-[4-(2-fluoro-ethoxy)-phenyl]-imidazo[1,2-a]pyridin-7-yl}-dimethyl-amine,
[2-(4-fluoromethoxy-phenyl)-imidazo[1,2-a]pyridin-7-yl]-dimethyl-amine,
[2-(4-methoxy-phenyl)-imidazo[1,2-a]pyridin-7-yl]-dimethyl-amine,
N-methyl-2-m-tolylimidazo[1,2-a]pyridin-7-amine,
N,N-dimethyl-(2-m-tolyl-imidazo[1,2-a]pyridin-7-yl)-amine,
N,N-dimethyl-(2-p-tolyl-imidazo[1,2-a]pyridin-7-yl)-amine,
N-methyl-(2-p-tolyl-imidazo[1,2-a]pyridin-7-yl)-amine,
N-(2-fluoroethyl)-N-methyl-(2-p-tolyl-imidazo[1,2-a]pyridin-7-yl)-amine,
2-(4-(dimethylamino)phenyl)-N-(2-fluoroethyl)-N-methylimidazo[1,2-a]pyridin-7-amine,
[2-(3-methoxy-phenyl)-imidazo[1,2-a]pyridin-7-yl]-dimethyl-amine,
(2-fluoro-ethyl)-methyl-(2-m-tolyl-imidazo[1,2-a]pyridin-7-yl)-amine
[2-(3-methoxy-phenyl)-imidazo[1,2-a]pyridin-7-yl]-methyl-amine,
[2-(4-fluoromethoxy-phenyl)-imidazo[1,2-a]pyridin-7-yl]-methyl-amine,
(2-fluoro-ethyl)-(2-p-tolyl-imidazo[1,2-a]pyridin-7-yl)-amine,

(2-fluoro-ethyl)-(2-m-tolyl-imidazo[1,2-a]pyridin-7-yl)-amine,
(2-fluoro-ethyl)-[2-(4-fluoromethoxy-phenyl)-imidazo[1,2-a]pyridin-7-yl]-amine,
[2-(3,4-dimethyl-phenyl)-imidazo[1,2-a]pyridin-7-yl]-dimethyl-amine,
[2-(3,4-dimethyl-phenyl)-imidazo[1,2-a]pyridin-7-yl]-methyl-amine,
[$^3$H]-[2-(4-fluoromethoxy-phenyl)-imidazo[1,2-a]pyridin-7-yl]-methyl-amine,
[$^3$H]—N-methyl-2-phenyl-imidazo[1,2-a]pyridin-7-amine,
[$^3$H]—N-(2-fluoroethyl)-2-phenyl-imidazo[1,2-a]pyridin-7-amine,
[$^3$H]—N-methyl-(2-p-tolyl-imidazo[1,2-a]pyridin-7-yl)-amine,
(2-fluoro-ethyl)-[2-(4-methoxy-phenyl)-imidazo[1,2-a]pyridin-7-yl]-methyl-amine,
[2-(3,4-dimethoxy-phenyl)-imidazo[1,2-a]pyridin-7-yl]-methyl-amine,
cyclopropyl-[2-(4-methoxy-phenyl)-imidazo[1,2-a]pyridin-7-yl]-amine,
methyl-[2-(4-methyl sulfanyl-phenyl)-imidazo[1,2-a]pyridin-7-yl]-amine,
[2-(3,4-dimethyl-phenyl)-imidazo[1,2-a]pyridin-7-yl]-(2-fluoro-ethyl)-amine,
[2-(3,4-dimethoxy-phenyl)-imidazo[1,2-a]pyridin-7-yl]-(2-fluoro-ethyl)-amine,
[2-(4-methoxy-phenyl)-imidazo[1,2-a]pyridin-7-yl]-methyl-amine,
(2-fluoro-ethyl)-[2-(4-methoxy-phenyl)-imidazo[1,2-a]pyridin-7-yl]-amine,
(2-fluoro-ethyl)-[2-(3-methoxy-phenyl)-imidazo[1,2-a]pyridin-7-yl]-amine,
[2-(3-fluoromethoxy-phenyl)-imidazo[1,2-a]pyridin-7-yl]-dimethyl-amine,
(2-fluoro-ethyl)-[2-(4-methyl sulfanyl-phenyl)-imidazo[1,2-a]pyridin-7-yl]-amine,
cyclopropyl-[2-(4-fluoromethoxy-phenyl)-imidazo[1,2-a]pyridin-7-yl]-amine,
2-methoxy-4-(7-methylamino-imidazo[1,2-a]pyridin-2-yl)-phenol,
3-(7-dimethylamino-imidazo[1,2-a]pyridin-2-yl)-phenol,
[4-[7-(methylamino)imidazo[1,2-a]pyridin-2-yl]phenyl]methanol,
[4-[7-(dimethylamino)imidazo[1,2-a]pyridin-2-yl]phenyl]methanol,
2-(3,5-dimethoxyphenyl)-N-methylimidazo[1,2-a]pyridin-7-amine,
N-[2-(4-ethoxy-phenyl)-imidazo[1,2-a]pyridin-7-yl]-methyl-amine,
methyl-[2-(4-pyrrolidin-1-yl-phenyl)-imidazo[1,2-a]pyridin-7-yl]-amine,
N-[2-(3-fluoro-4-methoxy-phenyl)-imidazo[1,2-a]pyridin-7-yl]-methyl-amine,
N-[2-(4-diethylamino-phenyl)-imidazo[1,2-a]pyridin-7-yl]-methyl-amine,
N-[2-(4-ethyl-phenyl)-imidazo[1,2-a]pyridin-7-yl]-methyl-amine,
2-[4-(methoxymethyl)phenyl]-N,N-dimethyl-imidazo[1,2-a]pyridin-7-amine,
methyl-[2-(4-morpholin-4-yl-phenyl)-imidazo[1,2-a]pyridin-7-yl]-amine,
2-[4-(2-fluoroethoxymethyl)phenyl]-N,N-dimethyl-imidazo[1,2-a]pyridin-7-amine,
2-(3-methoxy-4-methylphenyl)-N-methylimidazo[1,2-a]pyridin-7-amine,
2-[4-(2-fluoroethoxy)phenyl]-N-methylimidazo[1,2-a]pyridin-7-amine,
2-(4-(benzyl(methyl)amino)phenyl)-N-methylimidazo[1,2-a]pyridin-7-amine,
N-[2-(4-difluoromethoxy-phenyl)-imidazo[1,2-a]pyridin-7-yl]-methyl-amine,
N-[2-(4-bromo-phenyl)-imidazo[1,2-a]pyridin-7-yl]-methyl-amine,
methyl-[2-(4-piperidin-1-yl-phenyl)-imidazo[1,2-a]pyridin-7-yl]-amine,
2-(7-methylamino-imidazo[1,2-a]pyridin-2-yl)-phenol,
methyl 3-[7-(methylamino)imidazo[1,2-a]pyridin-2-yl] benzoate,
[3-[7-(methylamino)imidazo[1,2-a]pyridin-2-yl]phenyl] methanol,
N-cyclopropyl-2-[4-(2-fluoroethoxy)phenyl]imidazo[1,2-a]pyridin-7-amine,
7-(azetidin-1-yl)-2-[4-(3-fluoropropoxy)phenyl]imidazo[1,2-a]pyridine,
4-methyl-2-(7-methylamino-imidazo[1,2-a]pyridin-2-yl)-phenol,
2-[3-(methoxymethyl)phenyl]-N-methyl-imidazo[1,2-a]pyridine-7-amine,
2-(4-(2-fluoroethylamino)phenyl)-N-methylimidazo[1,2-a]pyridin-7-amine,
N-(3-fluoropropyl)-2-(4-methoxyphenyl)imidazo[1,2-a]pyridin-7-amine,
2-(3-(fluoromethoxy)phenyl)-N-methylimidazo[1,2-a]pyridin-7-amine,
2-(2-(4-methoxyphenyl)imidazo[1,2-a]pyridin-7-ylamino)propan-1-ol,
N-(2-fluoroethyl)-2-(3-methoxy-4-methylphenyl)imidazo[1,2-a]pyridin-7-amine,
N-methyl-2-(3-(methylthio)phenyl)imidazo[1,2-a]pyridin-7-amine,
2-(3-(2-fluoroethoxy)phenyl)-N-methylimidazo[1,2-a]pyridin-7-amine,
2-(3-(3-fluoropropoxy)phenyl)-N-methylimidazo[1,2-a]pyridin-7-amine,
2-(4-(4-fluoropiperidin-1-yl)phenyl)-N-methylimidazo[1,2-a]pyridin-7-amine,
4-(7-(2-fluoroethylamino)imidazo[1,2-a]pyridin-2-yl)-2-methoxyphenol,
4-(7-(2-fluoroethylamino)imidazo[1,2-a]pyridin-2-yl) phenol,
3-(7-(2-fluoroethylamino)imidazo[1,2-a]pyridin-2-yl) phenol,
N-(2-fluoroethyl)-2-(4-morpholin-4-ylphenyl)imidazo[1,2-a]pyridin-7-amine, and
N-cyclopropyl-2-[4-(3-fluoropropoxy)phenyl]imidazo[1,2-a]pyridin-7-amine, or a pharmaceutically acceptable salt thereof.

2. A compound of formula IB:

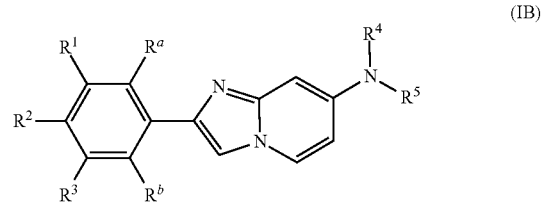

(IB)

wherein
$R^1$ and $R^2$ form, together with the carbon atoms to which they are attached, a ring consisting of —OCH$_2$CH$_2$O—, OCH$_2$O—, OCH$_2$CH$_2$CH$_2$O— or —NHC(O)CH$_2$O—;

R³ is hydrogen or lower alkoxy;
R⁴ is hydrogen or lower alkyl;
R⁵ is lower alkyl, cycloalkyl, lower alkyl substituted by hydroxy or lower alkyl substituted by halogen,
$R^a$ is hydrogen or 3H;
$R^b$ is hydrogen, hydroxy or ³H;
or a pharmaceutically acceptable acid addition salt, a racemic mixture or its corresponding enantiomer and/or optical isomers thereof.

3. A compound according to claim 2, wherein the compound is selected from the group consisting of:
[2-(2,3-dihydro-benzo[1,4]dioxin-6-yl)-imidazo[1,2-a]pyridin-7-yl]-methyl-amine,
[2-(2,3-dihydro-benzo[1,4]dioxin-6-yl)-imidazo[1,2-a]pyridin-7-yl]-dimethyl-amine,
[2-(2,3-dihydro-benzo[1,4]dioxin-6-yl)-imidazo[1,2-a]pyridin-7-yl]-(2-fluoro-ethyl)-methyl-amine,
(2-benzo[1,3]dioxol-5-yl-imidazo[1,2-a]pyridin-7-yl)-methyl-amine,
(2-benzo[1,3]dioxol-5-yl-imidazo[1,2-a]pyridin-7-yl)-dimethyl-amine,
(2-benzo[1,3]dioxol-5-yl-imidazo[1,2-a]pyridin-7-yl)-(2-fluoro-ethyl)-methyl-amine,
(2-benzo[1,3]dioxol-5-yl-imidazo[1,2-a]pyridin-7-yl)-(2-fluoro-ethyl)-amine,
N-[2-(3,4-dihydro-2H-benzo[b][1,4]dioxepin-7-yl)-imidazo[1,2-a]pyridin-7-yl]-methyl-amine,
6-(7-methylamino-imidazo[1,2-a]pyridin-2-yl)-4H-benzo[1,4]oxazin-3-one, and
2-(2,3-dihydrobenzo[b][1,4]dioxin-6-yl)-N-(2-fluoroethyl)imidazo[1,2-a]pyridin-7-amine, or a pharmaceutically acceptable salt thereof.

4. A compound of formula IC:

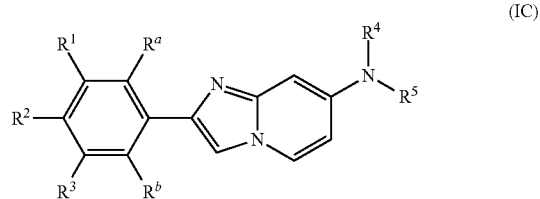

(IC)

wherein
R¹ and R² form, together with the carbon atoms to which they are attached, a ring consisting of —OCH₂CH₂O—, OCH₂O—, OCH₂CH₂CH₂O— or —NHC(O)CH₂O—;
R³ is hydrogen or lower alkoxy;
R⁴ and R⁵ form, together with the nitrogen atom to which they are attached, a ring consisting of —CH₂CH₂CHRCH₂CH₂—, —CH₂CHRCH₂CH₂—, —CH₂CH₂OCH₂CH₂—, —CH₂CH₂NR'CH₂CH₂—, CH₂CHR— or —CH₂CH₂CH₂—; wherein
R is hydrogen, halogen, lower alkyl, lower alkoxy or lower alkyl substituted by halogen;
R' is lower alkyl substituted by halogen;
$R^a$ is hydrogen or 3H;
$R^b$ is hydrogen, hydroxy or ³H;
or a pharmaceutically acceptable acid addition salt, a racemic mixture or its corresponding enantiomer and/or optical isomers thereof.

5. A compound according to claim 4, wherein the compound is
2-benzo[1,3]dioxol-5-yl-7-[4-(2-fluoro-ethyl)-piperazin-1-yl]-imidazo[1,2-a]pyridine,
2-(2,3-dihydro-benzo[1,4]dioxin-6-yl)-7-[4-(2-fluoro-ethyl)-piperidin-1-yl]-imidazo[1,2-a]pyridine,
2-benzo[1,3]dioxol-5-yl-7-(4-fluoro-piperidin-1-yl)-imidazo[1,2-a]pyridine, or
2-(2,3-dihydro-benzo[1,4]dioxin-6-yl)-7-(4-fluoro-piperidin-1-yl)-imidazo[1,2-a]pyridine, or a pharmaceutically acceptable salt thereof.

6. A compound selected from the group consisting of:
7-(4-fluoropiperidin-1-yl)-2-phenylimidazo[1,2-a]pyridine,
(S)-7-(3-fluoropyrrolidin-1-yl)-2-(4-methoxyphenyl)imidazo[1,2-a]pyridine,
(R)-7-(3-fluoropyrrolidin-1-yl)-2-(4-methoxyphenyl)imidazo[1,2-a]pyridine,
2-(3-methoxy-phenyl)-7-piperidin-1-yl-imidazo[1,2-a]pyridine,
2-(3-methoxy-phenyl)-7-pyrrolidin-1-yl-imidazo[1,2-a]pyridine,
2-(3-methoxy-phenyl)-7-morphonlin-1-yl-imidazo[1,2-a]pyridine,
2-(4-methoxy-phenyl)-7-pyrrolidin-1-yl-imidazo[1,2-a]pyridine,
2-(4-methoxy-phenyl)-7-piperidin-1-yl-imidazo[1,2-a]pyridine,
2-(4-methoxy-phenyl)-7-morphonlin-1-yl-imidazo[1,2-a]pyridine,
7-(4-fluoro-piperidin-1-yl)-2-(4-methoxy-phenyl)-imidazo[1,2-a]pyridine,
7-[4-(2-fluoro-ethyl)-piperazin-1-yl]-2-(4-methoxy-phenyl)-imidazo[1,2-a]pyridine,
7-azetidin-1-yl-2-(4-methoxy-phenyl)-imidazo[1,2-a]pyridine,
(S)-7-(3-fluoropyrrolidin-1-yl)-2-phenyl-imidazo[1,2-a]pyridine,
7-morpholin-4-yl-2-m-tolyl-imidazo[1,2-a]pyridine,
7-morpholin-4-yl-2-p-tolyl-imidazo[1,2-a]pyridine,
4-(7-azetidin-1-yl-imidazo[1,2-a]pyri din-2-yl)-phenol,
{4-[7-(4-fluoro-piperidin-1-yl)-imidazo[1,2-a]pyridin-2-yl]-phenyl}-dimethyl-amine,
7-((R)-3-fluoro-pyrrolidin-1-yl)-2-phenyl-imidazo[1,2-a]pyridine,
7-((R)-3-methoxy-pyrrolidin-1-yl)-2-phenyl-imidazo[1,2-a]pyridine,
7-((S)-3-methoxy-pyrrolidin-1-yl)-2-m-tolyl-imidazo[1,2-a]pyridine,
2-(4-fluoromethoxy-phenyl)-7-morpholin-4-yl-imidazo[1,2-a]pyridine,
7-azetidin-1-yl-2-p-tolyl-imidazo[1,2-a]pyridine,
7-azetidin-1-yl-2-m-tolyl-imidazo[1,2-a]pyridine,
7-((R)-3-methoxy-pyrrolidin-1-yl)-2-p-tolyl-imidazo[1,2-a]pyridine,
7-(4-fluoro-piperidin-1-yl)-2-p-tolyl-imidazo[1,2-a]pyridine,
7-[4-(2-fluoro-ethyl)-piperidin-1-yl]-2-phenyl-imidazo[1,2-a]pyridine,
7-((S)-3-methoxy-pyrrolidin-1-yl)-2-phenyl-imidazo[1,2-a]pyridine,
7-(4-fluoro-piperidin-1-yl)-2-(3-methoxy-phenyl)-imidazo[1,2-a]pyridine,
7-(4-fluoro-piperidin-1-yl)-2-m-tolyl-imidazo[1,2-a]pyridine,
7-azetidin-1-yl-2-(4-fluoromethoxy-phenyl)-imidazo[1,2-a]pyridine, 7-[4-(2-fluoro-ethyl)-piperidin-1-yl]-2-(4-methoxy-phenyl)-imidazo[1,2-a]pyridine, 7-[4-(2-fluoro-ethyl)-piperidin-1-yl]-2-m-tolyl-imidazo[1,2-a]pyridine, 7-((R)-3-methoxy-pyrrolidin-1-yl)-2-m-tolyl-imidazo[1,2-a]pyridine, 7-[4-(2-fluoro-ethyl)-piperidin-1-yl]-2-p-tolyl-imidazo[1,2-a]pyridine, 7-((S)-3-methoxy-pyrrolidin-1-yl)-2-p-tolyl-imidazo[1,2-a]pyridine, 7-(azetidin-1-yl)-2-(3-methoxyphenyl)imidazo[1,2-a]pyridine, 7-(azetidin-1-yl)-2-[4-(2-fluoroethoxy)phenyl]imidazo[1,2-a]pyridine, 7-(azetidin-1-yl)-2-[3-(fluoromethoxy)phenyl]imidazo[1,2-a]pyridine, 2-(4-methoxyphenyl)-7-(2-methylaziridin-1-yl)imidazo[1,2-a]pyridine, 7-(azetidin-1-yl)-2-(3-(2-fluoroethoxy)phenyl)imidazo[1,2-a]pyridine, and 7-(azetidin-1-yl)-2-(4-(2-(2-fluoroethoxy)ethoxy)phenyl)imidazo[1,2-a]pyridine, or a pharmaceutically acceptable salt thereof.

7. The compound N-(2-fluoroethyl)-2-phenylimidazo[1,2-a]pyridin-7-amine,
or N-(2-fluoroethyl)-N-methyl-2-phenylimidazo[1,2-a]pyridin-7-amine, or an enantiomer thereof, or a pharmaceutically acceptable acid addition salt of the compound or of the enantiomer.

* * * * *